United States Patent
Carver et al.

(10) Patent No.: US 9,956,399 B2
(45) Date of Patent: *May 1, 2018

(54) MEDICAL DEVICE FOR REMOVING AN IMPLANTED OBJECT

(71) Applicant: The Spectranetics Corporation, Colorado Springs, CO (US)

(72) Inventors: Robert Carver, Colorado Springs, CO (US); Weston H. Lee, Colorado Springs, CO (US); Brian E. Kagarise, Colorado Springs, CO (US); Bruce A. Hoo, Colorado Springs, CO (US); Peter Wilbur Gleason, Berkeley, CA (US); Phillip Charles Halbert, San Francisco, CA (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/406,033

(22) Filed: Jan. 13, 2017

(65) Prior Publication Data

US 2017/0157392 A1 Jun. 8, 2017

Related U.S. Application Data

(63) Continuation of application No. 14/627,950, filed on Feb. 20, 2015, which is a continuation-in-part of (Continued)

(51) Int. Cl.
*A61B 17/3205* (2006.01)
*A61N 1/05* (2006.01)
(Continued)

(52) U.S. Cl.
CPC ...... *A61N 1/0573* (2013.01); *A61B 17/32002* (2013.01); *A61B 17/3468* (2013.01);
(Continued)

(58) Field of Classification Search
CPC .... A61N 1/0573; A61N 1/05; A61B 17/3205; A61B 17/32; A61B 17/34
(Continued)

(56) References Cited

U.S. PATENT DOCUMENTS 1,663,761 A 3/1928 Johnson
2,708,437 A 5/1955 Selwyn
(Continued)

FOREIGN PATENT DOCUMENTS

JP H05506382 A 9/1993
JP 2004516073 A 6/2004
(Continued)

OTHER PUBLICATIONS

Extended European Search Report issued in EP Application No. 14770860.6, dated Jan. 10, 2017, 14 pages.
(Continued)

*Primary Examiner* — Carl H Layno
*Assistant Examiner* — Jon Eric C Morales
(74) *Attorney, Agent, or Firm* — Faegre Baker Daniels LLP

(57) ABSTRACT

Methods and devices for separating an implanted object, such as a pacemaker lead, from tissue surrounding such object in a patient's vasculature system. Specifically, the surgical device includes a handle, an elongate sheath and a circular cutting blade that extends from the distal end of the sheath upon actuating the handle. The circular cutting blade is configured to engage the tissue surrounding an implanted lead and cut such tissue in a coring fashion as the surgical device translates along the length of the lead, thereby allowing the lead, as well as any tissue remaining attached to the lead, to enter the device's elongate shaft. The surgical device has a barrel cam cylinder in the handle assembly that imparts rotation of the blade and a separate cam mechanism
(Continued)

in the tip of outer sheath assembly that imparts and controls the extension and retraction of the blade. The barrel cam cylinder and cam mechanism cooperate to cause the blade to rotate in a first direction and extend from and retract in the outer sheath due to a first actuation of the handle and to rotate in a second direction and extend and retract in the outer sheath due to a second actuation of the handle.

11 Claims, 51 Drawing Sheets

Related U.S. Application Data application No. PCT/US2014/026496, filed on Mar. 13, 2014.

(60) Provisional application No. 61/793,597, filed on Mar. 15, 2013, provisional application No. 61/947,377, filed on Mar. 3, 2014, provisional application No. 62/058,790, filed on Oct. 2, 2014, provisional application No. 62/113,865, filed on Feb. 9, 2015.

(51) Int. Cl.
*A61B 17/34* (2006.01)
*A61B 17/32* (2006.01)

(52) U.S. Cl.
CPC ............. *A61B 2017/320032* (2013.01); *A61N 2001/0578* (2013.01)

(58) Field of Classification Search
USPC .......................................................... 607/116
See application file for complete search history.

(56) References Cited

U.S. PATENT DOCUMENTS

| | | |
|---|---|---|
| 3,400,708 A | 9/1968 | Scheidt |
| 3,614,953 A | 10/1971 | Moss |
| 3,756,242 A | 9/1973 | Coss |
| 4,051,596 A | 10/1977 | Hofmann |
| 4,203,444 A | 5/1980 | Bonnell et al. |
| 4,246,902 A | 1/1981 | Martinez |
| 4,274,414 A | 6/1981 | Johnson et al. |
| D267,145 S | 12/1982 | Kaneko |
| 4,471,777 A | 9/1984 | McCorkle, Jr. |
| 4,517,977 A | 5/1985 | Frost |
| 4,582,056 A | 4/1986 | McCorkle et al. |
| 4,598,710 A | 7/1986 | Kleinberg et al. |
| 4,601,290 A | 7/1986 | Effron et al. |
| 4,646,738 A | 3/1987 | Trott |
| 4,662,869 A | 5/1987 | Wright |
| 4,674,502 A | 6/1987 | Imonti |
| 4,729,763 A | 3/1988 | Henrie |
| 4,754,755 A | 7/1988 | Husted |
| 4,767,403 A | 8/1988 | Hodge |
| 4,785,826 A | 11/1988 | Ward |
| D309,350 S | 7/1990 | Sutherland et al. |
| 4,943,289 A | 7/1990 | Goode et al. |
| 4,950,277 A | 8/1990 | Farr |
| 4,988,347 A | 1/1991 | Goode et al. |
| 5,011,482 A | 4/1991 | Goode et al. |
| 5,013,310 A | 5/1991 | Goode et al. |
| 5,031,634 A | 7/1991 | Simon |
| 5,152,744 A | 10/1992 | Krause et al. |
| 5,201,316 A | 4/1993 | Pomeranz et al. |
| 5,207,683 A | 5/1993 | Goode et al. |
| 5,217,454 A | 6/1993 | Khoury |
| 5,261,877 A | 11/1993 | Fine et al. |
| 5,263,928 A | 11/1993 | Trauthen et al. |
| 5,275,609 A | 1/1994 | Pingleton et al. |
| 5,281,220 A | 1/1994 | Blake et al. |
| 5,290,275 A | 3/1994 | Kittrell et al. |
| 5,290,303 A | 3/1994 | Pingleton et al. |
| 5,383,199 A | 1/1995 | Laudenslager et al. |
| 5,395,328 A | 3/1995 | Ockuly et al. |
| 5,411,513 A | 5/1995 | Ireland et al. |
| 5,423,330 A | 6/1995 | Lee |
| 5,423,806 A | 6/1995 | Dale et al. |
| 5,456,680 A | 10/1995 | Taylor et al. |
| 5,484,433 A | 1/1996 | Taylor et al. |
| 5,507,751 A | 4/1996 | Goode et al. |
| 5,562,694 A | 10/1996 | Sauer et al. |
| 5,569,284 A | 10/1996 | Young et al. |
| 5,575,797 A | 11/1996 | Neubauer et al. |
| 5,595,186 A | 1/1997 | Rubinstein et al. |
| 5,620,451 A | 4/1997 | Rosborough |
| 5,632,749 A | 5/1997 | Goode et al. |
| 5,651,781 A | 7/1997 | Grace |
| 5,697,936 A | 12/1997 | Shipko et al. |
| 5,718,237 A | 2/1998 | Haaga |
| 5,725,523 A | 3/1998 | Mueller |
| 5,766,164 A | 6/1998 | Mueller et al. |
| 5,782,823 A | 7/1998 | Mueller |
| 5,792,151 A | 8/1998 | Heck et al. |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,863,294 A | 1/1999 | Alden |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,910,150 A | 6/1999 | Saadat |
| 5,916,210 A | 6/1999 | Winston |
| 5,931,848 A | 8/1999 | Saadat |
| 5,941,893 A | 8/1999 | Saadat |
| 5,951,581 A | 9/1999 | Saadat et al. |
| 5,972,012 A | 10/1999 | Ream et al. |
| 5,980,515 A | 11/1999 | Tu |
| 5,980,545 A | 11/1999 | Pacala et al. |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,027,497 A | 2/2000 | Daniel et al. |
| 6,033,402 A | 3/2000 | Tu et al. |
| 6,036,685 A | 3/2000 | Mueller |
| 6,039,748 A | 3/2000 | Savage et al. |
| 6,051,008 A | 4/2000 | Saadat et al. |
| 6,063,037 A | 5/2000 | Mittermeier et al. |
| 6,066,131 A | 5/2000 | Mueller et al. |
| 6,080,175 A | 6/2000 | Hogendijk |
| 6,083,237 A | 7/2000 | Huitema et al. |
| 6,099,537 A | 8/2000 | Sugai et al. |
| 6,102,926 A | 8/2000 | Tartaglia et al. |
| D430,781 S | 9/2000 | Hillegonds |
| 6,117,149 A | 9/2000 | Sorensen et al. |
| 6,120,520 A | 9/2000 | Saadat et al. |
| 6,126,654 A | 10/2000 | Giba et al. |
| 6,136,005 A | 10/2000 | Goode et al. |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,203,537 B1 | 3/2001 | Adrian |
| 6,210,400 B1 | 4/2001 | Hebert et al. |
| 6,228,076 B1 | 5/2001 | Winston et al. |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |

(56) References Cited

U.S. PATENT DOCUMENTS

| | | |
|---|---|---|
| 6,290,668 B1 | 9/2001 | Gregory et al. |
| 6,315,774 B1 | 11/2001 | Daniel et al. |
| 6,324,434 B2 | 11/2001 | Coe et al. |
| 6,379,351 B1 | 4/2002 | Thapliyal et al. |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley et al. |
| 6,537,314 B2 | 3/2003 | Langberg et al. |
| 6,540,865 B1 | 4/2003 | Miekka et al. |
| 6,554,779 B2 | 4/2003 | Viola et al. |
| 6,558,382 B2 | 5/2003 | Jahns et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,860,860 B2 | 3/2005 | Viola |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,014,614 B2 | 3/2006 | Casula |
| 7,022,133 B2 | 4/2006 | Yee et al. |
| 7,033,324 B2 | 4/2006 | Giusti et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| D594,983 S | 6/2009 | Price et al. |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |

(56) References Cited

U.S. PATENT DOCUMENTS

| | | |
|---|---|---|
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| D631,155 S | 1/2011 | Peine et al. |
| 7,875,018 B2 | 1/2011 | Tockman et al. |
| 7,875,049 B2 | 1/2011 | Eversull et al. |
| D631,965 S | 2/2011 | Price et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,930,040 B1 | 4/2011 | Kelsch et al. |
| D638,935 S | 5/2011 | Gilmore et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,434 B2 | 8/2011 | Olson |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| D650,074 S | 12/2011 | Hunt et al. |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,303,570 B2 | 11/2012 | Gregorich et al. |
| 8,323,240 B2 | 12/2012 | Wulfman et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,364,280 B2 | 1/2013 | Marnfeldt et al. |
| 8,372,098 B2 | 2/2013 | Tran |
| D679,010 S | 3/2013 | Kitayama et al. |
| 8,394,110 B2 | 3/2013 | Catanese et al. |
| 8,394,113 B2 | 3/2013 | Wei et al. |
| 8,424,535 B2 | 4/2013 | Hessler et al. |
| 8,425,535 B2 | 4/2013 | McLean et al. |
| D687,549 S | 8/2013 | Johnson et al. |
| D697,618 S | 1/2014 | Gonzales et al. |
| 8,622,275 B2 | 1/2014 | Baxter et al. |
| D706,928 S | 6/2014 | Harrison et al. |
| D708,742 S | 7/2014 | Dallemagne et al. |
| 8,961,551 B2 | 2/2015 | Taylor |
| 9,028,520 B2 | 5/2015 | Taylor et al. |
| 9,232,945 B2 | 1/2016 | Zingman |
| 9,283,040 B2 | 3/2016 | Hendrick et al. |
| 9,289,226 B2 | 3/2016 | Taylor |
| D765,243 S | 8/2016 | Halbert |
| D770,616 S | 11/2016 | Halbert et al. |
| 9,622,762 B2 | 4/2017 | Dahm et al. |
| D786,430 S | 5/2017 | Davies et al. |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0039427 A1 | 11/2001 | Dinger et al. |
| 2001/0041899 A1 | 11/2001 | Foster |
| 2001/0044568 A1 | 11/2001 | Langberg et al. |
| 2002/0002372 A1 | 1/2002 | Jahns et al. |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0087046 A1 | 7/2002 | Sullivan et al. |
| 2002/0087151 A1 | 7/2002 | Mody et al. |
| 2002/0103459 A1 | 8/2002 | Sparks et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151918 A1 | 10/2002 | Lafontaine et al. |
| 2002/0151961 A1 | 10/2002 | Lashinski et al. |
| 2002/0165425 A1 | 11/2002 | Yoon et al. |
| 2002/0183735 A1 | 12/2002 | Edwards et al. |
| 2002/0188278 A1 | 12/2002 | Tockman et al. |

(56) References Cited

U.S. PATENT DOCUMENTS

| | | |
|---|---|---|
| 2003/0009146 A1 | 1/2003 | Muni et al. |
| 2003/0036788 A1 | 2/2003 | Coe et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0105451 A1 | 6/2003 | Westlund et al. |
| 2003/0125619 A1 | 7/2003 | Manning et al. |
| 2003/0125709 A1 | 7/2003 | Eidenschink |
| 2003/0167056 A1 | 9/2003 | Jahns et al. |
| 2003/0187460 A1 | 10/2003 | Chin et al. |
| 2003/0187461 A1 | 10/2003 | Chin |
| 2003/0199916 A1 | 10/2003 | Yee et al. |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0133220 A1 | 7/2004 | Lashinski et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027337 A1 | 2/2005 | Rudko et al. |
| 2005/0038419 A9 | 2/2005 | Arnold et al. |
| 2005/0054948 A1 | 3/2005 | Goldenberg |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096740 A1 | 5/2005 | Langberg et al. |
| 2005/0119615 A1 | 6/2005 | Noriega et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0267557 A1 | 12/2005 | Flynn et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2006/0004346 A1 | 1/2006 | Begg |
| 2006/0041250 A1 | 2/2006 | Poleo |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0100687 A1 | 5/2006 | Fahey et al. |
| 2006/0116746 A1 | 6/2006 | Chin |
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0123892 A1 | 5/2007 | Ries et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0276419 A1 | 11/2007 | Rosenthal |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039883 A1 | 2/2008 | Nohilly |
| 2008/0039884 A1 | 2/2008 | Nohilly et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0077085 A1 | 3/2008 | Eidenschink et al. |
| 2008/0097398 A1 | 4/2008 | Mitelberg et al. |
| 2008/0097426 A1 | 4/2008 | Root et al. |
| 2008/0103439 A1 | 5/2008 | Torrance et al. |
| 2008/0103446 A1 | 5/2008 | Torrance et al. |

(56) References Cited

U.S. PATENT DOCUMENTS

| | | |
|---|---|---|
| 2008/0103516 A1 | 5/2008 | Wulfman et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0154296 A1 | 6/2008 | Taylor et al. |
| 2008/0183163 A1 | 7/2008 | Lampropoulos et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0234602 A1 | 9/2008 | Oostman et al. |
| 2008/0234698 A1 | 9/2008 | Oostman et al. |
| 2008/0234716 A1 | 9/2008 | Kiester |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0277445 A1 | 11/2008 | Zergiebel et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0149847 A1 | 6/2009 | Yadin et al. |
| 2009/0157045 A1 | 6/2009 | Haarala et al. |
| 2009/0192439 A1 | 7/2009 | Lamson et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2009/0270862 A1 | 10/2009 | Arcenio |
| 2009/0270898 A1 | 10/2009 | Chin et al. |
| 2010/0004606 A1 | 1/2010 | Hansen et al. |
| 2010/0030154 A1 | 2/2010 | Duffy |
| 2010/0030161 A1 | 2/2010 | Duffy |
| 2010/0030248 A1 | 2/2010 | Palmer et al. |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217081 A1 | 8/2010 | Deppmeier et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Katoh et al. |
| 2010/0280496 A1 | 11/2010 | Shippert |
| 2010/0305594 A1 | 12/2010 | Opie |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0029278 A1 | 2/2012 | Sato et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006167 A1 | 1/2013 | Alvarez et al. |
| 2013/0006228 A1 | 1/2013 | Johnson et al. |
| 2013/0035676 A1 | 2/2013 | Mitchell et al. |
| 2013/0066345 A1 | 3/2013 | Wilkinson |
| 2013/0096582 A1 | 4/2013 | Cheng et al. |
| 2013/0103047 A1 | 4/2013 | Steingisser et al. |
| 2013/0131548 A1 | 5/2013 | McGhie et al. |
| 2014/0277037 A1 | 9/2014 | Grace et al. |
| 2015/0105796 A1 | 4/2015 | Grace |
| 2015/0164530 A1 | 6/2015 | Carver et al. |
| 2015/0196297 A1 | 7/2015 | Stopek |
| 2015/0258333 A1* | 9/2015 | Carver ............. A61N 1/0573 606/129 |
| 2015/0258334 A1* | 9/2015 | Carver ............. A61N 1/0573 607/116 |
| 2015/0305744 A1 | 10/2015 | Moore et al. |
| 2015/0342680 A1 | 12/2015 | Schneider |

(56) References Cited

U.S. PATENT DOCUMENTS

| | | | |
|---|---|---|---|
| 2016/0015963 A1 | 1/2016 | Grace et al. |
| 2016/0120562 A1 | 5/2016 | Taylor |
| 2017/0172622 A1 | 6/2017 | Grace et al. |

FOREIGN PATENT DOCUMENTS

| | | | |
|---|---|---|---|
| WO | 1991017711 A1 | 11/1991 |
| WO | 1995033513 A1 | 12/1995 |
| WO | 1999007295 A1 | 2/1999 |
| WO | 1999049937 A1 | 10/1999 |
| WO | 1999058066 A1 | 11/1999 |
| WO | 2001076680 A1 | 10/2001 |
| WO | 2002049690 A9 | 5/2003 |
| WO | 2004049956 A2 | 6/2004 |
| WO | 2004080345 A2 | 9/2004 |
| WO | 2004080507 A2 | 9/2004 |
| WO | 2006007410 A2 | 1/2006 |
| WO | 2008005888 A2 | 1/2008 |
| WO | 2008005891 A2 | 1/2008 |
| WO | 2008042987 A2 | 4/2008 |
| WO | 2009005779 A1 | 1/2009 |
| WO | 2009054968 A1 | 4/2009 |
| WO | 2009065082 A1 | 5/2009 |
| WO | 2009126309 A2 | 10/2009 |
| WO | 2011003113 A1 | 1/2011 |
| WO | 2011084863 A2 | 7/2011 |
| WO | 2011133941 A2 | 10/2011 |
| WO | 2011162595 A1 | 12/2011 |
| WO | 2012040239 A1 | 3/2012 |
| WO | 2012009697 A4 | 4/2012 |
| WO | 2012098335 A1 | 7/2012 |
| WO | 2012114333 A1 | 8/2012 |
| WO | 2012177117 A1 | 12/2012 |
| WO | 2013036588 A1 | 3/2013 |
| WO | 2014151814 A1 | 9/2014 |
| WO | 2015134383 A1 | 9/2015 |

OTHER PUBLICATIONS

U.S. Appl. No. 15/462,357 entitled Medical Device for Removing an Implanted Object, filed Mar. 17, 2017.
European Search Report issued in EP Application No. 15757928.5, dated Sep. 14, 2017, 6 pages.
Extended European Search Report issued in EP Application No. 15757744.6, dated Sep. 14, 2017, 5 pages.
Decision to Grant for European Patent Application No. 07255018.9, dated Aug. 8, 2013, 2 pages.
Department of Health and Ageing in Australian Government, "Horizon Scanning Technology Prioritising: Laser Extraction Systems." 2010. 15 pages.
EP extended Search Report dated Oct. 21, 2009; Application No. 07255019.7, 8 pages.
Extended European Search Repor] issued in Application No. 14770355.7, dated Sep. 15, 2016, 7 pages.
Extended European Search Report for European Application No. 07255018.9, dated Nov. 12, 2010, 7 pages.
Final Action for U.S. Appl. No. 11/615,005, dated Nov. 9, 2009, 10 pages.
Final Action for U.S. Appl. No. 11/615,005, dated Nov. 21, 2013, 20 pages.
Intent to Grant for European Patent Application No. 07255018.9, dated Nov. 29, 2012, 7 pages.
International Preliminary Report on Patentability issued in PCT/US2015/016899, dated Sep. 15, 2016, 7 pages.
International Search Report and Written Opinion for International Patent Application No. PCT/US2013/059434, dated Dec. 13, 2013, 14 pages.
International Search Report and Written Opinion issued in PCT/US2014/021167 dated Jun. 26, 2014, 19 pages.
International Search Report and Written Opinion issued in PCT/US2014/026496 dated Jul. 30, 2014, 16 pages.

International Search Report and Written Opinion issued in PCT/US2015/016899, dated May 1, 2015, 14 pages.
International Search Report and Written Opinion issued in PCT/US2015/018305, dated May 28, 2015, 14 pages.
International Search Report and Written Opinion issued in PCT/US2015/058227, dated Feb. 3, 2016, 18 pages.
International Search Report and Written Opinion issued in PCT/US2016/049108, dated Dec. 5, 2016, 9 pages.
Notice of Allowance for European Patent Application No. 07255018.9, dated Jul. 26, 2012, 47 pages.
Notice of Allowance for Japan Patent Application No. 2007-333273, dated Jan. 16, 2014, 3 pages.
Official Action for European Patent Application No. 07255018.9, dated Jul. 19, 2011, 3 pages.
Official Action for U.S. Appl. No. 11/615,005, dated Apr. 16, 2009, 13 pages.
Official Action for U.S. Appl. No. 11/615,005, dated Feb. 11, 2011, 12 pages.
Official Action for U.S. Appl. No. 11/615,005, dated Jul. 21, 2010, 10 pages.
Official Action for U.S. Appl. No. 11/615,005, dated Mar. 14, 2013, 16 pages.
Official Action for U.S. Appl. No. 13/800,728, dated Jan. 16, 2014, 14 pages.
Official Action with English translation for Japan Patent Application No. 2007-333173, dated Apr. 30, 2013, 5 pages.
Official Action with English translation for Japan Patent Application No. 2007-333173, dated Aug. 13, 2012, 7 pages.
Official Action with English translation for Japan Patent Application No. 2007-333273, dated Jul. 30, 2012, 7 pages.
Official Action with English translation for Japan Patent Application No. 2007-333273, dated Jun. 6, 2013, 10 pages.
PCT Application No. PCT/US2015/016899 entitled Medical Device for Removing an Implanted Object filed Feb. 20, 2015.
PCT Application No. PCT/US2015/018305 entitled Multiple Configuration Surgical Cutting Device filed Mar. 2, 2015.
Supplemental European Search Report issued in EP Application 14770355 dated Sep. 15, 2016, 7 pages.
Supplemental Partial European Search Report issued in EP Application No. EP14770860 dated Sep. 15, 2016, 7 pages.
U.S. Appl. No. 13/800,651 entitled System and Method of Ablative Cutting and Pulsed Vacuum Aspiration, filed Mar. 13, 2013.
U.S. Appl. No. 13/800,675 entitled Laser Catheter With Helical Internal Lumen, filed Mar. 13, 2013.
U.S. Appl. No. 13/800,700 entitled Device and Method of Ablative Cutting With Helical Tip, filed Mar. 13, 2013.
U.S. Appl. No. 13/800,728 entitled Laser Ablation Catheter, filed Mar. 13, 2013.
U.S. Appl. No. 13/828,231 entitled Tissue Slitting Methods and Systems, filed Mar. 14, 2013.
U.S. Appl. No. 13/828,310 entitled Tissue Slitting Methods and Systems, filed Mar. 14, 2013.
U.S. Appl. No. 13/828,383 entitled Tissue Slitting Methods and Systems, filed Mar. 14, 2013.
U.S. Appl. No. 13/828,441 entitled Tissue Slitting Methods and Systems, filed Mar. 14, 2013.
U.S. Appl. No. 13/828,536 entitled Expandable Lead Jacket, filed Mar. 14, 2013.
U.S. Appl. No. 13/828,638 entitled Lead Removal Sleeve, filed Mar. 14, 2013.
U.S. Appl. No. 13/834,405 entitled Retractable Blade for Lead Removal Device, filed Mar. 15, 2013.
U.S. Appl. No. 14/577,976 entitled Surgical Instrument Including an Inwardly Deflecting Cutting Tip for Removing an Implanted Object filed Dec. 19, 2014.
U.S. Appl. No. 14/589,688 entitled Retractable Separating Systems and Methods filed Jan. 5, 2015.
U.S. Appl. No. 14/627,851 entitled Medical Device for Removing an Implanted Object filed Feb. 20, 2015.
U.S. Appl. No. 14/627,950 entitled Medical Device for Removing an Implanted Object filed Feb. 20, 2015.
U.S. Appl. No. 14/635,742 entitled Multiple Configuration Surgical Cutting Device filed Mar. 2, 2015.

(56) References Cited

OTHER PUBLICATIONS

U.S. Appl. No. 14/725,781 entitled Surgical Instrument for Removing an Implanted Object, filed May 29, 2015.
U.S. Appl. No. 29/519,239 entitled Medical Device Handle, filed Mar. 3, 2015.
U.S. Appl. No. 29/575,820 entitled Medical Device Handle, filed Aug. 29, 2016.
U.S. Appl. No. 29/580,392 entitled Medical Device Handle, filed Oct. 7, 2016.
U.S. Appl. No. 61/793,597 entitled Surgical Instrument for Removing an Implanted Object filed Mar. 15, 2013.
U.S. Appl. No. 61/987,993 entitled Dual Mode Mechanical Catheter Cutting System filed May 2, 2014.
U.S. Appl. No. 62/005,315 entitled Surgical Instrument for Removing an Implanted Object filed May 30, 2014.
U.S. Appl. No. 62/058,790 entitled Medical Device for Removing an Implanted Object filed Oct. 2, 2014.
U.S. Appl. No. 62/094,808 entitled Multiple Configuration Surgical Cutting Device filed Dec. 19, 2014.
U.S. Appl. No. 62/113,865 entitled Medical Device for Removing an Implanted Object filed Feb. 9, 2015.

\* cited by examiner

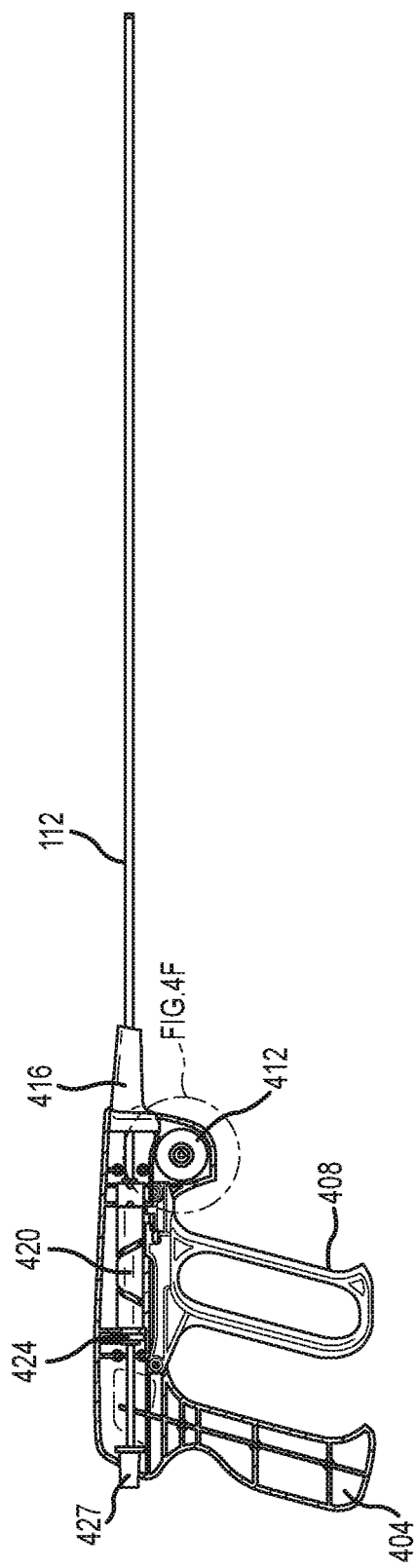

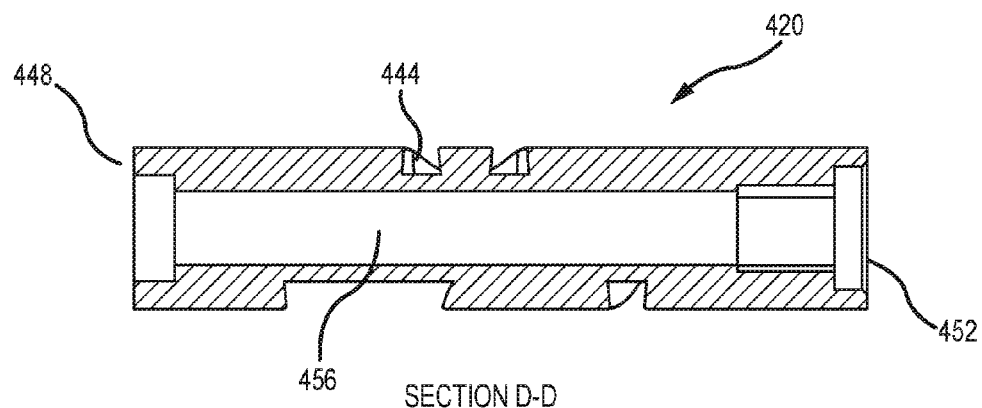
SECTION D-D
FIG.4D
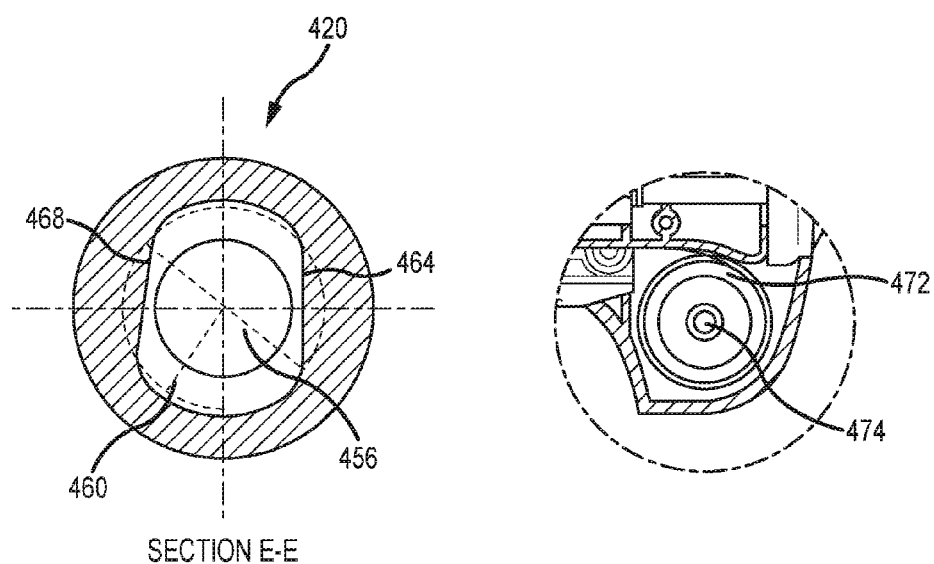
SECTION E-E
FIG.4E
FIG.4F

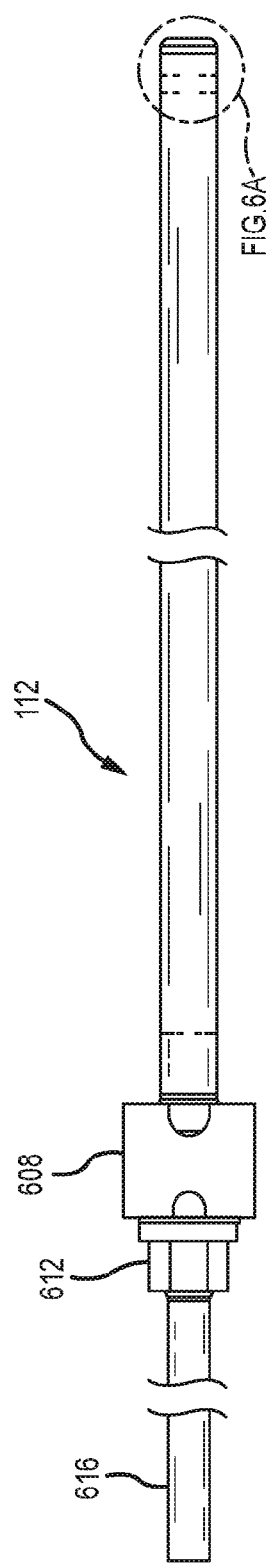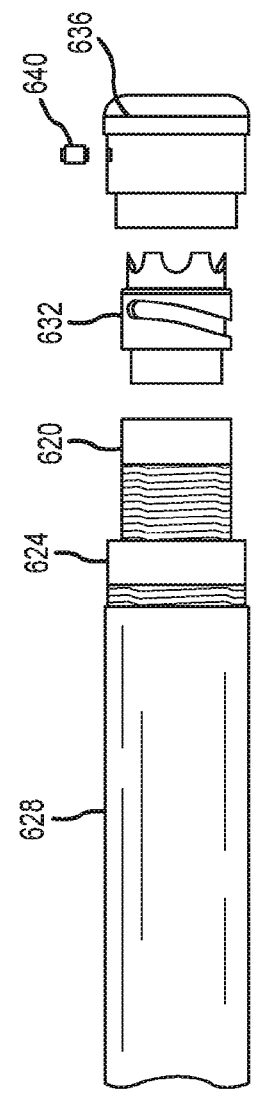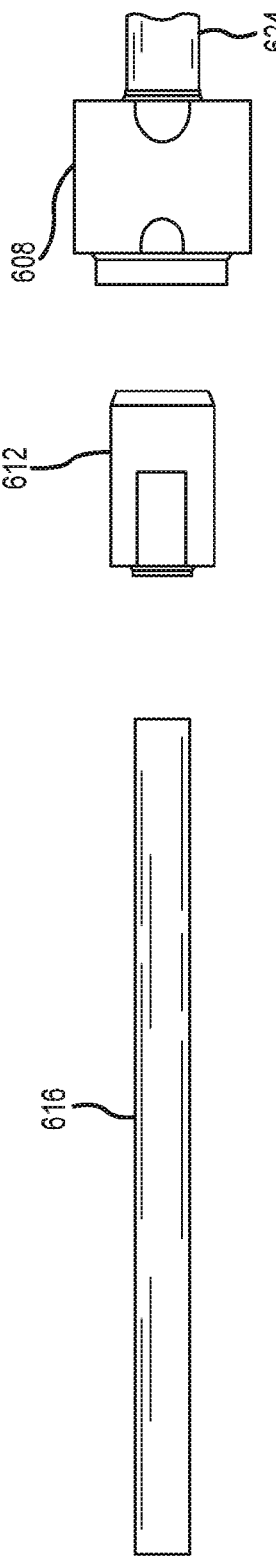

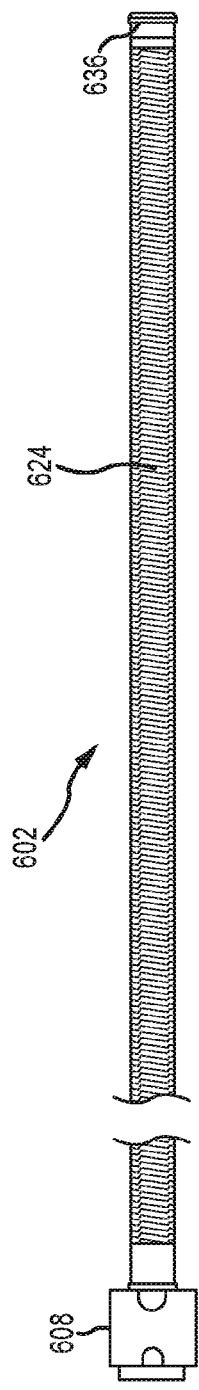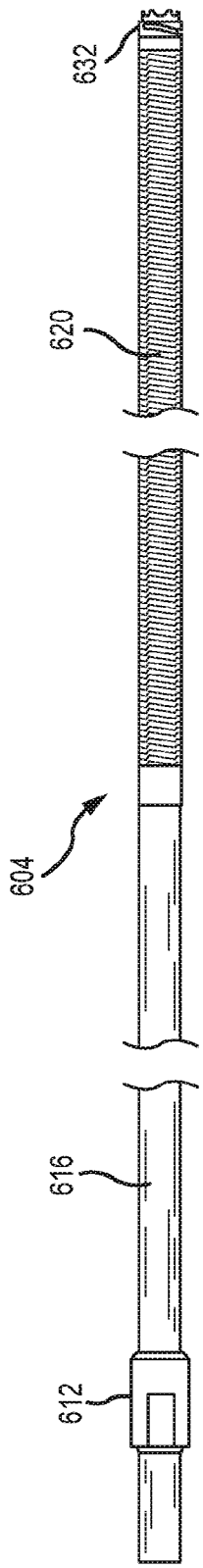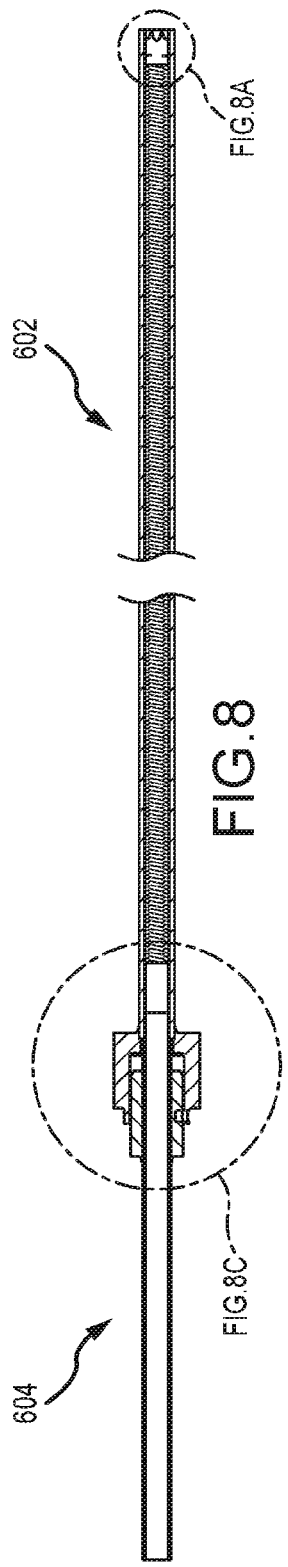

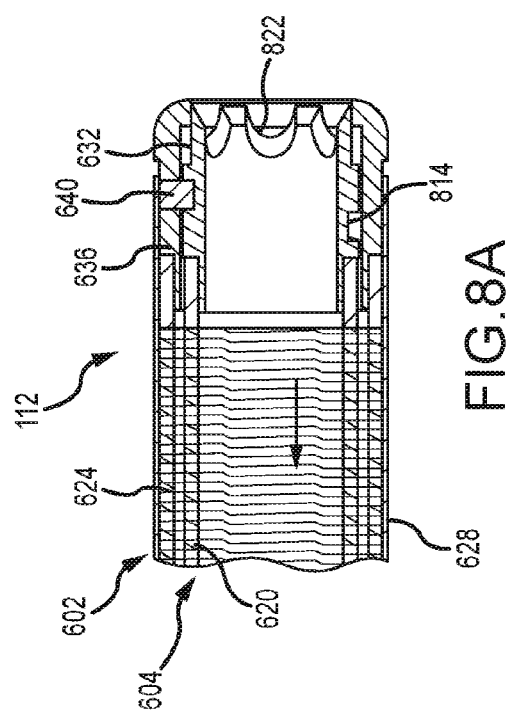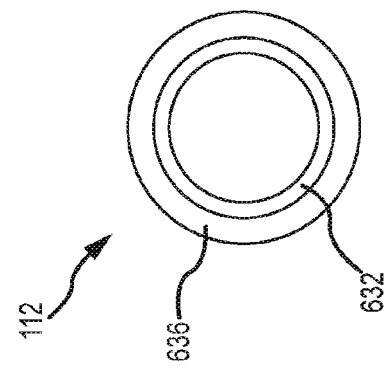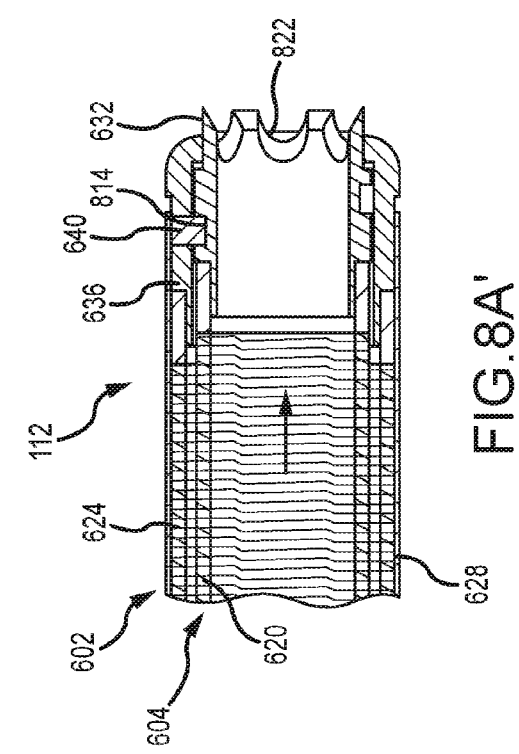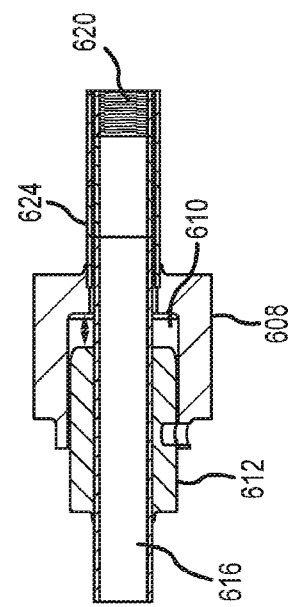

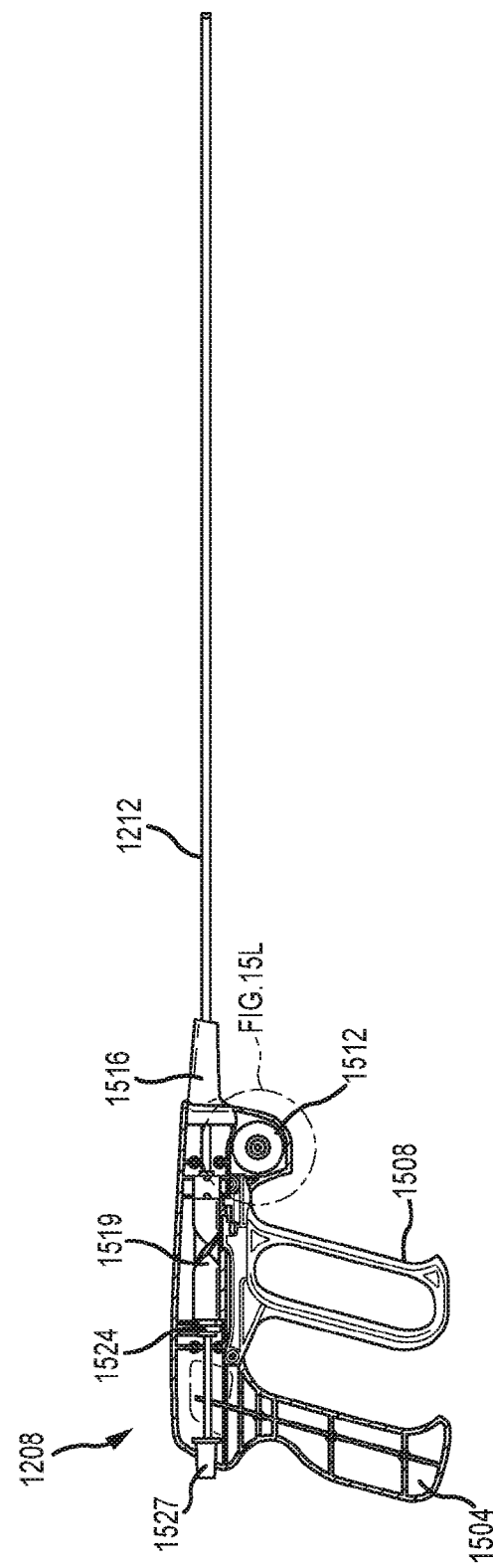

SECTION F-F

SECTION G-G

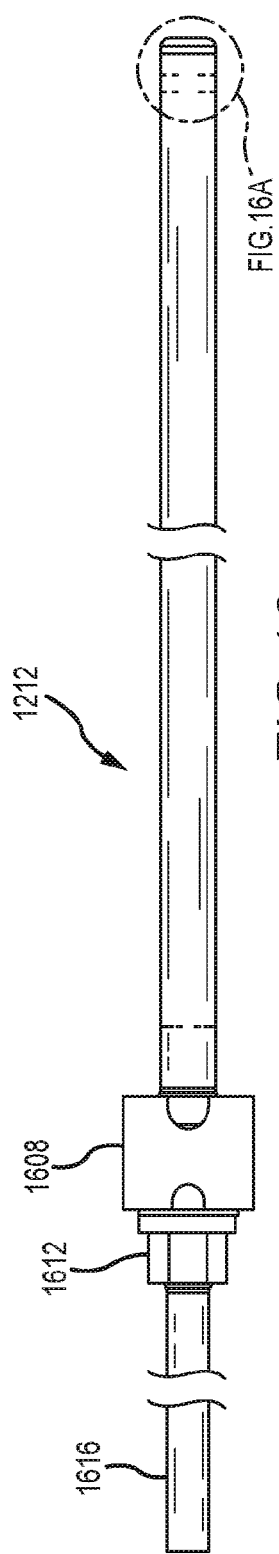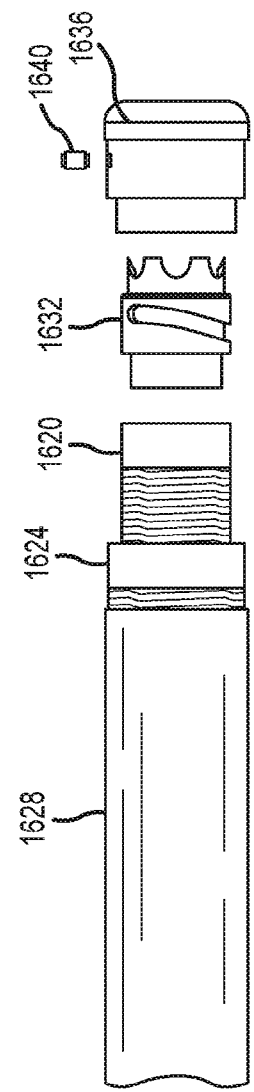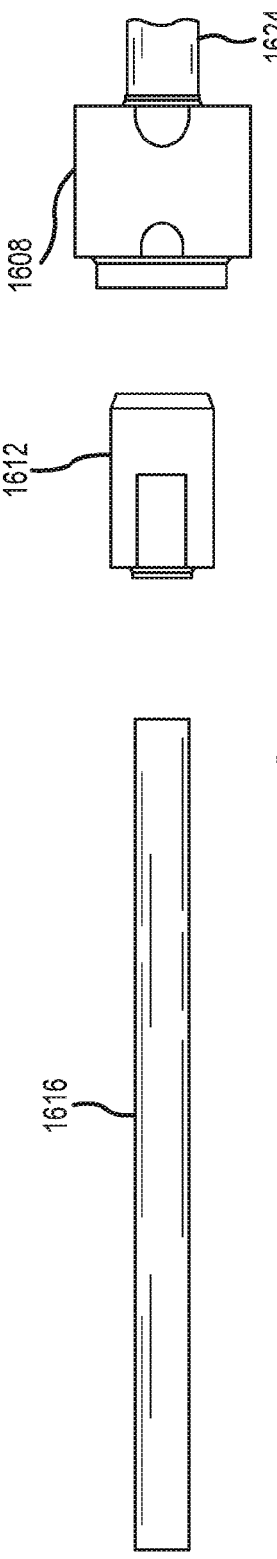

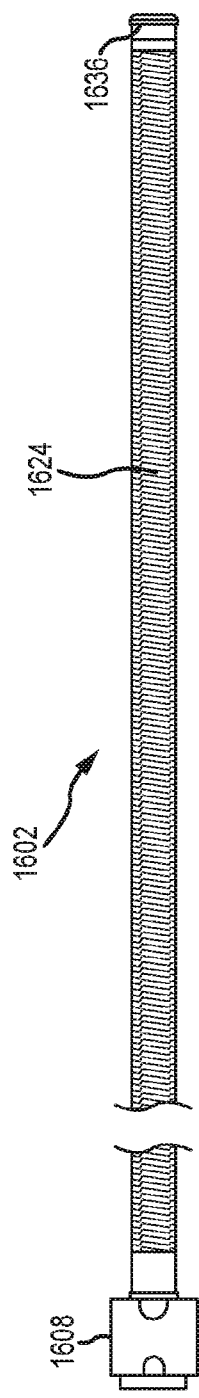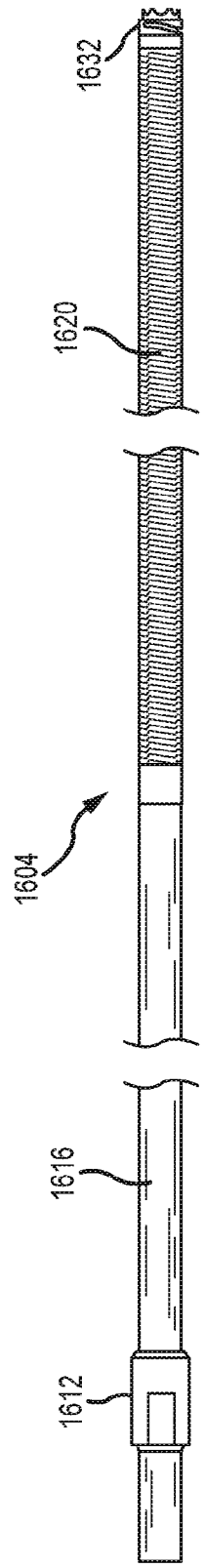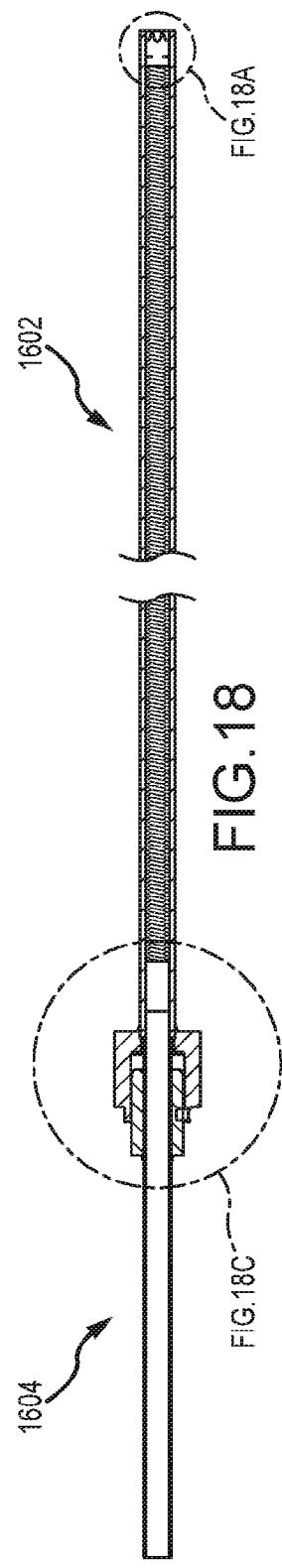

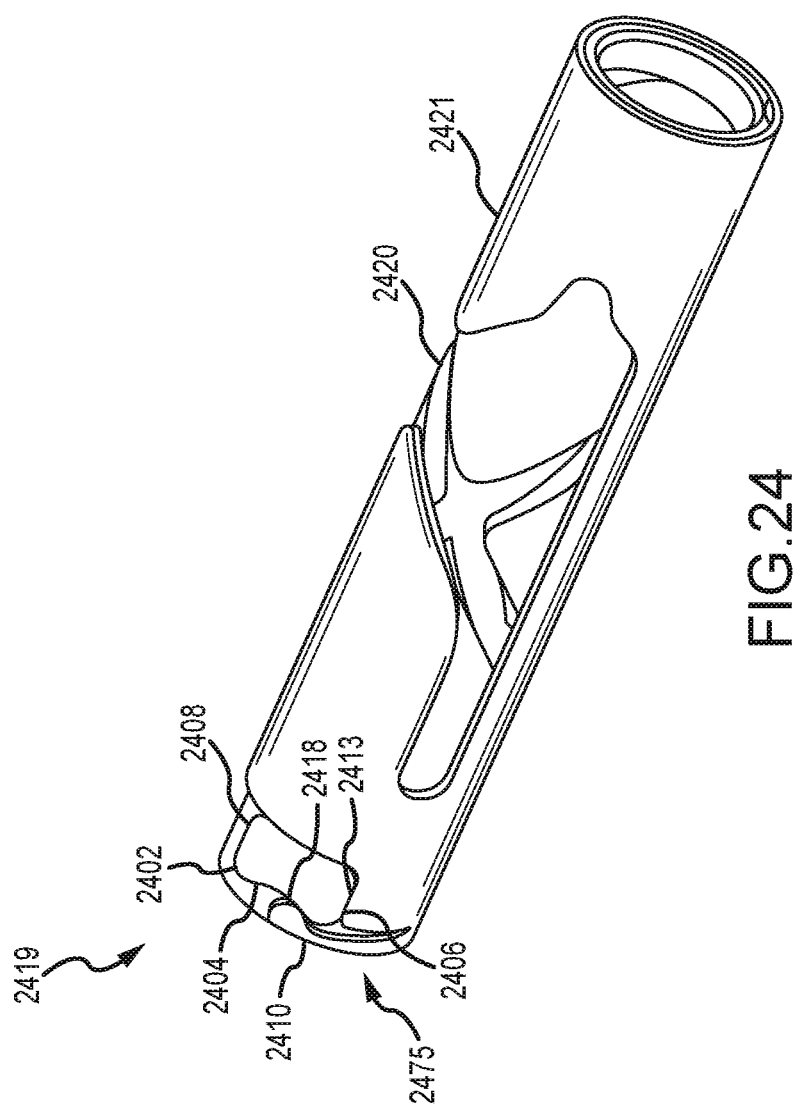

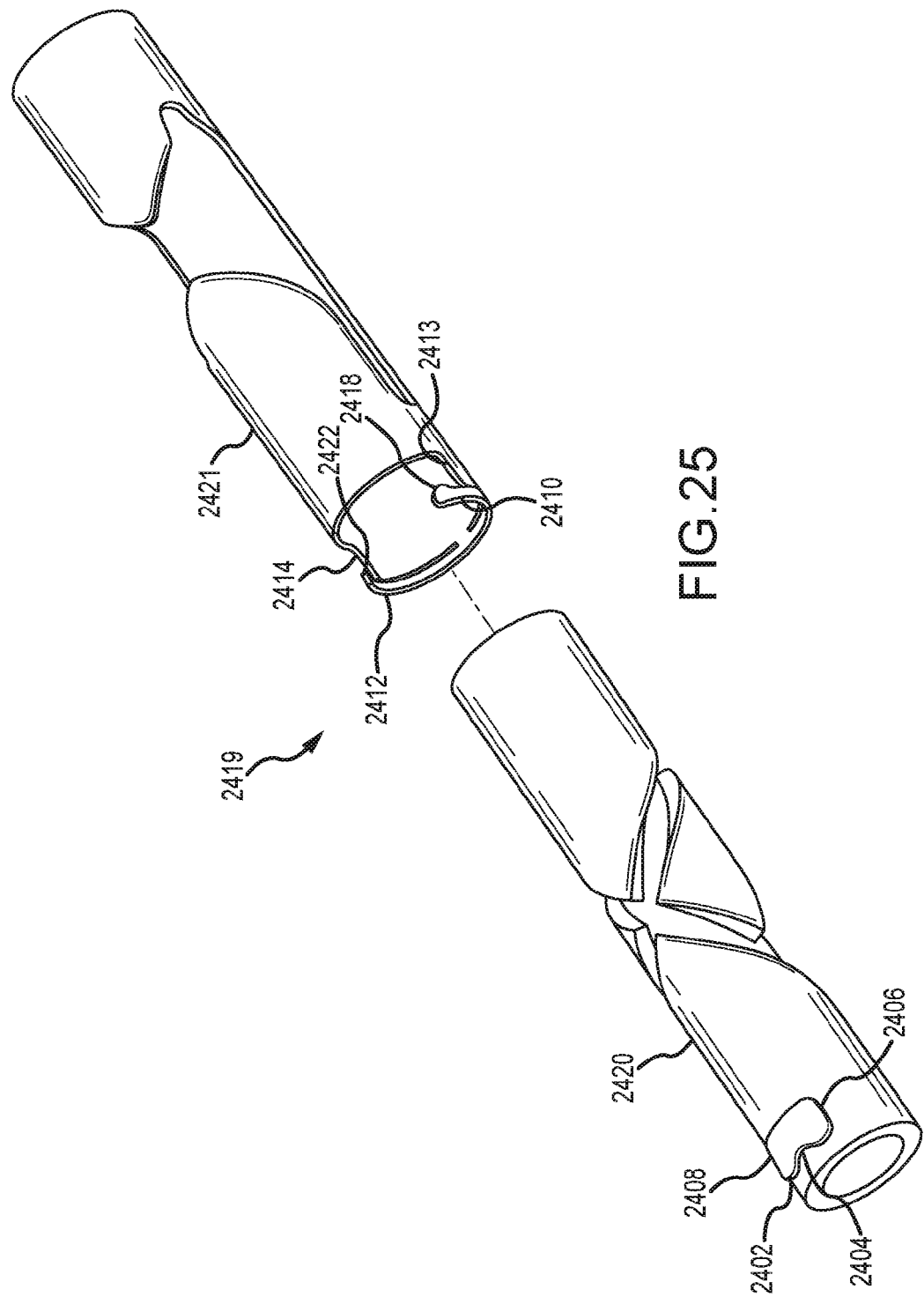

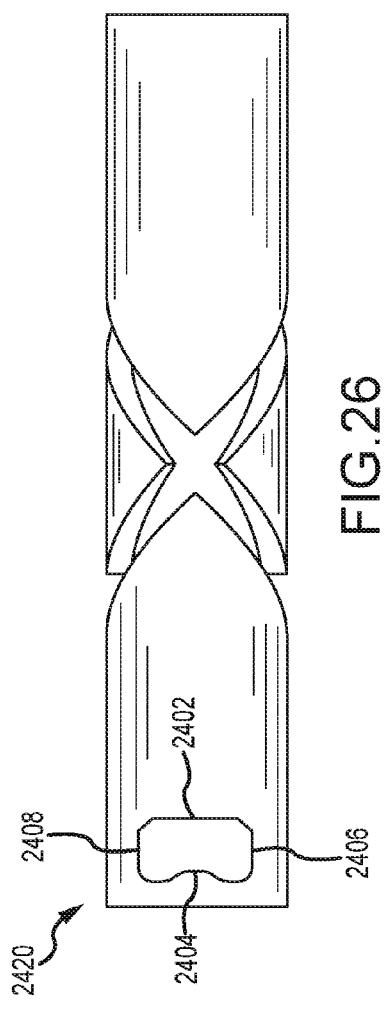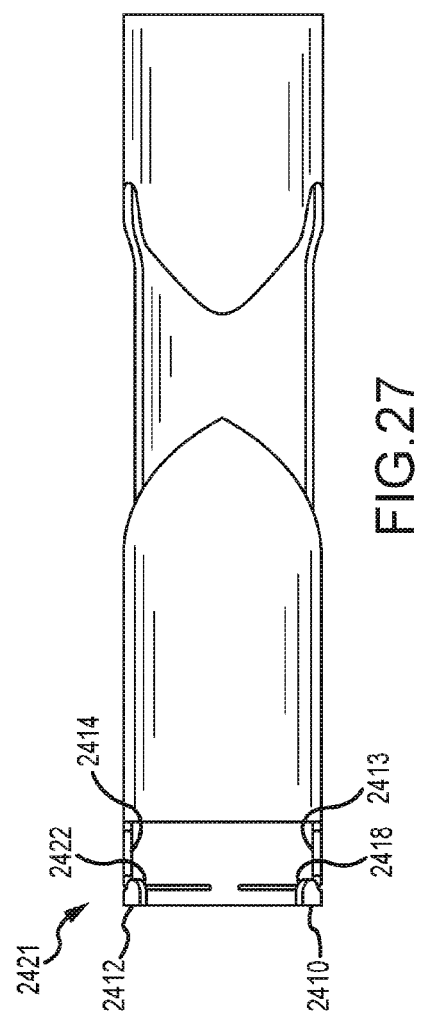

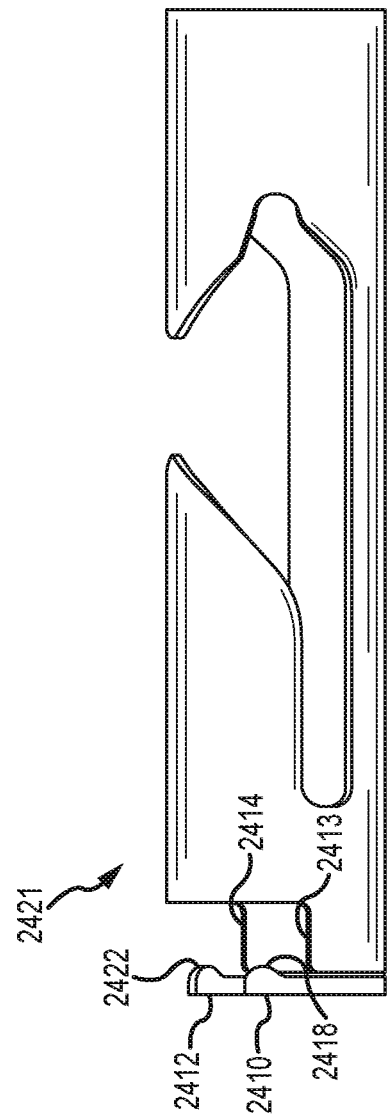

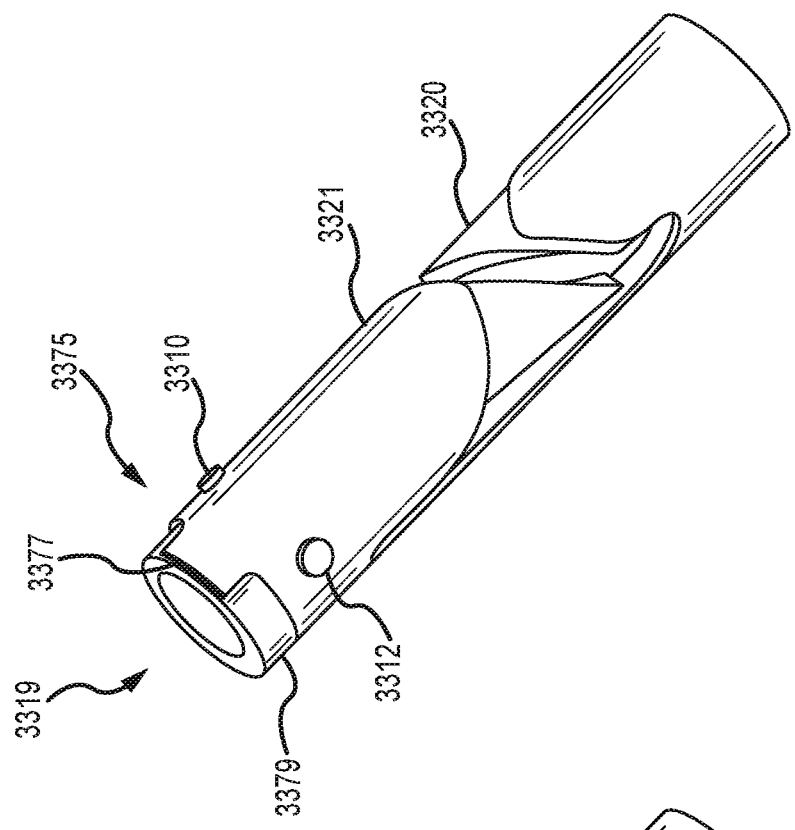
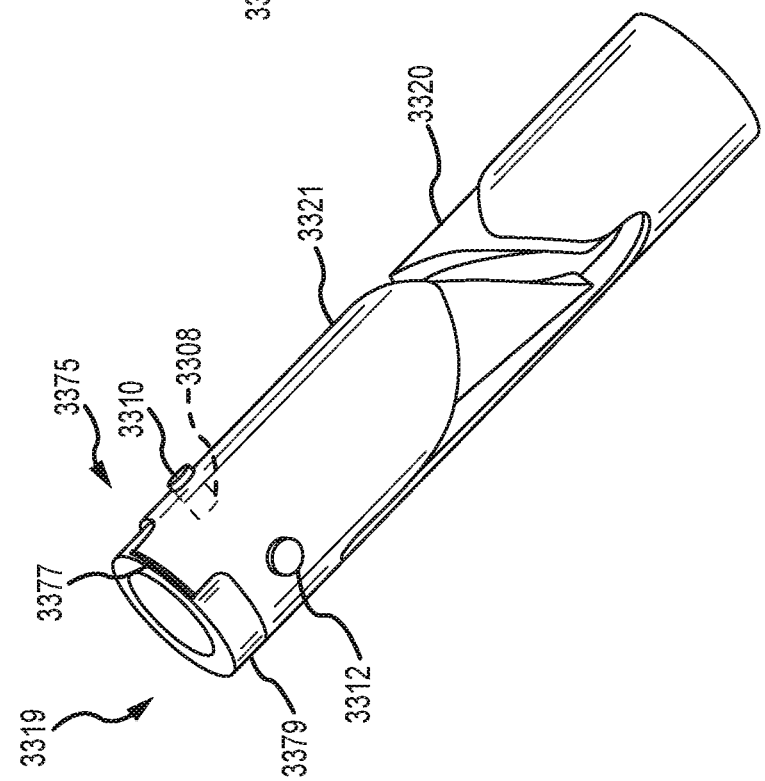

MEDICAL DEVICE FOR REMOVING AN IMPLANTED OBJECT

CROSS-REFERENCE TO RELATED APPLICATION

This application is a Continuation of U.S. application Ser. No. 14/627,950, filed Feb. 20, 2015 and entitled MEDICAL DEVICE FOR REMOVING AN IMPLANTED OBJECT, which is a Continuation-In-Part of International Application No. PCT/US2014/026496, filed Mar. 13, 2014 and entitled SURGICAL INSTRUMENT FOR REMOVING AN IMPLANTED OBJECT, which claims the benefit of and priority to, under 35 U.S.C. § 119(e), U.S. Provisional Application Ser. No. 61/793,597, filed Mar. 15, 2013, entitled SURGICAL INSTRUMENT FOR REMOVING AN IMPLANTED OBJECT. U.S. application Ser. No. 14/627,950 also claims the benefit of and priority to, under 35 U.S.C. § 119(e), U.S. Provisional Application Ser. No. 61/947,377, filed Mar. 3, 2014, entitled MEDICAL DEVICE FOR REMOVING AN IMPLANTED OBJECT, U.S. Provisional Application Ser. No. 62/058,790, filed Oct. 2, 2014, entitled MEDICAL DEVICE FOR REMOVING AN IMPLANTED OBJECT, and U.S. Provisional Application Ser. No. 62/113,865, filed Feb. 9, 2015, entitled MEDICAL DEVICE FOR REMOVING AN IMPLANTED OBJECT. The above applications are hereby incorporated by reference in their entireties for all that they teach and for all purposes.

FIELD OF THE DISCLOSURE

The present disclosure relates generally to devices, methods and systems for separating tissue in a patient's vascular system, and more specifically, to devices for separating tissue attached to implanted objects, such as leads, in a patient's vascular system and removing such objects.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe et al., which is hereby incorporated herein by reference in its entirety for all that it teaches and for all purposes.

A mechanical device to extract leads may include one or more a flexible tubes called a sheath that passes over the lead and/or the surrounding tissue. One of the sheaths may include a tip having a dilator, a separator and/or a cutting blade, such that upon advancement, the tip (and possibly the sheath cooperate to) dilates, separates and/or cuts to separate the scar tissue from other scar tissue including the scar tissue surrounding the lead. In some cases, the tip (and sheath) may also separate the tissue itself from the lead. Once the lead is separated from the surrounding tissue and/or the surrounding tissue is separated from the remaining scar tissue, the lead may be inserted into a hollow lumen of the sheath for removal and/or be removed from the patient's vasculature using some other mechanical devices, such as the mechanical traction device previously described in United States Patent Publication No. 2008/0154293 to Taylor, which is hereby incorporated herein by reference in its entirety for all that it teaches and for all purposes.

Some lead extraction devices include mechanical sheaths that have trigger mechanisms for extending the blade from the distal end of the sheath. An example of such devices and method used to extract leads is described and illustrated in U.S. Pat. No. 5,651,781 to Grace, which is hereby incorporated herein by reference in its entirety for all that it teaches and for all purposes. Another example of these device that has a trigger mechanism for extending the blade from the distal end of the sheath is described and illustrated in United States Patent Publication No. 2014/0277037 having application Ser. No. 13/834,405 filed Mar. 14, 2013, which is hereby incorporated herein by reference in its entirety for all that it teaches and for all purposes.

Controlling the amount of extension and retraction of the blade within a patient's vasculature may be critical, particularly when the sheath and blade negotiate tortuous paths that exist in certain vascular or physiological environments and/or when the blade is attempting to cut and/or separate tough surrounding tissue. Furthermore, in certain cases, using such mechanical devices for lead removal may require more meticulous control, such as when the leads are located in, and/or attached to a structurally-weak portion of the vasculature. For instance, typical leads in a human may pass through the innominate vein, past the superior vena cava ("SVC"), and into the right atrium of the heart. Tissue growth occurring along the SVC and other locations along the innominate vein may increase the risk and difficulty in extracting the leads from such locations, particularly when the vein(s)' walls are thin and the surrounding tissue is notably fibrous.

SUMMARY

Accordingly, there is a need for a device, method and/or system such as a surgical device that has the capability to precisely control the extension, retraction and rotation of a blade from within an outer sheath. For example, it may be desirable for the blade to rotate in one direction as the blade initially extends from and retracts within the outer sheath, then rotate in an opposite direction upon subsequent extension and retraction during the same actuation of the surgical device. The present disclosure discusses a surgical device that has a barrel cam cylinder in the handle assembly that imparts rotation of the blade and a separate cam mechanism in the tip of outer sheath assembly that imparts and controls the extension and retraction of the blade. The barrel cam cylinder and cam mechanism cooperate to cause the blade to rotate in one direction as it initially extends from and retracts in the outer sheath and to rotate in a second direction as it extends and retracts a second time. For each actuation of the handle, the blade rotates in one direction as it initially extends from and retracts into outer sheath and subsequently rotates in a second direction as it extends and retracts a second time. Alternating the direction of rotation in conjunction with the extension and retraction of the blade during rotation creates a slicing action in one direction for each extension and retraction of the blade, thereby minimizing the potential for the blade to become jammed in the surrounding tissue.

A device in accordance with this disclosure for removing an implanted object from a body vessel, may comprise a sheath assembly comprising an outer sheath assembly and an inner sheath assembly, and a pin, the outer sheath assembly comprising an outer sheath and an outer band, the outer band coupled to the pin, the inner sheath assembly comprising an inner sheath and a tip, wherein the tip has a cutting surface, the inner sheath comprising a proximal end and a distal end, wherein the distal end of the inner sheath is coupled to the tip, the tip comprising a cam slot for receipt of and cooperation with the pin, and a handle assembly comprising a trigger and a barrel cam cylinder, the trigger comprising a trigger pin, the barrel cam cylinder comprising a barrel cam cylinder slot for receipt and cooperation with the trigger pin, wherein the proximal end of the inner sheath is coupled to the barrel cam cylinder such that upon the trigger pin moving proximally in a longitudinal direction, the barrel cam cylinder rotates in both a clockwise direction and a counter clockwise direction, thereby causing the tip to rotate in both the clockwise direction and the counter clockwise direction while the tip moves longitudinally.

A device in accordance with this disclosure for removing an implanted object from a body vessel, may alternatively comprise a sheath assembly comprising an outer sheath assembly and an inner sheath assembly, and a pin, wherein the outer sheath assembly and the inner sheath assembly each comprise a proximal end and a distal end, wherein the distal end of the outer sheath assembly is coupled to the distal end of the inner sheath assembly by the pin, the inner sheath assembly comprising an inner sheath and a tip at its distal end, wherein the tip has a cutting surface, the tip comprising a slot for receipt of and cooperation with the pin, and a handle assembly comprising a trigger and a barrel cam cylinder, the trigger comprising a trigger pin, the barrel cam cylinder comprising a barrel cam cylinder slot for receipt and cooperation with the trigger pin, wherein the proximal end of the inner sheath is coupled to the barrel cam cylinder by the trigger pin such that upon the trigger pin moving proximally in a longitudinal direction, the barrel cam cylinder rotates in a first direction and a second direction, wherein the first direction is different than the second direction, wherein the tip moves longitudinally while the barrel cam cylinder rotates in the first direction, and wherein the tip moves longitudinally while the barrel cam cylinder rotates in the second direction.

There is a need for a device, method and/or system such as a surgical device that has the capability to precisely control the extension, retraction and rotation of a blade from within an outer sheath. For example, it may be desirable for the blade to rotate in one direction as the blade initially extends from and retracts within the outer sheath, then rotate in an opposite direction upon subsequent extension and retraction during the same actuation of the surgical device. The present disclosure discusses a surgical device that has a barrel cam cylinder in the handle assembly that imparts rotation of the blade and a separate cam mechanism in the tip of outer sheath assembly that imparts and controls the extension and retraction of the blade. The barrel cam cylinder and cam mechanism cooperate such that (1) upon a first actuation of the device, the barrel cam cylinder rotates in a first direction, thereby causing the blade to rotate in the first direction while the blade extends and retracts, and (2) upon a second actuation of the device, the barrel cam cylinder rotates in a second direction, thereby causing the blade to rotate in the second direction while the blade extends and retracts. Alternating the direction of rotation in conjunction with the extension and retraction of the blade during rotation creates a slicing action that minimizes the potential for the blade to become jammed in the surrounding tissue.

A device in accordance with this disclosure for removing an implanted object from a body vessel, may comprise a sheath assembly comprising an outer sheath assembly and an inner sheath assembly, and a pin, the outer sheath assembly comprising an outer sheath and an outer band, the outer band coupled to the pin, the inner sheath assembly comprising an inner sheath and a tip, wherein the tip has a cutting surface, the inner sheath comprising a proximal end and a distal end, wherein the distal end of the inner sheath is coupled to the tip, the tip comprising a cam slot for receipt of and cooperation with the pin, and a handle assembly comprising a trigger and a barrel cam cylinder, the trigger comprising a trigger pin, the barrel cam cylinder comprising a barrel cam cylinder slot for receipt and cooperation with the trigger pin, wherein the proximal end of the inner sheath is coupled to the barrel cam cylinder such that (1) upon a first actuation of the trigger to proximally move the trigger pin in a longitudinal direction, the barrel cam cylinder rotates in a first direction, thereby causing the tip to rotate in the first direction while the tip moves longitudinally; and (2) upon a second actuation of the trigger to proximally move the trigger pin in the longitudinal direction, the barrel cam cylinder rotates in a second direction, thereby causing the tip to rotate in the second direction while the tip moves longitudinally.

A device in accordance with this disclosure for removing an implanted object from a body vessel, may comprise a sheath comprising a proximal end and a distal end, a tip coupled to the distal end of the sheath, wherein the tip has a cutting surface, a handle assembly rotatably carrying the sheath, the handle assembly comprising a trigger comprising a trigger pin; and a barrel cam assembly comprising a barrel cam cylinder comprising a barrel cam cylinder slot for receipt and cooperation with the trigger pin, the barrel cam cylinder slot comprising a first slot portion and a second slot portion; a follower guide rotatably carried by the barrel cam cylinder; wherein upon a first actuation of the trigger to proximally move the trigger pin in a longitudinal direction, the follower guide urges the trigger pin to traverse the first slot portion, thereby causing the barrel cam cylinder and the tip to rotate in the first direction; and wherein upon a second actuation of the trigger to proximally move the trigger pin in a longitudinal direction, the follower guide urges the trigger pin to traverse the second slot portion, thereby causing the barrel cam cylinder and the tip to rotate in the second direction.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "barrel cam cylinder", which is sometimes referred to as a "cylindrical cam", typically includes a groove (slot or channel) cut into the surface of a cylinder, and a follower, such as a pin, which rides in the groove. A barrel cam cylinder is generally used to convert rotational motion to linear motion parallel to the rotational axis of the cylinder or to convert linear motion, parallel to the axis of the cylinder, to rotational motion. For the purposes of this disclosure, unless otherwise specified, the barrel cam cylinder may refer to the cylinder and the follower.

A "lead" is a conductive structure, typically an electrically insulated coiled wire. The electrically conductive material may be any conductive material, with metals and intermetallic alloys common. The outer sheath of insulated material is biocompatible and bio stable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

A "serration" or "serrated edge" or "serrated blade" or other variations, as used herein, shall mean the configuration of a cutting surface having a notched edge or saw-like teeth. The notched edges create a plurality of smaller points that contact (and therefore less contact area with) the material being cut in comparison to an un-notched blade. Additionally, the pressure applied by each serrated point of contact is relatively greater and the points of contact are at a sharper angle to the material being cut. One example of a serrated blade may include one notch adjacent to and abutting another notch such that there is very little, if any, blade between such notches, thereby creating points of contact. There are multiple variations and/or features of serrations. For example, one type of serrated feature is referred to as a "crown." As used herein, a serrated blade, or other variation, in the shape of a "crown," shall mean a blade comprising a plurality of notches and adjacent un-notched areas such that the combination of notched and un-notched areas resembles a crown for a royal member (e.g., king, queen, etc.), particularly when the blade is circular. A further type of "crown" includes a "hook crown." As used herein, a serrated blade, or other variation, in the shape of a "hook crown," shall mean a blade comprising of a plurality of notches and adjacent un-notched areas, wherein the length of the un-notched areas ascend to the next adjacent point at an angle to increase the slicing action in one rotary direction and the notches are created at an angle to create a hook feature at the points to promote engagement with the tissue at the hook-shaped point.

A "surgical implant" or "implanted object" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

"Vasculature" or "vascular system" is any part of the circulatory system, which includes the heart, blood, and blood vessels such as arteries, veins and capillaries.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4A is an internal view of an embodiment of a handle assembly of the surgical device illustrated in FIG. 2;

FIG. 4D is a cross-sectional view of an embodiment of the barrel cam cylinder illustrated in FIG. 4C;

FIG. 4E is an end view of an embodiment of the barrel cam cylinder illustrated in FIG. 4C;

FIG. 4F is an enlarged perspective view of an embodiment of a spool for the handle assembly illustrated in FIG. 4A;

FIG. 6 is an elevation view of an embodiment of the sheath assembly;

FIG. 6A is a break-away, elevation view of an embodiment of the distal end of the sheath assembly illustrated in FIG. 6;

FIG. 6B is a break-away, elevation view of an embodiment of the proximal end of the sheath assembly illustrated in FIG. 6;

FIG. 7A is an elevation view of an embodiment of the outer sheath assembly;

FIG. 7B is an elevation view of an embodiment of the inner sheath assembly;

FIG. 8 is a cross-sectional view of an embodiment of the sheath assembly illustrated in FIG. 6;

FIG. 8A is an enlarged cross-sectional view of the distal end of the inner sheath assembly located within the outer sheath assembly illustrated in FIG. 8, wherein the blade is retracted and located within the outer sheath assembly;

FIG. 8A' is an enlarged cross-sectional view of the distal end of the inner sheath assembly located within the outer sheath assembly illustrated in FIG. 8, wherein the blade is extended and located outside the outer sheath assembly;

FIG. 8B is a distal end view of the inner sheath assembly located within the outer sheath assembly illustrated in FIG. 8;

FIG. 8C is an enlarged cross-sectional view of the inner key of the inner sheath assembly located within the outer key of the outer sheath assembly illustrated in FIG. 8;

FIG. 15A is an internal view of an embodiment of a handle assembly of the surgical device illustrated in FIG. 13;

FIG. 16 is an elevation view of an embodiment of the sheath assembly;

FIG. 16A is a break-away, elevation view of an embodiment of the distal end of the sheath assembly illustrated in FIG. 16;

FIG. 16B is a break-away, elevation view of an embodiment of the proximal end of the sheath assembly illustrated in FIG. 16;

FIG. 17A is an elevation view of an embodiment of the outer sheath assembly;

FIG. 17B is an elevation view of an embodiment of the inner sheath assembly;

FIG. 18 is a cross-sectional view of an embodiment of the sheath assembly illustrated in FIG. 16;

FIG. 18A' is an enlarged cross-sectional view of the distal end of the inner sheath assembly located within the outer sheath assembly illustrated in FIG. 18, wherein the blade is extended and located outside the outer sheath assembly;

FIG. 24 is a perspective view of an embodiment of the barrel cam assembly for a surgical device;

FIG. 25 is an exploded perspective view of the barrel cam assembly of FIG. 24;

FIG. 26 is a side view of a barrel cam cylinder of the barrel cam assembly of FIG. 24;

FIG. 27 is a side view of a follower guide of the barrel cam assembly of FIG. 24;

FIG. 28 is another side view of the follower guide of FIG. 24;

FIG. 33 is a perspective view of an embodiment of the barrel cam assembly for a surgical device; hidden features are shown in light gray lines;

FIG. 34 is another perspective view of the barrel cam assembly of FIG. 33;

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
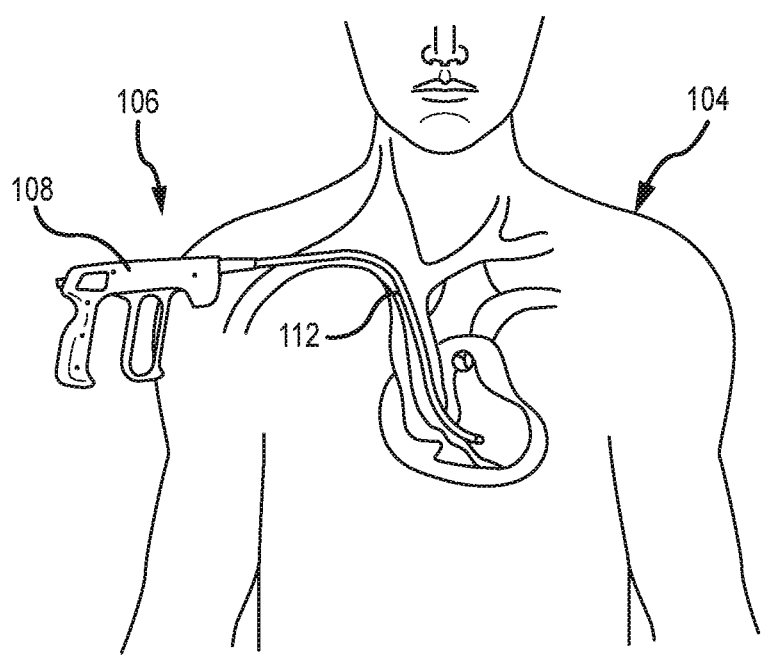
FIG. 1 is a perspective view of a human having a pacemaker lead located in the venous system and a terminating electrode anchored to the ventricular heart chamber, with an embodiment of a surgical device being shown inserted into the body and partly advanced over the lead.

Embodiments according to this disclosure provide a surgical device that includes a sheath assembly, which can be deployed safely within a vascular system of a patient and separate implanted objects, such as leads, from a patient's vasculature system. FIG. 1 depicts a surgical device 106 having a sheath assembly 112 inserted within an exemplary patient 104. The sheath assembly 112 surrounds an implanted lead (not shown) running along the left innominate vein past the SVC and connected into, or about, the right ventricle of the heart. Upon surrounding the lead with the sheath assembly 112, the user of the surgical device 106 may actuate the handle assembly 108, thereby rotating and extending a cutting blade (not shown) beyond the distal end of the sheath assembly 112 to dilate, separate and/or cut the tissue surrounding the lead within the patient's SVC.

The cutting blade may extend from and retract into the sheath multiple times upon actuation of the handle assembly according to the profile of the cam slot in the cutting tip disclosed below. The cutting blade may also rotate in both a clockwise and counter-clockwise direction per the profile of the cam slot in the barrel cam cylinder discussed below. When the clinician releases the handle assembly, the cutting blade is ensured to remain or return within the sheath assembly 112, thereby allowing the clinician to force and advance the distal portion of the sheath assembly against additional uncut tissue. The clinician repeats the actuation step, thereby causing the cutting blade to re-appear and extend beyond the distal end of the sheath assembly 112 to cut the adjacent tissue. Each time actuation occurs, the proximal portion of the implanted lead and/or surrounding tissue enters further into a hollow passageway within the sheath assembly 112. This process is again repeated until the implanted lead and/or surrounding tissue is completely or substantially dilated, separated, and/or cut from the tissue attached to the SVC. At that time, the implanted lead may safely be removed from the patient's SVC.

Figure 2:
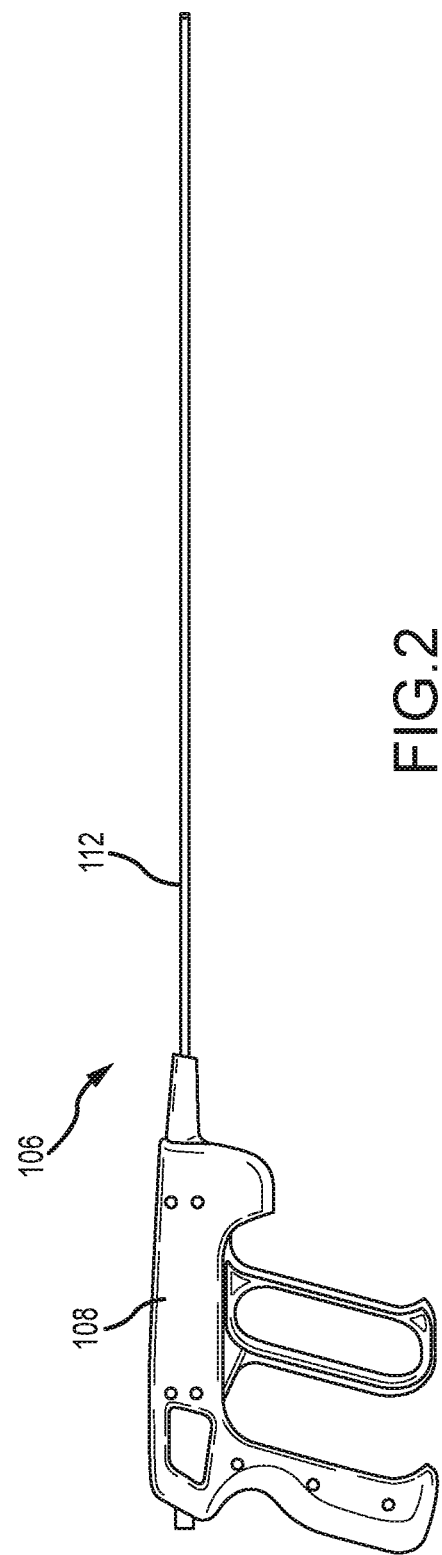
FIG. 2 is an elevation view of an embodiment of a surgical device.

With reference to FIG. 2, an exemplary surgical device 106 is depicted. The surgical device 106 includes a handle assembly 108 and a flexible sheath assembly 112. The flexible sheath assembly 112, which is discussed in more detail below, generally includes a flexible inner sheath assembly (not shown) located within a flexible outer sheath assembly. It may be preferable for the outer sheath to remain stationary while the inner sheath is capable of moving (e.g., rotating and extending) with respect to the outer sheath. The inner sheath and outer sheath can both be flexible, rigid or a combination thereof.

With reference to FIG. 4A, an exemplary handle assembly is depicted. The handle assembly 108 may include some or all of the following components: a handle frame 404, a trigger 408, a spring assembly 412, a strain relief component 416, a barrel cam cylinder 420, a bushing 424 and an end cap 427. The handle frame 404 may be constructed of a singular component or multiple component, such as two halves as illustrated in FIG. 4A.

Figure 4B:
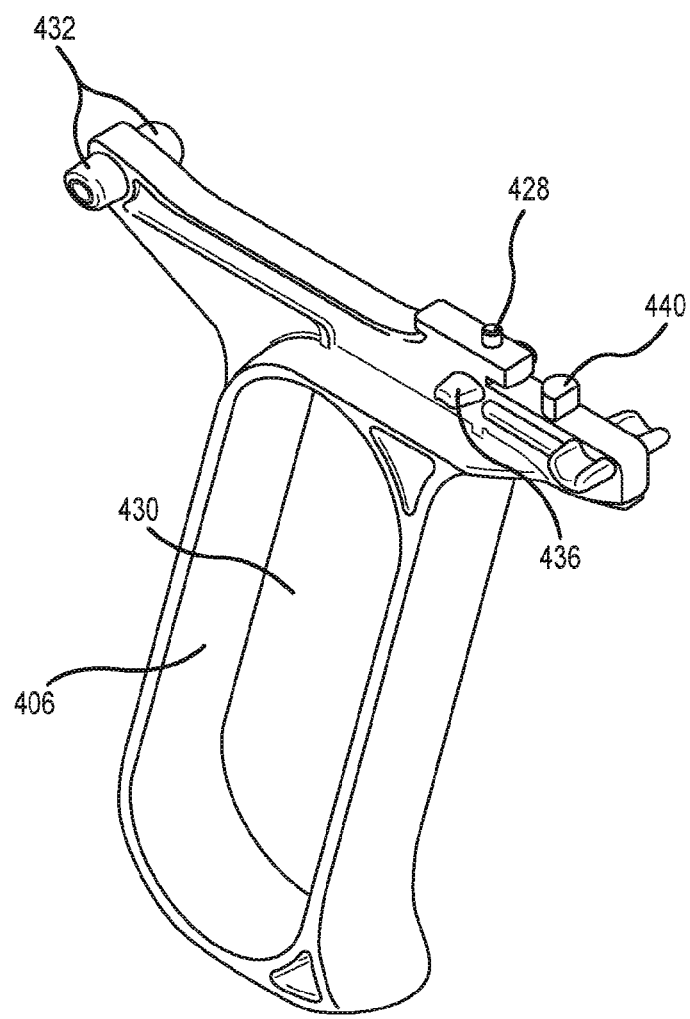
FIG. 4B is a perspective view of an embodiment of a trigger for the handle assembly illustrated in FIG. 4A.

Referring to FIG. 4B, an exemplary trigger 408 is illustrated. The trigger 408 depicted in FIG. 4A includes one opening 430 into which a clinician can insert his/her fingers. A trigger, however, may have more than one opening. Additionally, a trigger may also be comprised of a straight or non-linear member without any openings. Furthermore, a trigger may be in the shape of a button capable of being depressed. As long as the trigger, either alone or in conjunction with the handle frame, is ergonomically correct and comfortable for the clinician, the trigger may have a variety of sizes and shapes.

The trigger 408 illustrated in FIG. 4B includes a trigger pin 428 that extends vertically from the top of the trigger 408. The trigger pin 428 may be formed of a metal, such as a copper alloy (for example, brass or bronze, particularly C 630 nickel aluminum bronze), and may include a frusto-conically shaped end to facilitate insertion into the handle frame 404. The trigger pin 428, which cooperates with the groove in the barrel cam cylinder 420, acts as a follower for the barrel cam. The trigger 408 also includes a pair of sliders 432 protruding laterally from the proximal end of the trigger 408 and a pair of sliders 436 protruding laterally from the distal end of the trigger 408. When the trigger 408 is located within the handle assembly 108, the sliders 432, 436 sit and slide in corresponding grooves within the handle frame 404. The trigger 408 also includes a post 440 extending vertically from the top of trigger 408, and preferably from the distal end of the top of the trigger 408. The post 440 connects to spring assembly 412.

The handle assembly 108, including the trigger 408 and barrel cam cylinder 420 discussed above is an example of a mechanical actuation means to rotate the inner sheath assembly. In an alternate embodiment, the actuation means may comprise electromechanical components. For example, the actuation means may comprise an electric motor (not shown) having a driven shaft that is directly or indirectly coupled to the inner sheath, the barrel cam cylinder, the trigger pin, and/or any combination thereof. The motor's shaft may be indirectly coupled to the inner sheath by one or more gears discussed hereinbefore. The motor may be controlled by a switch, thereby causing the inner sheath to rotate in a clockwise and/or a counter-clockwise direction upon actuating a switch that may also act as the trigger. The electric motor may be either a direct current (DC) motor or an alternating current (AC) motor. Accordingly, the motor may be powered by a DC source, such as a battery, or an AC source, such as a conventional power cord. Additionally, those skilled in the art will appreciate that there are numerous other ways in which a surgical device comprising a rotatable sheath may be actuated and driven.

As mentioned above, the handle assembly 108 may include a strain relief component 416. The strain relief component 416, as illustrated in FIG. 4A, is attached to the distal end of the handle frame 404 and tapers from its proximal end toward its distal end. The strain relief component 416 also has a lumen passing through it, thereby allowing the sheath assembly 112 to extend there through and into the handle assembly 108. The strain relief component 416 may be constructed of a flexible material such as, Santoprene™ thermoplastic vulcanizate produced by ExxonMobil. The material from which the strain relief component is made and the shape of the strain relief component provide a flexural modulus to protect the flexible shaft as it extends the rigid handle. The lumen of the strain relief may also contain a counter bore that enables ancillary outer sheaths to be docked during device preparations.

Figure 4C:
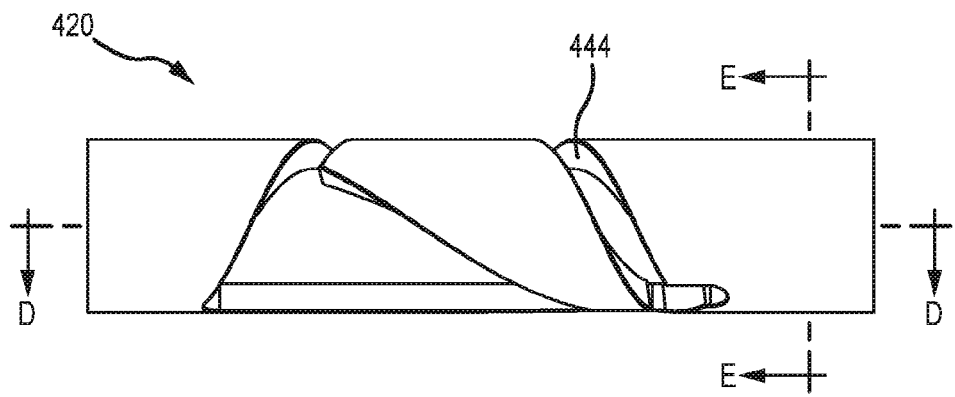
FIG. 4C is an elevation view of an embodiment of the barrel cam cylinder for the handle assembly illustrated in FIG. 4A.
Figure 5A:
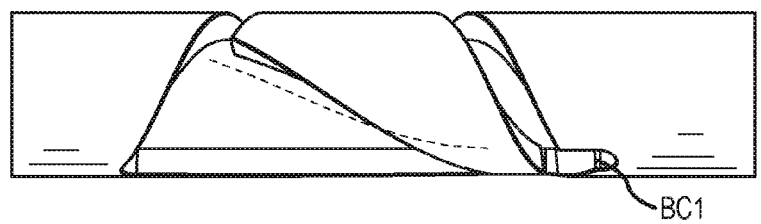
FIG. 5A is an elevation view of the barrel cam cylinder illustrated in FIG. 4C in its home position.
Figure 5B:
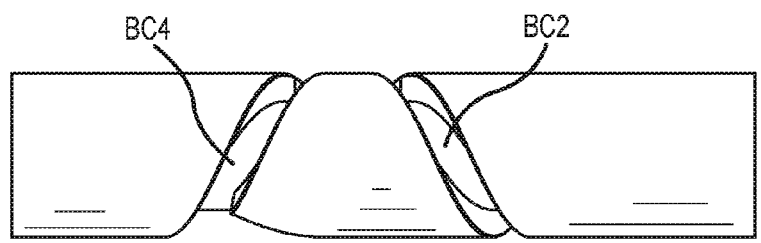
FIG. 5B is an elevation view of the barrel cam cylinder illustrated in FIG. 4C upon being rotated to about 136.5 degrees in clockwise direction and/or counter-clockwise direction.
Figure 5C:
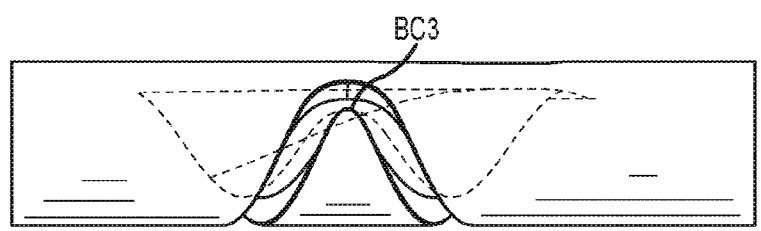
FIG. 5C is an elevation view of the barrel cam cylinder illustrated in FIG. 4C upon being rotated to about 273.1 degrees in clockwise direction.
Figure 5D:
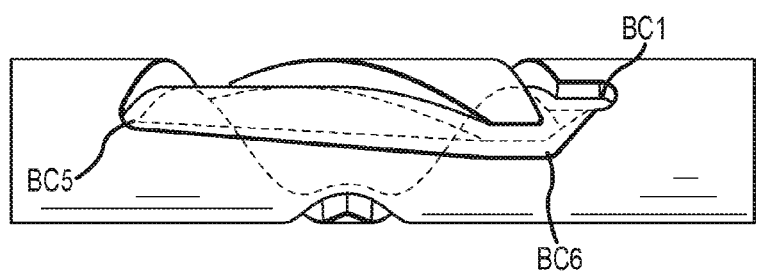
FIG. 5D is an elevation view of the barrel cam cylinder illustrated in FIG. 4C upon being rotated to 307.6 degrees in a counter-clockwise direction and toward its home position.
Figure 5E:
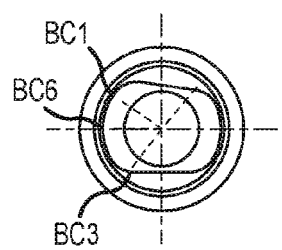
FIG. 5E is an end view of the barrel cam cylinder illustrated in FIG. 4E including an indication of the amount of angular rotation for the cam cutter at each of the barrel cam cylinder positions illustrated in FIGS. 5A, 5B, 5C and 5D.

Referring to FIGS. 4C, 4D and 4E, there is depicted an elevation view, cross-sectional view and end view of the barrel cam cylinder 420, respectively. As illustrated in FIGS. 4C and 4D, the barrel cam cylinder 420 has an exterior surface comprising a cam slot (or channel) 444 that cooperates with the trigger pin 428 to create the barrel cam. The cam slot 444 may create a two dimensional linear and/or non-linear cam profile, which is discussed in further detail below. The barrel cam cylinder 420 has a proximal end 448 and a distal end 452 through which a lumen 456 extends.

FIG. 4E illustrates the end view of the distal end 452 of the barrel cam cylinder 420. The distal end 452 of the lumen 456 of the barrel cam cylinder 420 is designed to mate with exterior of the proximal end of the inner key 612, which is discussed in further detail below. The cross section of the distal end 452 of the lumen 456 of the barrel cam cylinder 420 is preferably non-circular. For example, one embodiment of a non-circular lumen includes two chamfered sides 464, wherein one chamfered side 464 is not offset, and the other chamfered side 464 is offset (e.g., about 8 degrees). Because the distal end of the barrel cam cylinder 420 is designed to mate with exterior of the proximal end of the inner key 612 and transfer torque from the barrel cam cylinder 420 to the inner sheath assembly via the inner key 612, the cross section of the exterior of proximal end of the inner key 612 will have a complimentary profile of the lumen 456. Although the cross sectional shape of the non-circular lumen is described as having two chamfered sides 464, the disclosure shall not be limited to such shape and may include alternative non-circular shapes, such as a square, rectangle, D-shape, triangle, rhombus, trapezoid, pentagon, hexagon, octagon, parallelogram, ellipse, etc. Alternatively, the inner key could couple to the outside of the barrel cam cylinder.

The proximal end of the barrel cam cylinder 420 mates with the bushing 424. Specifically, the exterior, distal end of the bushing 424 is located within the proximal end of the lumen 456. Both the exterior, distal end of the bushing 424 and the proximal end of the lumen 456 are circularly shaped, thereby allowing the bushing 424 and the barrel cam cylinder 420 to rotate with respect to one another. The proximal end of the exterior of the bushing 424, however, is located within a groove within the handle frame 404, thereby preventing the bushing 424 and the barrel cam cylinder 420 from moving longitudinally within the handle assembly 108.

Referring to FIG. 4F, an exemplary spring assembly 412 is depicted. The spring assembly 412 includes a constant force spring 472 and a spool 474. One end of the constant force spring 472 is connected to the spool 474, and the other end of the constant force spring 472 is connected to the post 440 extending from the trigger 408. As a clinician pulls the trigger 408 proximally, the sliders 432, 436 travel and slide in the grooves within the handle frame 404, thereby preventing the trigger 408 from moving vertically within the handle assembly 108 and only allowing the trigger 408 to move along the longitudinal axis of the surgical device 106 from its distal end toward its proximal end and/or vice versa. As the trigger 408 moves proximally, the constant force spring 472 uncoils, thereby creating tension and a distally directed force. Accordingly, when the trigger 408 is released by the clinician, the constant force spring 472 recoils and pulls the trigger 408 back towards its original and most distal position.

Referring to FIG. 6, there is depicted an elevation view of an embodiment of an assembled sheath assembly 112 of the present disclosure. The sheath assembly 112 includes an inner sheath assembly and an outer sheath assembly. Referring to FIG. 6A, which illustrates an exploded view of the distal end of the sheath assembly 112, and referring to FIG. 6B, which is an exploded illustration of the proximal end and central portion of the sheath assembly 112, the sheath assembly 112 may include may include some or all of the following components: an outer band 636; a guide pin 640; a cutting tip 632; a flexible inner sheath 620; a flexible outer sheath 624; an outer jacket 628; an inner key 612; an outer key 608; and a rigid inner tube 616.

Referring to FIG. 7A, there is depicted an embodiment of the outer sheath assembly 602 of the present disclosure. The outer sheath assembly 602 includes an outer band 636 located at and attached to the distal end of an elongated flexible outer sheath 624, and an outer key 608 located at and attached to the proximal end of the flexible outer sheath 624. The outer band 636 may be attached to the distal end of a flexible outer sheath 624 via a weld, an adhesive, a press-fitting technique, an interlock such as a barbed joint or other known means of attachment. All such attachment techniques within the knowledge of one skilled in the art are considered within the scope of this disclosure. Similarly, the outer key 608 may be attached to the proximal end of the flexible outer sheath 624 via a weld, an adhesive, a press-fitting technique, interlock such as a barbed joint, or other known means of attachment. Although it is not shown on FIG. 7A, the outer sheath assembly may also include a flexible outer jacket 628 that covers the outer sheath 624 and abuts the outer band 636, thereby providing the outer sheath assembly with a relatively smooth, continuous and uninterrupted exterior profile. The flexible jacket also contains the egress of blood from the system.

Referring to FIG. 7B, there is depicted an embodiment of the inner sheath assembly 604 of the present disclosure. The inner sheath assembly 604 includes a cutting tip 632, a flexible inner sheath 620, an inner key 612, and a rigid inner tube 616. The proximal end of the cutting tip 632 is attached to the distal end of a flexible inner sheath 620; the distal end of an inner tube 616 is attached to the proximal end of the flexible inner sheath 620; and an inner key 612 is attached to the proximal end of the inner tube 616. The means of attaching these components may include a weld, an adhesive, a press-fitting technique, or other known means of attachment. As will be discussed below, the guide pin 640 couples the outer band 636 with the cutting tip 632, and the guide pin 640 may be includes with either the inner sheath assembly 604 or the outer sheath assembly 602.

It may be preferable for a portion of either the inner sheath 620 and/or the outer sheath 624 to be rigid and a portion of the outer sheath to be flexible. Both the rigid portion and the flexible portion may be constructed of materials suitable for insertion into the human body. For example, the rigid portion may be constructed of stainless steel, and the flexible portion may be constructed of a flexible polymer such as polytetrafluoroethylene or thermoplastic elastomers. Assuming that both a rigid portion and a flexible portion are used, they will form a unitary inner sheath and/or outer sheath. As depicted in FIG. 7B, the rigid inner tube 616 is not only attached to the inner key 612, the rigid tube 616 also is inserted through the inner key 612 and extends from both the proximal end and distal end of the inner key 612. The attachment and extension of the rigid tube 616 to the inner key 612 allows for an increased amount of torque that can be transferred from the barrel cam to the rigid tube 616 via the inner key 612 and eventually to the cutting tip 632 via the inner sheath assembly 604. The extension of the rigid tube through the handle provides an access point for introduction of other medical devices. The extension also provides a means of controlling blood egress after the lead has been extracted.

It may be preferable that at least a portion of the outer sheath 624 and the inner sheath 620 be generally flexible in order to accept, accommodate and navigate the patient's vasculature system. In addition to being flexible, the inner sheath 620 may also have a high degree of stiffness in order to receive the torque transferred from the barrel cam cylinder/inner key and transfer sufficient torque to the cutting tip 632 discussed in more detail below. The inner sheath 620 (and/or the outer sheath 624) may be formed of a polymer extrusion, braided reinforced polymer extrusion, coils, bi-coils, tri-coils, laser cut metal tubing and any combination of the above. The inner sheath (and/or the outer sheath 624) may be a unitary structure comprised of multiple portions.

Referring to FIG. 8, there is depicted a cross-sectional view of an embodiment of the sheath assembly 112 comprising the inner sheath assembly 604 located within the outer sheath assembly 602. Referring to FIG. 8C, there is depicted an enlarged view of the inner key 612 of the inner sheath assembly 604 located within the outer key 608 of the outer sheath assembly 602. As discussed above, the exterior of the inner key 612 is designed to mate with lumen 456 of the distal end of the barrel cam cylinder 420. Accordingly, the cross section of the exterior of proximal end of the inner key 612 will have a profile complimentary to the distal end of the lumen 456 within the barrel cam cylinder 420. For example, assuming the cross section of the distal end 452 of the lumen 456 of the barrel cam cylinder 420 is non-circular and has two chamfered sides, wherein one chamfered side is not offset, and the other chamfered side is offset (e.g., about 8 degrees), then the exterior of the proximal end of the inner key 612 will also have a non-circular profile with two chamfered sides, wherein one chamfered side is not offset, and the other chamfered side is offset (e.g., about 8 degrees). The inner key 612 and outer key 608 provide means for rotationally coupling. The inner key 612 is a means for rotationally coupling the inner sheath assembly 604 to the barrel cam, and the outer key is a means for rotationally coupling the outer shaft assembly to the handle. The inner key 612 and outer key 608 provide journal bearing for the other key.

As further illustrated in FIG. 8C, the inner key 612 is able to rotate freely within the outer key 608 due, at least in part, to the distal end of the exterior of the inner key 612 having a circular cross section that mates with a circular cross section of the proximal end of a lumen within the outer key 608. Additionally, because the inner key 612 and outer key 608 are loosely coupled, the inner key 612 and outer key 608 are able to move longitudinally with respect to one another. For instance, supposing the outer key 608 is fixed such that it neither rotates nor moves longitudinally, the inner key 612 is able to both rotate and travel longitudinally within the outer key 608. Accordingly, as the barrel cam cylinder 420 rotates, the inner key 612 will rotate within the outer key 608, and the inner sheath assembly 604 will rotate within the outer sheath assembly 602, including the rotation of the cutting tip 632 within the outer band 636. And the cam slot profile in the cutting tip 632 controls the longitudinal movement of the inner sheath assembly 604 within the outer sheath assembly 602, including the longitudinal movement of the inner key 612 relative to the outer key 608 and the longitudinal movement of the cutting tip 632 relative to the outer band 636.

Continuing to refer to FIG. 8C, the lumen within the outer key 608 is larger toward its proximal end and smaller toward its distal end because there is a step down or an abutment in the lumen as it progresses from the proximal end to the distal end. Due to the transition from a larger lumen to a smaller lumen within the outer key 608, there is depicted an adjustable gap 610 between the distal end of the inner key 612 and the abutment within the distal end of the larger lumen in the outer key 608. This gap increases, decreases and/or remains the same according to the cam slot profile of the cutting tip 632. The abutment in the outer key 608 insures that the inner key 612 will only travel a limited longitudinal distance within the outer key 608, thereby limiting the inner sheath assembly 604 potential longitudinal movement within the outer sheath assembly 602, including limiting the longitudinal movement of the cutting tip 632 relative to the outer band 636 in the distal direction.

Referring to FIG. 8A, there is depicted an enlarged cross-sectional view of the distal end of the sheath assembly 112 with the inner sheath assembly 604 coupled with the outer sheath assembly 602 via guide pin 640, wherein the blade 822 of the cutting tip 632 is in a retracted position and located within the outer sheath assembly 602. As discussed above, the distal end of the outer sheath assembly 602 includes an outer band 636, which may be constructed of a biocompatible metal, such as stainless steel, and polished so that it is generally smooth and evenly rounded at its most distal point, thereby allowing it to act as a dilator when pressed and forced against tissue. The distal end 822 of cutting tip 632 includes a cutting surface capable of cutting tissue. The inner sheath assembly 604 is coupled to the outer sheath assembly 602 through the cutting tip 632 and the outer band 636, respectively, via guide pin 640. One end of the guide pin 640 is fixed within the outer band 636, and the other end of the guide pin 640 is located within the cam slot 814 of the cutting tip 632. As the inner sheath 620 rotates, upon actuation of the trigger assembly discussed above, the cutting tip 632 also rotates because the inner sheath 620 is fixedly attached to the cutting tip 632. As the cutting tip 632 rotates, the cutting tip 632 may also extend distally in the direction of the arrow (→) according to the profile of the cam slot 814 as depicted in FIG. 8A'. As the cutting tip 632 extends distally and rotates, the guide pin 640 and the outer sheath assembly 602, particularly the outer band 636, remain stationary. Thus, as the cutting tip 632 extends distally (and potentially retracts proximally according to the cam slot profile) and rotates, the cutting surface at the distal end 822 of the cutting tip 632 is able to perform a slicing action against the tissue and cut it.

Again, FIG. 8A depicts the cutting tip 632 within a retracted (and potentially un-actuated) position because the cutting tip 632 is in a proximal position. Stated differently, the distal end 822 of the cutting tip 632 of FIG. 8A is located within the interior of the outer sheath assembly 602, particularly the outer band 636, and does not extend beyond the distal end of the outer band 636. With reference to FIG. 8A', the cutting tip 632 is depicted in an extended (and actuated) position because the cutting tip 632 is extending beyond the distal end of the outer sheath assembly 602 and the outer band 636.

Figure 3:
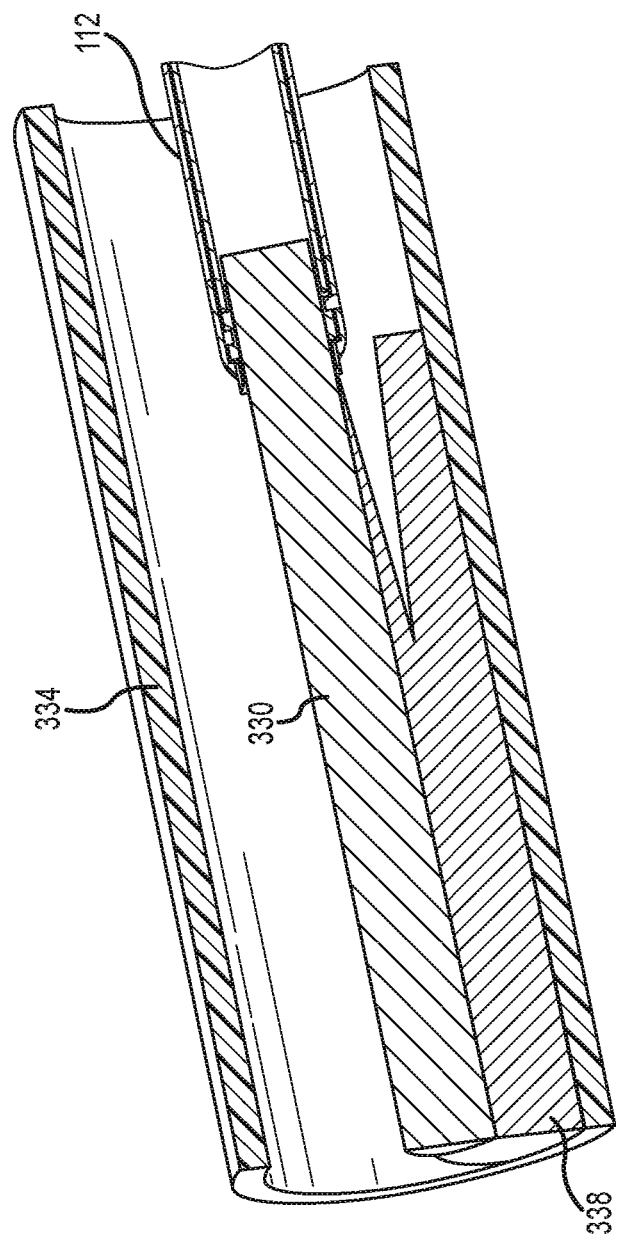
FIG. 3 is a cross-sectional view of a sheath assembly within a blood vessel with an extendable and rotatable blade for removing a lead according to an embodiment of the disclosure.

FIG. 3 depicts the distal portion of the flexible outer sheath and flexible inner sheath of FIG. 8A surrounding a lead 330 within a patient's vein 334 with the cutting tip 632 in its extended position. The circumferential nature of the cutting surface (e.g., notched blade) at the distal end of the cutting tip 632 causes the surgical device to act as a coring device, thereby cutting tissue 338 either partially (i.e., less than 360 degrees) or completely (i.e., 360 degrees) around the lead or implanted object being extracted. The amount of tissue that the cutting surface cuts depends upon the size, shape and configuration of the lead, as well as the diameter and thickness of the circular cutting blade. For example, if the diameter of the circular cutting surface is substantially greater than the diameter of the lead, then the cutting surface will cut and core more tissue in comparison to a cutting surface having a smaller diameter. Once the desired cut has been made, the operator releases trigger and the cutting tip 632 (including the cutting surface) returns to a retracted position. Upon the cutting surface returning to a retracted position, the distal tip of the outer band 636 (and/or other portions of the outer sheath assembly) safely acts as a dilating device, thereby stretching tissue as the outer sheath assembly move over the lead or implanted object to be extracted.

With each full squeeze of the trigger, the cutting tip (and inner sheath) will rotate clockwise and counterclockwise while extending and retracting. The cutting tip (and inner sheath) retracts into the tip of the outer sheath when the trigger is fully compressed and/or remains retracted at the release of the trigger after a full squeeze of the trigger. If the trigger is partially squeezed, it will not reset and the cutting tip (and inner sheath) will reverse its motion upon release of the trigger, returning the blade to the retracted position. The return to the fully returned trigger position results in a rotation of about 35 degrees that due to the profile at the distal cam, which retains the cutting in the sheathed position.

Although the inner sheath and outer sheath are coupled to one another via the cutting tip, the outer band, and the guide pin, the inner sheath assembly and outer sheath assembly may be coupled to one another in other ways. Stated differently, those of skill in the art will understand how to make and use the disclosed aspects, embodiments, and/or configurations after understanding the present disclosure to couple the sheaths in a manner to allow a cutting surface to extend and rotate beyond the distal end of the outer sheath. All such configurations within the knowledge of one skilled in the art are considered within the scope of this disclosure.

Figure 9A:
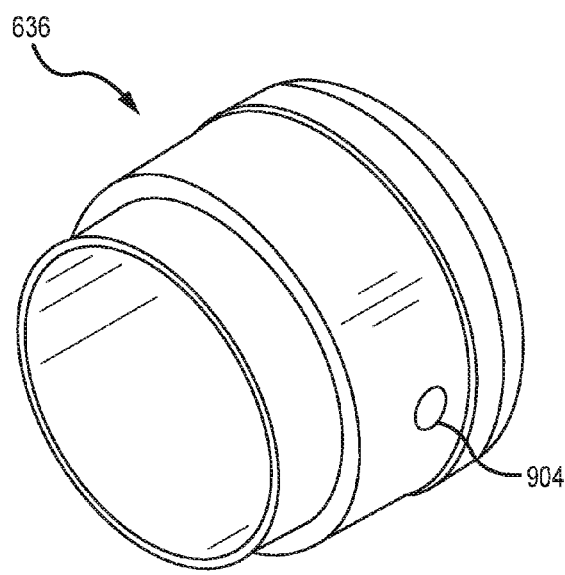
FIG. 9A is a perspective view of an outer band member according to an embodiment of the disclosure.
Figures 9B, 9C:
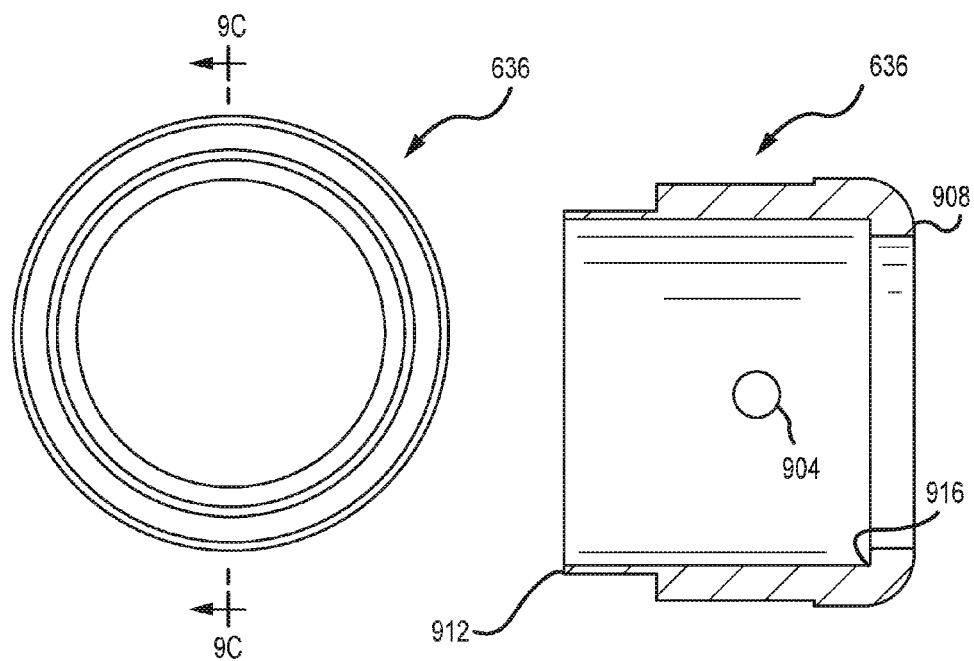
FIG. 9B is an end view of the outer band member illustrated in FIG. 9A.
FIG. 9C is cross-sectional view of the outer band member illustrated in FIG. 9A taken along line 9C-9C of FIG. 9B.

With reference to FIGS. 9A, 9B and 9C, an exemplary outer band 636 is depicted. The outer band 636 may be a sleeve in the general shape of a hollow cylinder. Although the exterior of the outer band 636 is non-uniform, it may be uniform. The interior of the outer band 636 is non-uniform. For example, the interior of the outer band 636 includes an abutment 916 to prevent the cutting tip (not shown in FIGS. 9A, 9B and 9C) from traveling further from the proximal end 912 to the distal end 908 within the outer band 636. The outer band 636 also includes a hole 904 for receipt and possible attachment of a guide pin (not shown in FIGS. 9A, 9B and 9C) which protrudes radially inward. As discussed in more detail above, the guide pin engages the cam slot of the cutting tip. The size, shape and configuration of the outer band 636 may differ depending upon how it is attached to the flexible outer sheath. As discussed above, the outer sheath may be stationary. If so, the outer band 636 and the guide pin remain stationary as the cutting tip moves (e.g., rotates and travel longitudinally) relative thereto. The outer band may also contain a journal bearing surface to align the cutting blade during actuation and provide a surface to disengage the tissue at the retraction of the cutting blade within the device.

With reference to FIGS. 10A, 10B, 10C and 10D, an exemplary cutting tip 632 is depicted. The cutting tip 632 has a generally hollow cylindrical shape. The cutting tip 632 comprises a proximal portion 1024, an intermediate portion 1028, and a distal portion 1032. The outside diameter of the proximal portion 1024 is sized to allow it to be inserted to and/or engage (or otherwise attached to) the interior diameter of the inner flexible sheath (not shown in FIGS. 10A, 10B, 10C and 10D). The distal end of cutting tip 632 comprises a cutting surface 1012 having a serrated, sharp blade profile. The intermediate portion 1028 comprises a channel (or cam slot) 1016 cut within its exterior surface. As the inner flexible sheath rotates and moves within the outer sheath—from its proximal end to distal end—the outer sheath and pin may remain stationary. If so, the inner sheath (not shown), which is connected to cutting tip 632, forces the cutting tip 632 to rotate. The cam slot 1016 engages the guide pin, and the shape and profile of the cam slot 1016 controls the rate and distance with which the cutting tip 632 travels longitudinally. That is, the configuration of the cam slot 1016 controls the cutting tip's direction and amount of longitudinal travel, such as moving distally toward an extended position and/or proximally toward a retracted position, while the cutting tip 632 rotates in either a clockwise or counter-clockwise direction.

Referring again to FIGS. 10A, 10B, 10C and 10D, the cutting tip 632 may also comprise a step up 1020 such that the diameter of the intermediate portion 1028 is greater than the distal portion 1032. As the cutting tip 632 rotates, and the cutting surface 1012 extends beyond the distal end of the outer band into an extended position, the step up 1020 of the cutting tip 632 contacts the abutment of the outer band, thereby limiting the distance that the cutting tip 632 may travel and/or may prevent the cutting tip 632 from exiting or extending beyond the distal tip of the outer sheath assembly, particularly the outer band, in the event that the pin is sheared.

Figure 10A:
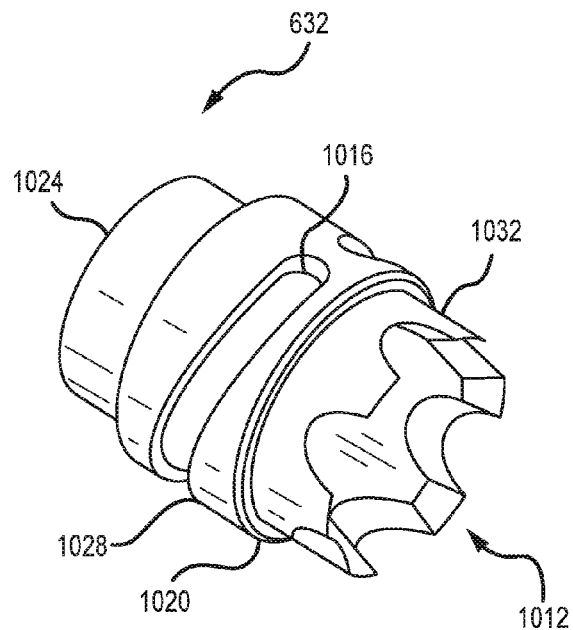
FIG. 10A is a perspective view of a cutting tip according to an embodiment of the disclosure.
Figure 10B:
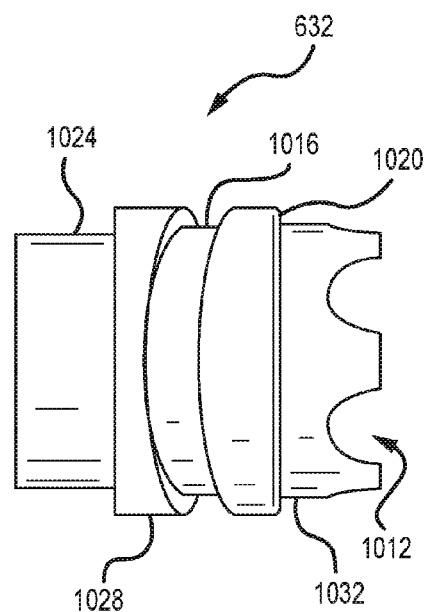
FIG. 10B is side view of the cutting tip illustrated in FIG. 10A.
Figure 10C:
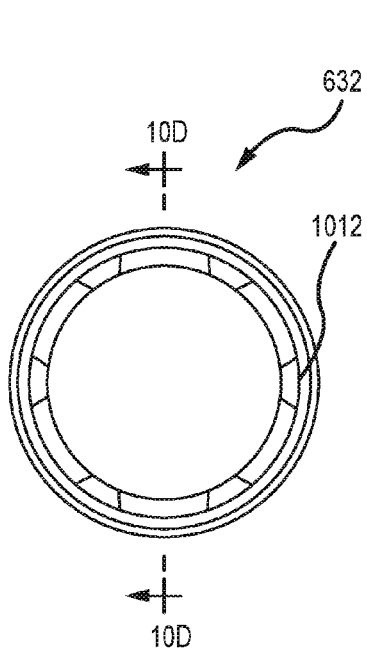
FIG. 10C is end view of the cutting tip member illustrated in FIG. 10A.
Figure 10D:
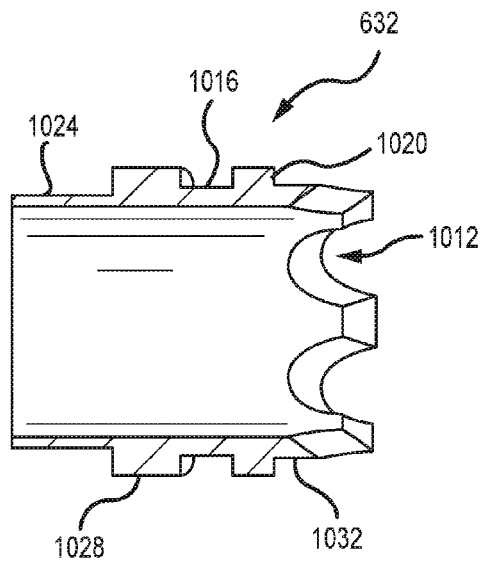
FIG. 10D is cross-sectional view of the cutting tip illustrated in FIG. 10A taken along line 10D-10D in FIG. 10C.

The profile of the cam slot in the cutting tip may have various configurations, such as those disclosed in U.S. patent application Ser. No. 13/834,405 filed Mar. 15, 2013 and entitled Retractable Blade For Lead Removal Device, which is hereby incorporated herein by reference in its entirety for all that it teaches and for all purposes. For example, the cam slot may have a substantially linear profile, a substantially sinusoidal profile, or a combination of individual and/or multiple linear and non-linear profiles. Additionally, the cam slot may have an open and continuous configuration, thereby allowing the cutting tip to continuously rotate, or the cam slot may have a closed and discontinuous configuration such that when the cutting tip reaches its fully extended position, the trigger assembly must be released or reversed so that the cutting tip returns to initially retracted position before being re-actuated. For instance, the cam slot 1016 in FIG. 10A is discontinuous because the cam slot does not travel around the entire circumference of the exterior of the cutting tip 632. Although certain figures in this disclosure only illustrate either the open or closed cam slot configuration, either configuration may be used with any of the inner cam embodiments disclosed and/or discussed herein and are considered within the scope of this disclosure. Furthermore, various types of cams, such as a partial lobe cam (which includes a cam slot surrounding less than 360 degrees of the circumference of the exterior surface of the cutting tip), a single lobe cam (which includes a cam slot surrounding 360 degrees of the circumference of the exterior surface of the cutting tip), double lobe cams (which includes a cam slot surrounding 720 degrees of the circumference of the exterior surface of the cutting tip) and/or other multiple lobe cams.

The distal end of cutting tip 632 may comprise a cutting surface 1012 having different blade profiles, such as those disclosed in U.S. patent application Ser. No. 13/834,405 filed Mar. 15, 2013 and entitled Retractable Blade For Lead Removal Device, which is hereby incorporated herein by reference in its entirety for all that it teaches and for all purposes. For example, the plane of the cutting surface 1012 of the distal end of the cutting tip depicted in the figures of this disclosure is parallel to the plane of the proximal end of the cutting tip. The plane of the cutting surface, however, may be offset (0 degrees to 90 degrees) from the plane of the proximal end of the cutting tip. Also, as discussed above, the profile of the cutting surface 1012 in FIGS. 10A-10D has a plurality of serrations. The profile of the cutting surface 1012 need not be serrated and may comprise other configurations, such as a constant and/or smooth sharp profile. The profile of the cutting surface 1012 in FIGS. 10A-10D has a plurality of six (6) serrations. However, it may be preferable to have less than or more than six (6) serrations. It may also be preferable to have between five (5) and seven (7) serrations, or between four (4) and eight (8) serrations, or between six (6) and ten (10) serrations.

Although the cutting surface 1012 illustrates a certain number of serrations, FIGS. 10A-10D are not intended to represent the only number and type of serrations that may be included in a serrated cutting surface. Depending upon the size of the surgical device, including the sheaths, and cutting tip, those of skill in the art will understand how to make and use the disclosed aspects, embodiments, and/or configurations after understanding the present disclosure to adjust the number, size and configurations of the serrations. All such configurations within the knowledge of one skilled in the art are considered within the scope of this disclosure. Furthermore, the serrations may comprise a myriad of different shapes and configurations, including but not limited to any variation of a square, rectangle, rhombus, parallelogram, trapezoid, triangle, circle, ellipse, kite, etc.

Figure 11:
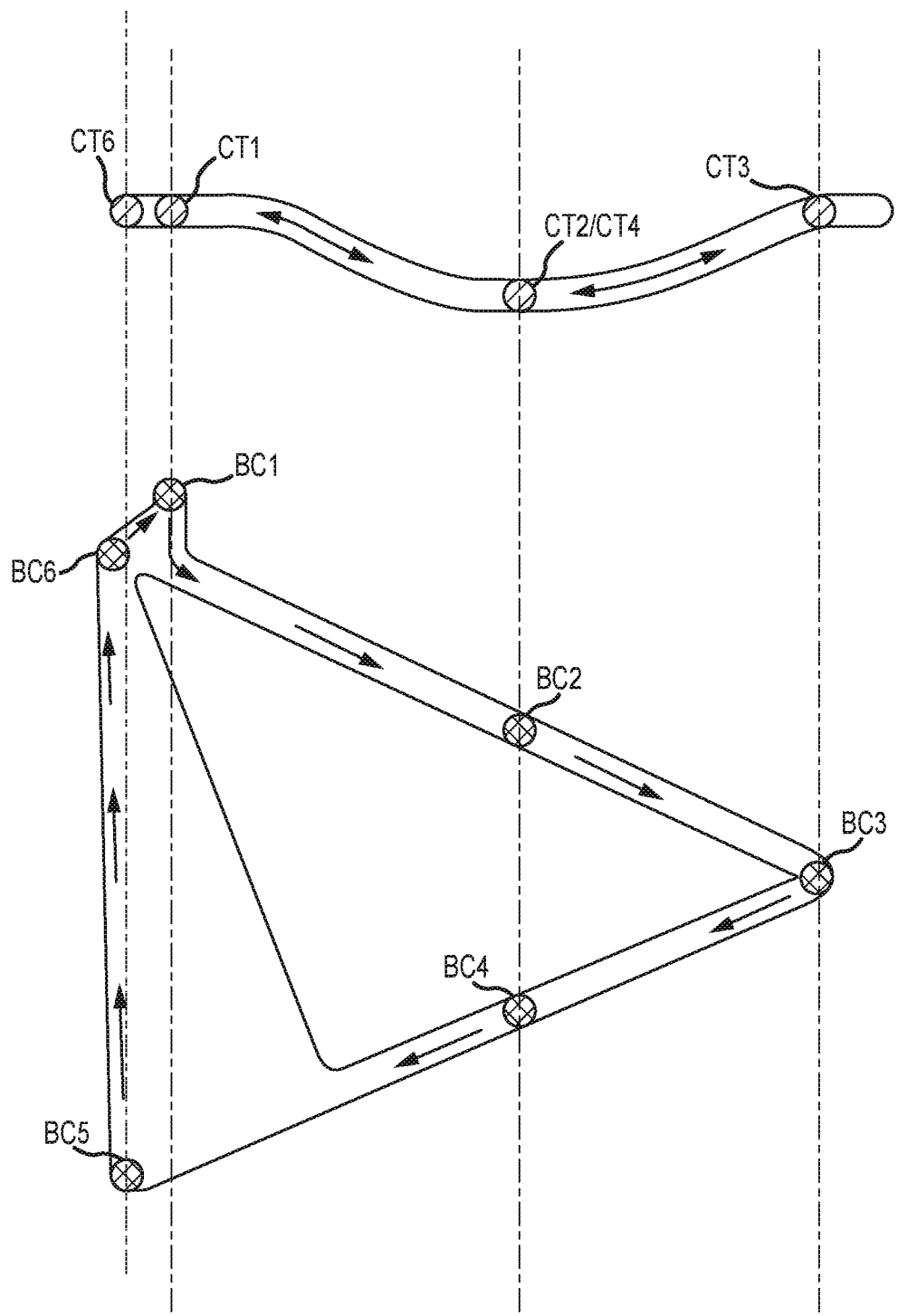
FIG. 11 is an illustration of the cam slot profile of the cutting tip and the cam slot of the barrel cam cylinder depicting the longitudinal position of the cutting tip in combination with the longitudinal position of the trigger for a particular amount of angular rotation by both the cutting tip and the barrel cam cylinder.

As discussed above, FIGS. 10A, 10B and 10D depict the intermediate portion 1028 of the cutting tip 632 having a cam slot (or channel) 1016 cut within its exterior surface, and FIGS. 4C and 4D depict the barrel cam cylinder 420 having a channel (or cam slot) 444 on its exterior surface that creates a non-linear cam profile. Referring to FIG. 11 there is depicted a two-dimensional illustration of the profile of the cam slot 1016 for the cutting tip 632 at the top of the figure and a two-dimensional illustration of the profile of the cam slot 444 for the barrel cam cylinder 420 at the bottom of the figure. The horizontal axis, which is the same for the top illustration and the bottom illustration, is the degree(s) of rotation of the cutting tip 632 and the barrel cam cylinder 420. For example, assuming that the profile of the cam slot 1016 in the cutting tip 632 is discontinuous, as depicted in FIG. 10A, the cutting tip 632 will rotate less than 360 degrees. It may be preferable for the cutting tip 632 to rotate between 5 and 355 degrees, 180 degrees and 355 degrees, 210 degrees and 325 degrees, 240 degrees and 295 degrees, or 270 degrees and 275 degrees. It may also be preferable for the cutting tip 632 rotate about 180, 185, 190, 200, 205, 210, 215, 220, 225, 230, 235, 240, 245, 250, 255, 260, 265, 270, 275, 280, 285, 290, 300, 305, 310, 315, 320, 325, 330, 335, 340, 345, 350 or 355 degrees. The first half of a trigger pull results in about a 273° rotation in one direction—clockwise when looking from the handle to the tip—thereby returning the cam blade to the sheathed position. The second half of the trigger pull results in about a 273° in the opposite direction—counter-clockwise when looking from the handle to the tip—thereby, returning the cutting blade to the sheathed position again. The blade remains in the sheathed position for the full return of the trigger to the forward position. The vertical axis for the top illustration is the amount of longitudinal movement, if any, of the cutting tip 632 including its cutting surface. The vertical axis for the bottom illustration is the amount of longitudinal displacement (in inches) of the trigger assembly (and trigger pin).

Referring to FIG. 11 in combination with FIGS. 5A-5E, the following discussion explains the interaction between the rotation of the barrel cam cylinder 420, the rotation of the cutting tip 632, the longitudinal movement of the handle (via the position of its trigger pin 428), and the longitudinal movement of the cutting tip 632. The following is a description of the positions CT1-CT6 of the guide pin 640 within the cam slot of the cutting tip 632:

CT1—the guide pin 640 is at its home position within the cam slot 1016 of the cutting tip 632, and the cutting tip 632 is in a retracted position within the outer sheath assembly 602 (including the outer band 636);

CT2—the cutting tip 632 has rotated in a clockwise direction over the guide pin 640 within the cam slot 1016 for about half of its predetermined rotation, and the cutting tip 632 is in its most extended position outside the outer sheath assembly 602;

CT3—the cutting tip 632 has completed its rotation in a clockwise direction over the guide pin 640 within the cam slot 1016, and the cutting tip 632 is in a retracted position within the outer sheath assembly 602;

CT4—the cutting tip 632 has rotated in a counter-clockwise direction over the guide pin 640 within the cam slot 1016 for about half of its predetermined rotation, and the cutting tip 632 is in its most extended position outside the outer sheath assembly 602;

CT5—(not shown) the cutting tip 632 has completed its rotation in a counter-clockwise direction over the guide pin 640 within the cam slot 1016, and the cutting tip 632 is in a retracted position within the outer sheath assembly 602; and CT6—the cutting tip 632 has completed its rotation in a counter-clockwise direction over the guide pin 640 within the cam slot 1016, and the cutting tip 632 is in its most retracted position within the outer sheath assembly 602.

The positions CT1-CT6 of the guide pin 640 within the cam slot of the cutting tip 632 correspond with positions BC1-BC6 of the trigger pin 428 within the cam slot of the barrel cam cylinder 420. The following is a description of the positions BC1-BC6 of the trigger pin 428 within the cam slot of the barrel cam cylinder 420:

BC1—the trigger pin 428 (along with the trigger 408 of the trigger assembly 106) is at its home position within the cam slot 444 of the barrel cam cylinder 420;

BC2—the trigger pin 428 has moved longitudinally in a proximal direction, thereby causing the barrel cam cylinder 420 to rotate in a clockwise direction; at this point, the barrel cam cylinder has rotated clockwise about half of its predetermined amount;

BC3—the trigger pin 428 has moved about half of its longitudinal movement is continuing to move longitudinally in a proximal direction and the barrel cam cylinder 420 has completed its rotation in a clockwise direction;

BC4—the trigger pin 428 is moving longitudinally in a proximal direction, thereby causing the barrel cam cylinder 420 to rotate in a counter-clockwise direction; at this point, the barrel cam cylinder has rotated counter-clockwise about half of its predetermined amount;

BC5—the trigger pin 428 has moved about its entire longitudinal movement in a proximal direction and the barrel cam cylinder 420 has completed its rotation in a counter-clockwise direction; and BC6—the trigger pin 428 has moved longitudinally in a distal direction, thereby causing the barrel cam cylinder 420 to rotate any remaining amount in a counter-clockwise direction.

Continuing to refer to FIG. 11 and FIGS. 5A-5E, when the trigger assembly 106, particularly the trigger 408, is at its initial, distal position, the trigger pin 428 is at its home position (BC1). Referring to the top illustration of FIG. 11, at the time the trigger pin 428 is at its home position (BC1), the guide pin 640 in the sheath assembly 112 is at its initial position (CT1), and the cutting tip 632 is at a retracted (or recessed) position within the outer sheath assembly 602. Upon a clinician pulling the trigger 408 and moving the trigger pin 428 proximally, both the barrel cam cylinder 420 and the cutting tip 632 rotate in a clockwise direction (from the proximal perspective of barrel cam cylinder). Upon the cutting tip 632 rotating adjacent the guide pin 640 from position CT1 to CT2, the profile of the cam slot in the cutting tip 632 causes the cutting tip 632 to move longitudinally in a distal direction from a retracted position to an extended position. When the trigger pin 428 is at position BC2, (i) the barrel cam cylinder 420 and the cutting tip 632 have rotated about half of its predetermined allowable rotation in the clockwise direction, (ii) the guide pin 640 is at position CT2, and (iii) the cutting tip 632 is at its most extended position.

As the clinician continues to pull the trigger, the trigger pin 428 continues to move proximally, and the barrel cam cylinder 420 and the cutting tip 632 continue to rotate in a clockwise direction. Specifically, the cutting tip 632 rotates adjacent the guide pin 640, and the profile of the cam slot in cutting tip 632 causes the cutting tip 632 to move longitudinally from position CT2, which is an extended position, to CT3, which is a recessed position. When the trigger pin 428 is at position BC3, (i) the barrel cam cylinder 420 and the cutting tip 632 have rotated about half of their predetermined allowable rotation in in the clockwise direction, (ii) the guide pin 640 is at position CT3, and (iii) the cutting tip 632 is at a retracted position within the outer sheath assembly 602 (including the outer band 636).

Referring to the top illustration of FIG. 11, the cam slot in the cutting tip 632 extends beyond position CT3. As discussed above, the inner sheath assembly and outer sheath assembly may both be flexible. In order to accommodate for the potentially additional length created by the flexing of the sheath assemblies, as well as accommodating for manufacturing tolerances, the cam slot 1016 in the cutting tip 632 extends beyond position CT3. For example, if during use of the surgical device, the home position of the guide pin 640 is slightly to the right of position CT1, rather than exactly at position CT1, then the extended length of the cam slot allows the guide pin 640 to travel to the right of position CT3, thereby allowing the cutting tip to rotate its total amount of allowable rotation in the clockwise direction without obstruction.

As the trigger pin 428 moves from position BC1 to BC3 in the barrel cam cylinder 420, and the barrel cam cylinder 420 rotates in a clockwise direction, the trigger pin 428 rides along the inside edge of the cam slot 444 in the barrel cam cylinder 420. However, when the trigger pin 428 moves from position BC3 to BC5 in the barrel cam cylinder, the barrel cam cylinder 420 rotates in a counter-clockwise direction, and the trigger pin 428 rides along the outside edge of the cam slot 444 in the barrel cam cylinder 420.

When the guide pin 640 reaches position CT3 in the cutting tip 632 and the trigger pin 428 reaches position BC3 in the barrel cam cylinder 420, the trigger assembly 106, particularly the trigger 408, has only travelled about half of its predetermined allowable distance in the longitudinal direction. As the user continues to pull the trigger assembly 106, the trigger 408 and trigger pin 428 continue to move proximally. As this occurs, the barrel cam cylinder 420 and the cutting tip 632 switch from rotating in a clockwise direction to rotating in a counter-clockwise direction. And because the cutting tip 632 switches from rotating in a clockwise direction to a counter-clockwise direction as the cutting tip 632 moves past position CT3 to CT4 adjacent the guide pin 640, the cutting tip 632 moves from a retracted position within the outer sheath assembly 602 (including the outer band 636) to an extended position or partially extended position outside the outer sheath assembly 602 (including the outer band 636). When the trigger pin 428 is at position BC4, (i) the barrel cam cylinder 420 and the cutting tip 632 have rotated counter-clockwise for slightly less than half (or half) of its predetermined allowable distance, (ii) the guide pin 640 is at position CT4, and (iii) the cutting tip 632 is at its most extended position.

As the user pulls the trigger 408 further, the trigger pin 428 continues to move proximally from position BC4 to position BC5 in the barrel cam cylinder 420, thereby causing the barrel cam cylinder 420 and cutting tip 632 to continue rotating in a counter-clockwise direction. Specifically, the cutting tip 632 rotates adjacent the guide pin 640 from position CC4 toward CC6, and the profile of the cam slot in the cutting tip 632 causes the cutting tip 632 to move from an extended position to a retracted position. When the trigger pin 428 is located at position BC5 in cam slot of the barrel cam cylinder 420, the trigger 408 has reached the end of its longitudinal movement in the proximal direction. Upon the trigger pin 428 surpassing position BC5 in the cam slot of the barrel cam cylinder 420, the constant force spring causes the trigger 408 and trigger pin 428 to reverse direction and travel toward its distal position.

As discussed above, for a discontinuous cam slot in the cutting tip 432, the cutting tip 432 rotates less than 360 degrees in either the clockwise or counter-clockwise direction. Assuming that the predetermined amount of allowable rotation is about 275 degrees, the amount of angular rotation by the barrel cam cylinder 420 in the clockwise direction from BC1 to BC3 and by the cutting tip 632 from CT1 to CT3 is about 275 degrees. The amount of angular rotation by the barrel cam cylinder 420 in the counter-clockwise direction from BC3 to BC5 and the cutting tip 632 from CT3 to CT3 is greater than 275 degrees by about nine degrees. This additional rotation (or over rotation) by the barrel cam cylinder 420 and the cutting tip 632 in the counter-clockwise direction ensures that the cutting tip 632, including its cutting surface, is covered by the outer sheath assembly 602, particularly the outer band 636. Upon the trigger 408 reaching the end of its longitudinal movement in the proximal direction at position BC5, the barrel cam cylinder 420 and cutting tip 632 continue to move in a counter-clockwise direction to position BC6 and position CT6, respectively. Specifically, barrel cam cylinder 420 rotates counter-clockwise form position BC5 to BC6 about 17 degrees, thereby causing the cutting tip 632 to rotate counter-clockwise the same amount from position CT5 (not shown) to position CT6, which is the cutting tip's most recessed position.

When trigger pin 408 is at position BC6 in the barrel cam cylinder 420 and the guide pin 640 is at position CT6 within the cutting tip 632, the barrel cam cylinder 420 and cutting tip 632 still need to return to their home positions BC1, CT1. In order for the barrel cam cylinder 420 and cutting tip 632 to return to their home positions BC1, CT1, the barrel cam cylinder 420 and cutting tip 632 rotate about 34.5 degrees in the clockwise direction from position BC6 to BC1 and from CT6 to CT1. When the trigger pin 428 is back to its home position (BC1), (i) the barrel cam cylinder 420 and cutting tip 632 have rotated counter-clock wise 307.6 degrees (and rotated clockwise 34.5 degrees), (ii) the guide pin 640 is at position CT1, and (iii) the cutting tip 632 is at a recessed position. That is, the cutting tip 632 (and barrel cam cylinder 420) have rotated a net 273.1 degrees in the clockwise direction in a retracted(home)-extended-retracted sequence of positions and 273.1 degrees in the counter-clockwise direction a retracted-extended-retracted(home) sequence of positions, even though the cutting tip 632 (and barrel cam cylinder 420) rotated in both a counter-clockwise direction and a clockwise direction in a retracted-extended-retracted (home) sequence of positions. The user may then repeat the process, if so desired.

Figure 12:
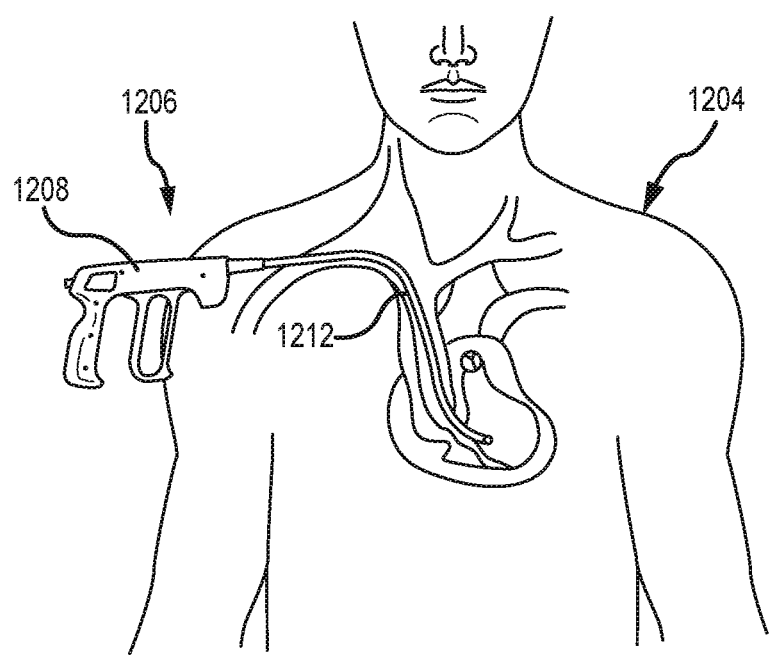
FIG. 12 is a perspective view of a human having a pacemaker lead located in the venous system and a terminating electrode anchored to the ventricular heart chamber, with an embodiment of a surgical device being shown inserted into the body and partly advanced over the lead.

Embodiments according to this disclosure provide a surgical device that includes a sheath assembly, which can be deployed safely within a vascular system of a patient and separate implanted objects, such as leads, from a patient's vasculature system. FIG. 12 depicts a surgical device 1206 having a sheath assembly 1212 inserted within an exemplary patient 1204. The sheath assembly 1212 surrounds an implanted lead (not shown) running along the left innominate vein past the SVC and connected into, or about, the right ventricle of the heart. Upon surrounding the lead with the sheath assembly 1212, the user of the surgical device 1206 may actuate the handle assembly 1208, thereby rotating and extending a cutting blade (not shown) beyond the distal end of the sheath assembly 1212 to dilate, separate and/or cut the tissue surrounding the lead within the patient's SVC.

The cutting blade may extend from and retract into the sheath upon actuation of the handle assembly according to the profile of the cam slot in the cutting tip disclosed below. The cutting blade may rotate in a first, or clockwise, direction upon an initial, or first, actuation of the handle assembly per the profile of the cam slot in the barrel cam cylinder discussed below. When the clinician releases the handle assembly, the cutting blade is ensured to remain or return within the sheath assembly 1212, thereby allowing the clinician to force and advance the distal portion of the sheath assembly against additional uncut tissue. The cutting blade may rotate in a second, or counter-clockwise, direction upon a subsequent, or second, actuation of the handle assembly per the profile of the cam slot in the barrel cam cylinder discussed below. Each time actuation occurs, the proximal portion of the implanted lead and/or surrounding tissue enters further into a hollow passageway within the sheath assembly 1212. This process is again repeated until the implanted lead and/or surrounding tissue is completely or substantially dilated, separated, and/or cut from the tissue attached to the SVC. At that time, the implanted lead may safely be removed from the patient's SVC.

Figure 13:
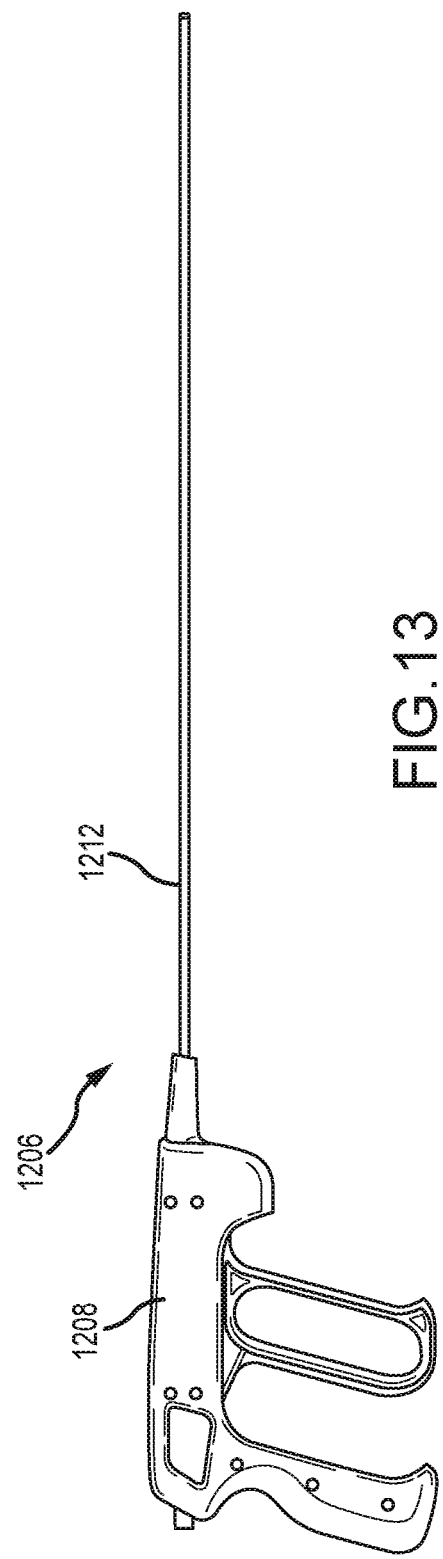
FIG. 13 is an elevation view of an embodiment of a surgical device.

With reference to FIG. 13, an exemplary surgical device 1206 is depicted. The surgical device 1206 includes a handle assembly 1208 and a flexible sheath assembly 1212. The flexible sheath assembly 1212, which is discussed in more detail below, generally includes a flexible inner sheath assembly (not shown) located within a flexible outer sheath assembly. It may be preferable for the outer sheath to remain stationary while the inner sheath is capable of moving (e.g., rotating and extending) with respect to the outer sheath. The inner sheath and outer sheath can both be flexible, rigid or a combination thereof.

With reference to FIG. 15A, an exemplary handle assembly 1208 is depicted. The handle assembly 1208 may include some or all of the following components: a handle frame 1504, a trigger 1508, a spring assembly 1512, a strain relief component 1516, a barrel cam assembly 1519, a bushing 1524 and an end cap 1527. The handle frame 1504 may be constructed of a singular component or multiple component, such as two halves as illustrated in FIG. 15A.

Figure 15B:
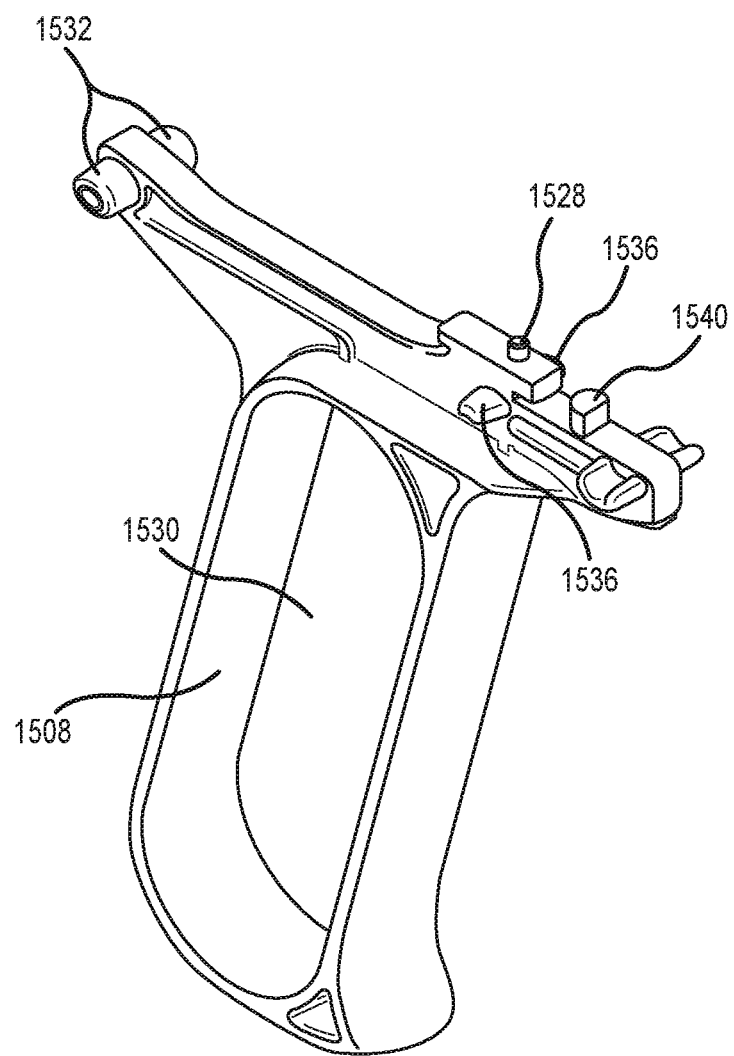
FIG. 15B is a perspective view of an embodiment of a trigger for the handle assembly illustrated in FIG. 15A.

Referring to FIG. 15B, an exemplary trigger 1508 is illustrated. The trigger 1508 depicted in FIG. 15B includes one opening 1530 into which a clinician can insert his/her fingers. A trigger, however, may have more than one opening. Additionally, a trigger may also be comprised of a straight or non-linear member without any openings. Furthermore, a trigger may be in the shape of a button capable of being depressed. As long as the trigger, either alone or in conjunction with the handle frame, is ergonomically correct and comfortable for the clinician, the trigger may have a variety of sizes and shapes.

The trigger 1508 illustrated in FIG. 15B includes a trigger pin 1528 that extends vertically from the top of the trigger 1508. The trigger pin 1528 may be formed of a metal, such as a copper alloy (for example, brass or bronze, particularly C 630 nickel aluminum bronze), and may include a frusto-conically shaped end to facilitate insertion into the handle frame 1504. The trigger pin 1528, which cooperates with a groove in a barrel cam cylinder of the barrel cam assembly 1519, acts as a follower for the barrel cam cylinder. The trigger 1508 also includes a pair of sliders 1532 protruding laterally from the proximal end of the trigger 1508 and a pair of sliders 1536 protruding laterally from the distal end of the trigger 1508. When the trigger 1508 is located within the handle assembly 1208, the sliders 1532, 1536 sit and slide in corresponding grooves within the handle frame 1504. The trigger 1508 also includes a post 1540 extending vertically from the top of trigger 1508, and preferably from the distal end of the top of the trigger 1508. The post 1540 connects to the spring assembly 1512.

As mentioned above, the handle assembly 1208 may include a strain relief component 1516. The strain relief component 1516, as illustrated in FIG. 15A, is attached to the distal end of the handle frame 1504 and tapers from its proximal end toward its distal end. The strain relief component 1516 also has a lumen passing through it, thereby allowing the sheath assembly 1212 to extend there through and into the handle assembly 1208. The strain relief component 1516 may be constructed of a flexible material such as, Santoprene™ thermoplastic vulcanizate produced by ExxonMobil. The material from which the strain relief component is made and the shape of the strain relief component provide a flexural modulus to protect the flexible shaft as it extends the rigid handle. The lumen of the strain relief may also contain a counter bore that enables ancillary outer sheaths to be docked during device preparations.

Figure 15C:
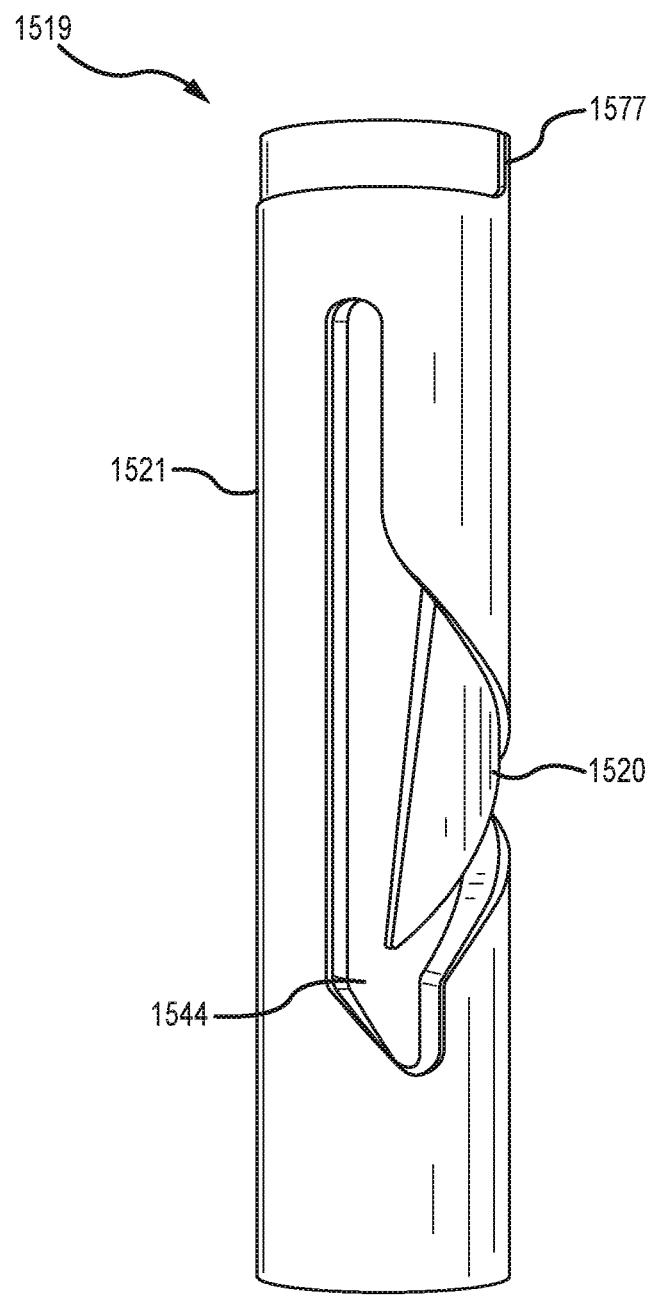
FIG. 15C is an elevation view of an embodiment of the barrel cam assembly for the handle assembly illustrated in FIG. 15A.

Referring to FIG. 15C, an exemplary barrel cam assembly 1519 is illustrated. The barrel cam assembly 1519 includes a barrel cam cylinder 1520 that rotatably carries a follower guide 1521. As described in further detail below, the barrel cam cylinder 1520 and the follower guide 1521 cooperate with the trigger pin 1528 to create the barrel cam.

Figure 15D:
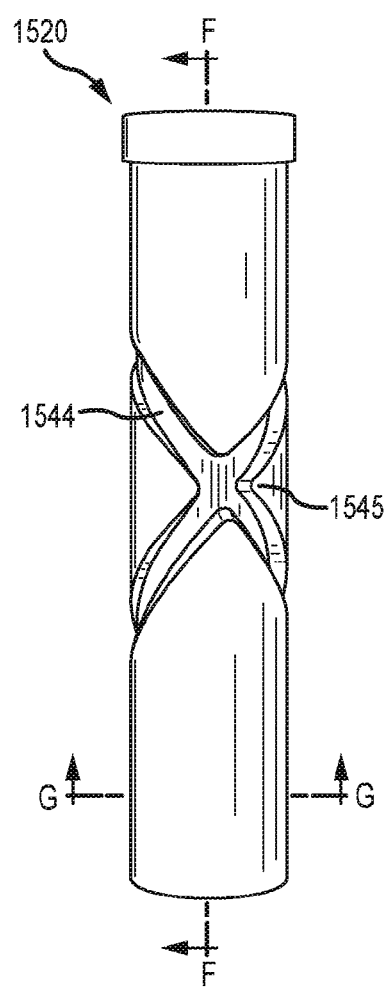
FIG. 15D is an elevation view of a barrel cam cylinder of the barrel cam assembly illustrated in FIG. 15C.
Figure 15E:
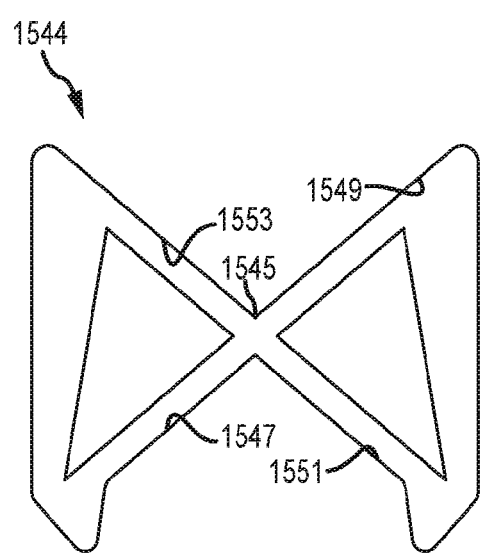
FIG. 15E is an illustration of the cam slot profile of the cam slot of the barrel cam cylinder illustrated in FIG. 15D.

The barrel cam cylinder 1520 may be formed from one or more biocompatible materials, such as polyethylene-filled Delrin®, stainless steel, anodized aluminum, brass, titanium, or the like. As illustrated in FIG. 15D, the barrel cam cylinder 1520 has an exterior surface comprising a cam groove (or slot or channel) 1544 that translatably receives the trigger pin 1528. FIG. 15E depicts a two-dimensional illustration of the profile of the cam slot 1544 for the barrel cam cylinder 1520. The cam slot 1544 defines a generally "hourglass"-like or "figure eight"-like path for the follower (that is, the trigger pin 1528). As described in further detail below, the trigger pin 1528 traverses about half of the cam slot 1544 when an initial, or first, actuation is applied to the trigger 1508, and the trigger pin 1528 traverses the remainder of the cam slot 1544 (that is, about half of the cam slot 1544) when a subsequent, or second, actuation is applied to the trigger 1508. In each case, and as described in further detail below, the follower guide 1521 causes the trigger pin 1528 to travel straight through the intersection (or crossing portion) 1545 of the cam slot 1544 during each actuation of the trigger 1508. Stated another way, the follower guide 1521 causes the trigger pin 1528 to travel from a first leg 1547 of the cam slot 1544 to a second parallel leg 1549 of the cam slot 1544, and then from a third leg 1551 of the cam slot 1544 to a fourth parallel leg 1553 of the cam slot 1544.

Figure 15F:
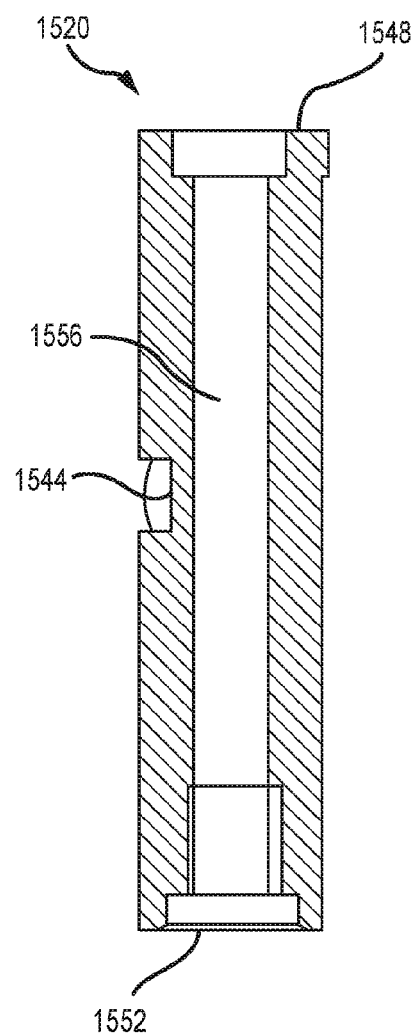
FIG. 15F is a longitudinal-sectional view of the barrel cam cylinder illustrated in FIG. 15D.
Figure 15G:
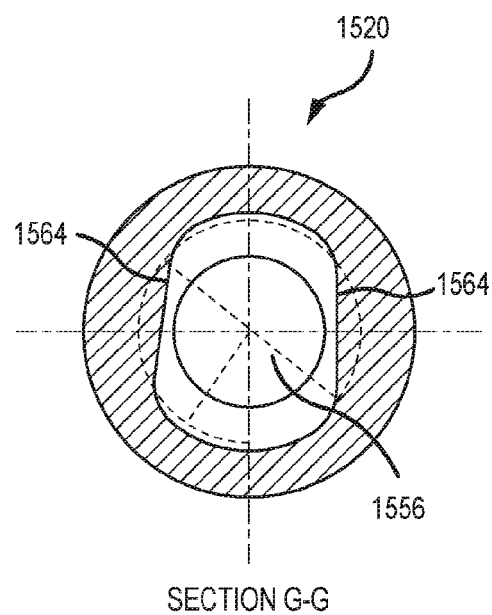
FIG. 15G is a cross-sectional view of the barrel cam cylinder illustrated in FIG. 15D.

FIGS. 15F and 15G illustrate a longitudinal-sectional view and a cross-sectional view, respectively, of the barrel cam cylinder 1520. The barrel cam cylinder 1520 has a proximal end 1548 and a distal end 1552 through which a lumen 1556 extends. The distal end 1552 of the lumen 1556 of the barrel cam cylinder 1520 is designed to mate with exterior of the proximal end of the inner key 1612, which is discussed in further detail below. The cross section of the distal end 1552 of the lumen 1556 of the barrel cam cylinder 1520 is preferably non-circular. For example, one embodiment of a non-circular lumen includes two chamfered sides 1564, wherein one chamfered side 1564 is not offset, and the other chamfered side 1564 is offset (e.g., about 8 degrees). Because the distal end of the barrel cam cylinder 1520 is designed to mate with exterior of the proximal end of the inner key 1612 and transfer torque from the barrel cam cylinder 1520 to the inner sheath assembly via the inner key 1612, the cross section of the exterior of proximal end of the inner key 1612 will have a complimentary profile of the lumen 1556. Although the cross sectional shape of the non-circular lumen is described as having two chamfered sides 1564, the disclosure shall not be limited to such shape and may include alternative non-circular shapes, such as a square, rectangle, D-shape, triangle, rhombus, trapezoid, pentagon, hexagon, octagon, parallelogram, ellipse, etc. Alternatively, the inner key could couple to the outside of the barrel cam cylinder.

The proximal end of the barrel cam cylinder 1520 mates with the bushing 1524. Specifically, the exterior, distal end of the bushing 1524 is located within the proximal end of the lumen 1556. Both the exterior, distal end of the bushing 1524 and the proximal end of the lumen 1556 are circularly shaped, thereby allowing the bushing 1524 and the barrel cam cylinder 1520 to rotate with respect to one another. The proximal end of the exterior of the bushing 1524, however, is located within a groove within the handle frame 1504, thereby preventing the bushing 1524 and the barrel cam cylinder 1520 from moving longitudinally within the handle assembly 1208.

The follower guide 1521 may be formed from one or more biocompatible materials, such as stainless steel, anodized aluminum, titanium, or the like. In some embodiments, the follower guide 1521 and the barrel cam cylinder 1520 have a relatively high coefficient of friction therebetween. The follower guide 1521 is rotatably carried by the barrel cam cylinder 1520; as such, it may be preferable for the follower guide 1521 to be a dissimilar material from the barrel cam cylinder 1520 to inhibit galling. In some embodiments, the inner surface of the follower guide 1521 may have a slightly different cross-sectional shape than that of the outer surface of the barrel cam cylinder 1520 to inhibit unintentional rotation of the follower guide 1521 relative to the barrel cam cylinder 1520. For example, the outer surface of the barrel cam cylinder 1520 may have a circular cross-sectional shape, and the inner surface of the follower guide 1520 may have a slightly non-circular cross-sectional shape.

Figure 15H:
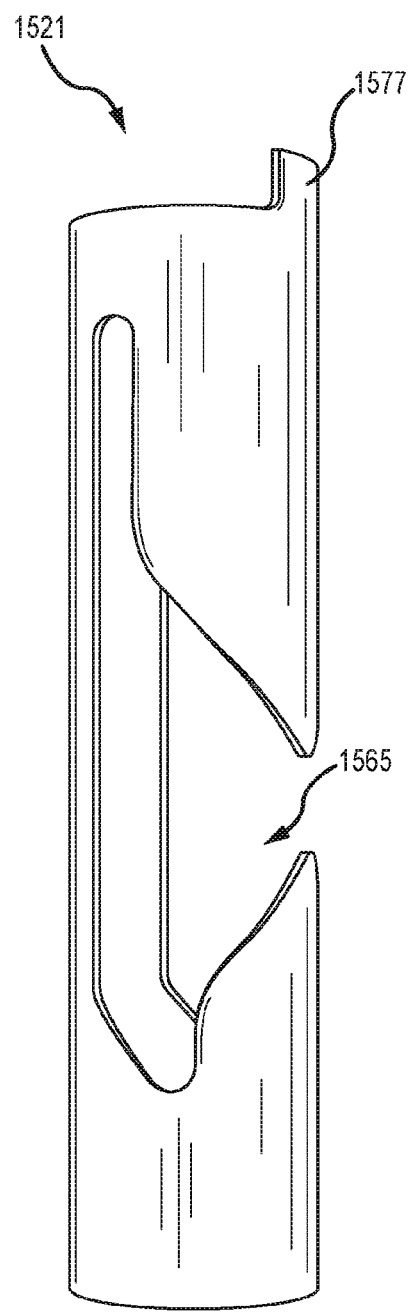
FIG. 15H is an elevation view of a follower guide of the barrel cam assembly illustrated in FIG. 15C
Figure 15I:
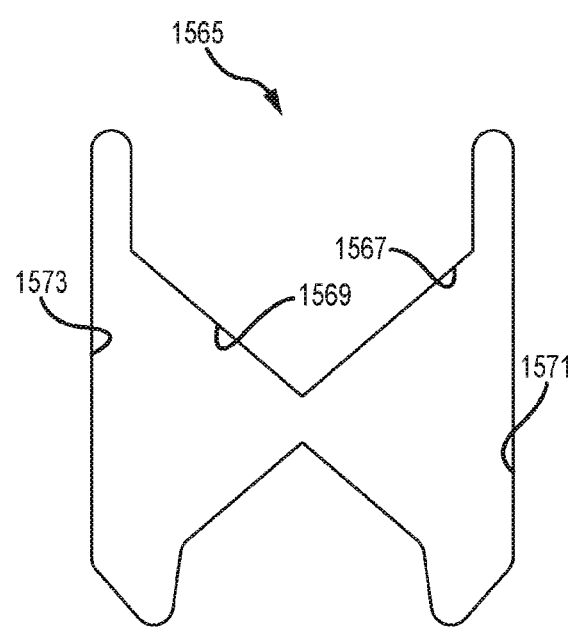
FIG. 15I is an illustration of the aperture profile of the follower guide illustrated in FIG. 15H.

As illustrated in FIG. 15H, the follower guide 1521 is a generally cylindrical component that includes an aperture 1565. The trigger pin 1528 extends through the aperture 1565 to enter the cam slot 1544 of the barrel cam cylinder 1520. As explained in further detail below, first and second diagonally extending walls 1567 and 1569 of the aperture 1565 (that is, diagonally extending relative to the longitudinal axis of the barrel cam assembly 1519) engage the trigger pin 1528 to cause the trigger pin 1528 to travel straight through the intersection 1545 of the cam slot 1544. In additional and as explained in further detail below, the follower guide 1521 rotates relative to the barrel cam cylinder 1520 to appropriately position the first and second diagonally extending walls 1567 and 1569 during first and second actuations of the trigger 1508. The aperture 1565 includes first and second longitudinally extending walls 1571 and 1573 (that is, walls extending parallel to the longitudinal axis of the barrel cam assembly 1519) that engage the trigger pin 1528 to facilitate rotation of the follower guide 1521 relative to the barrel cam cylinder 1520.

The first and second diagonally extending walls 1567 and 1569, the first and second longitudinally extending walls 1571 and 1573, and the other walls that define the aperture 1565 extend from an inner surface to an outer surface of the follower guide 1521. In some embodiments, these walls extend in a radial direction between the inner surface and the outer surface. In some embodiments, these walls extend diagonally between the inner surface and the outer surface (that is, these walls form a chamfer between the inner surface and the outer surface).

Figure 15J:
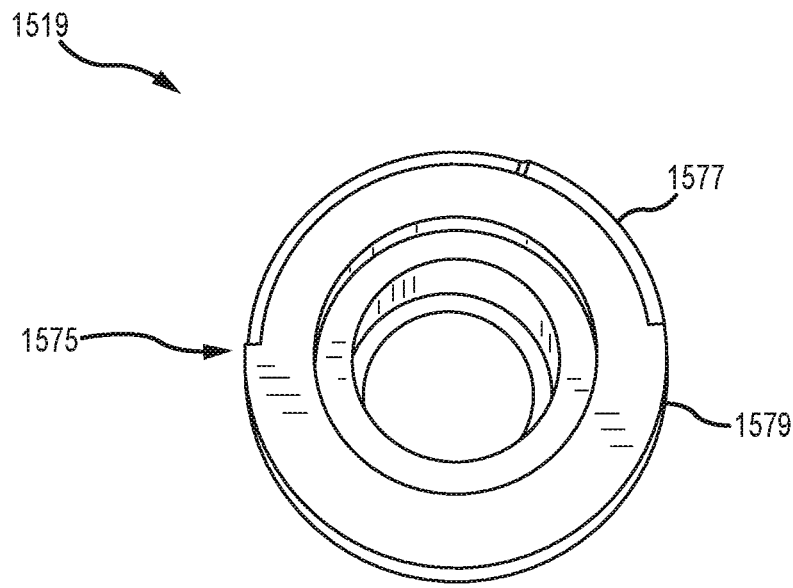
FIG. 15J is an end view of the barrel cam assembly of FIG. 15C illustrating a relative rotation-inhibiting mechanism in a first relative rotation-inhibiting position.
Figure 15K:
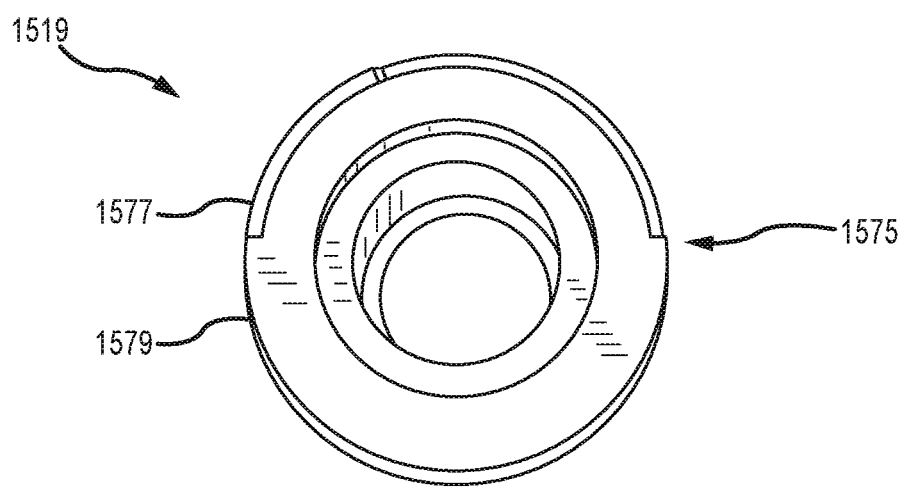
FIG. 15K is an end view of the barrel cam assembly of FIG. 15C illustrating the relative rotation-inhibiting mechanism in a second relative rotation-inhibiting position.

Referring now to FIGS. 15J and 15K, the barrel cam assembly 1519 further includes a relative rotation-inhibiting mechanism 1575 that, as the name implies, inhibits some rotation of the follower guide 1521 relative to the barrel cam cylinder 1520. Generally, the relative rotation-inhibiting mechanism 1575 permits the follower guide 1521 to occupy a first relative rotation-inhibiting position and a second relative rotation-inhibiting position. In the first relative rotation-inhibiting position, the mechanism 1575 permits the follower guide 1521 to rotate in a first direction relative to the barrel cam cylinder 1520 (that is, toward the second relative rotation-inhibiting position) and inhibits rotation of the follower guide 1521 relative to the barrel cam cylinder 1520 in a second direction. In the second relative rotation-inhibiting position, the mechanism 1575 permits the follower guide 1521 to rotate in the second direction relative to the barrel cam cylinder 1520 (that is, toward the first relative rotation-inhibiting position) and inhibits rotation of the follower guide 1521 relative to the barrel cam cylinder 1520 in the first direction.

In some embodiments and as shown in FIGS. 15J and 15K, the relative rotation-inhibiting mechanism 1575 may include a longitudinally extending tab (or arm) 1577 (see also FIGS. 15C and 15H) carried by the follower guide 1521 and a semi-annular flange 1579 (see also FIGS. 15C and D) carried by the barrel cam cylinder 1520. FIG. 15J illustrates such an embodiment of the relative rotation-inhibiting mechanism 1575 in the first relative rotation-inhibiting position (the arm 1577 engages a first side of the semi-annular flange 1579), and FIG. 15K illustrates such an embodiment of the relative rotation-inhibiting mechanism 1575 in the second relative rotation-inhibiting position (the arm 1577 engages a second side of the semi-annular flange 1579).

In some embodiments, the relative rotation-inhibiting mechanism 1575 may take other forms. For example, the mechanism 1575 may include one or more magnets that hold the follower guide 1521 in the first and second relative rotation-inhibiting positions.

Figure 15L:
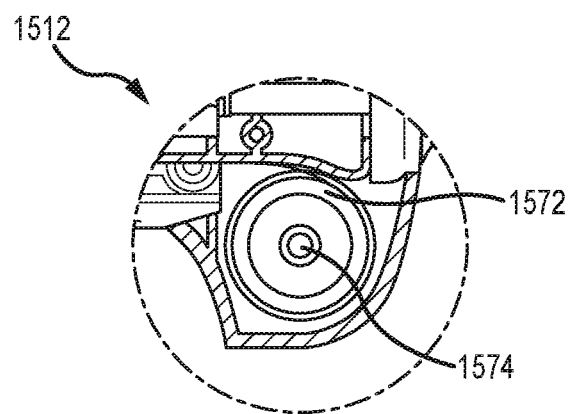
FIG. 15L is an enlarged perspective view of an embodiment of a spring assembly for the handle assembly illustrated in FIG. 15A.

Referring to FIG. 15L, an exemplary spring assembly 1512 is depicted. The spring assembly 1512 includes a constant force spring 1572 and a spool 1574. One end of the constant force spring 1572 is connected to the spool 1574, and the other end of the constant force spring 1572 is connected to the post 1540 extending from the trigger 1508. As a clinician pulls the trigger 1508 proximally, the sliders 1532, 1536 travel and slide in the grooves within the handle frame 1504, thereby preventing the trigger 1508 from moving vertically within the handle assembly 1208 and only allowing the trigger 1508 to move along the longitudinal axis of the surgical device 1206 from its distal end toward its proximal end and/or vice versa. As the trigger 1508 moves proximally, the constant force spring 1572 uncoils, thereby creating tension and a distally directed force. Accordingly, when the trigger 1508 is released by the clinician, the constant force spring 1572 recoils and pulls the trigger 1508 back towards its original and most distal position.

Referring to FIG. 16, there is depicted an elevation view of an embodiment of an assembled sheath assembly 1212 of the present disclosure. The sheath assembly 1212 includes an inner sheath assembly and an outer sheath assembly. Referring to FIG. 16A, which illustrates an exploded view of the distal end of the sheath assembly 1212, and referring to FIG. 16B, which is an exploded illustration of the proximal end and central portion of the sheath assembly 1212, the sheath assembly 1212 may include may include some or all of the following components: an outer band 1636; a guide pin 1640; a cutting tip 1632; a flexible inner sheath 1620; a flexible outer sheath 1624; an outer jacket 1628; an inner key 1612; an outer key 1608; and a rigid inner tube 1616.

Referring to FIG. 17A, there is depicted an embodiment of the outer sheath assembly 1602 of the present disclosure. The outer sheath assembly 1602 includes an outer band 1636 located at and attached to the distal end of an elongated flexible outer sheath 1624, and an outer key 1608 located at and attached to the proximal end of the flexible outer sheath 1624. The outer band 1636 may be attached to the distal end of a flexible outer sheath 1624 via a weld, an adhesive, a press-fitting technique, an interlock such as a barbed joint or other known means of attachment. All such attachment techniques within the knowledge of one skilled in the art are considered within the scope of this disclosure. Similarly, the outer key 1608 may be attached to the proximal end of the flexible outer sheath 1624 via a weld, an adhesive, a press-fitting technique, interlock such as a barbed joint, or other known means of attachment. Although it is not shown on FIG. 17A, the outer sheath assembly 1602 may also include a flexible outer jacket 1628 (see FIG. 16A) that covers the outer sheath 1624 and abuts the outer band 1636, thereby providing the outer sheath assembly 1602 with a relatively smooth, continuous and uninterrupted exterior profile. The flexible jacket also contains the egress of blood from the system.

Referring to FIG. 17B, there is depicted an embodiment of the inner sheath assembly 1604 of the present disclosure. The inner sheath assembly 1604 includes a cutting tip 1632, a flexible inner sheath 1620, an inner key 1612, and a rigid inner tube 1616. The proximal end of the cutting tip 1632 is attached to the distal end of a flexible inner sheath 1620; the distal end of an inner tube 1616 is attached to the proximal end of the flexible inner sheath 1620; and an inner key 1612 is attached to the proximal end of the inner tube 1616. The means of attaching these components may include a weld, an adhesive, a press-fitting technique, or other known means of attachment. As will be discussed below, the guide pin 1640 couples the outer band 1636 with the cutting tip 1632, and the guide pin 1640 may be includes with either the inner sheath assembly 1604 or the outer sheath assembly 1602.

It may be preferable for a portion of either the inner sheath 1620 and/or the outer sheath 1624 to be rigid and a portion of the outer sheath to be flexible. Both the rigid portion and the flexible portion may be constructed of materials suitable for insertion into the human body. For example, the rigid portion may be constructed of stainless steel, and the flexible portion may be constructed of a flexible polymer such as polytetrafluoroethylene or thermoplastic elastomers. Assuming that both a rigid portion and a flexible portion are used, they will form a unitary inner sheath and/or outer sheath. As depicted in FIG. 17B, the rigid inner tube 1616 is not only attached to the inner key 1612, the rigid tube 1616 also is inserted through the inner key 1612 and extends from both the proximal end and distal end of the inner key 1612. The attachment and extension of the rigid tube 1616 to the inner key 1612 allows for an increased amount of torque that can be transferred from the barrel cam to the rigid tube 1616 via the inner key 1612 and eventually to the cutting tip 1632 via the inner sheath assembly 1604. The extension of the rigid tube through the handle provides an access point for introduction of other medical devices. The extension also provides a means of controlling blood egress after the lead has been extracted.

It may be preferable that at least a portion of the outer sheath 1624 and the inner sheath 1620 be generally flexible in order to accept, accommodate and navigate the patient's vasculature system. In addition to being flexible, the inner sheath 1620 may also have a high degree of stiffness in order to receive the torque transferred from the barrel cam cylinder/inner key and transfer sufficient torque to the cutting tip 1632 discussed in more detail below. The inner sheath 1620 (and/or the outer sheath 1624) may be formed of a polymer extrusion, braided reinforced polymer extrusion, coils, bi-coils, tri-coils, laser cut metal tubing and any combination of the above. The inner sheath (and/or the outer sheath 1624) may be a unitary structure comprised of multiple portions.

Referring to FIG. 18, there is depicted a cross-sectional view of an embodiment of the sheath assembly 1212 comprising the inner sheath assembly 1604 located within the outer sheath assembly 1602. Referring to FIG. 18C, there is depicted an enlarged view of the inner key 1612 of the inner sheath assembly 1604 located within the outer key 1608 of the outer sheath assembly 1602. As discussed above, the exterior of the inner key 1612 is designed to mate with lumen 1556 of the distal end of the barrel cam cylinder 1520. Accordingly, the cross section of the exterior of proximal end of the inner key 1612 will have a profile complimentary to the distal end of the lumen 1556 within the barrel cam cylinder 1520. For example, assuming the cross section of the distal end 1552 of the lumen 1556 of the barrel cam cylinder 1520 is non-circular and has two chamfered sides, wherein one chamfered side is not offset, and the other chamfered side is offset (e.g., about 8 degrees), then the exterior of the proximal end of the inner key 1612 will also have a non-circular profile with two chamfered sides, wherein one chamfered side is not offset, and the other chamfered side is offset (e.g., about 8 degrees). The inner key 1612 and outer key 1608 provide means for rotationally coupling. The inner key 1612 is a means for rotationally coupling the inner sheath assembly 1604 to the barrel cam, and the outer key is a means for rotationally coupling the outer shaft assembly to the handle. The inner key 1612 and outer key 1608 provide journal bearing for the other key.

Figure 18B:
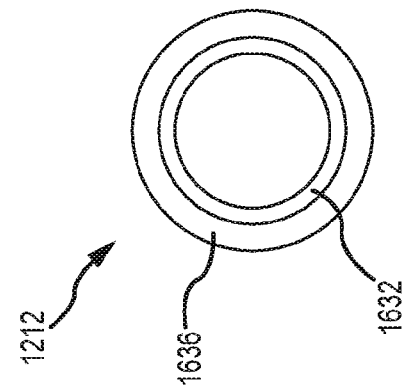
FIG. 18B is a distal end view of the inner sheath assembly located within the outer sheath assembly illustrated in FIG. 18.
Figure 18C:
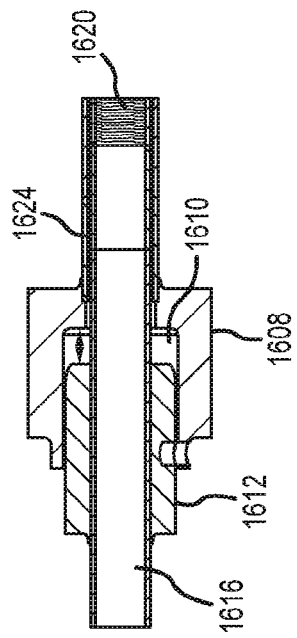
FIG. 18C is an enlarged cross-sectional view of the inner key of the inner sheath assembly located within the outer key of the outer sheath assembly illustrated in FIG. 18.

As further illustrated in FIG. 18C, the inner key 1612 is able to rotate freely within the outer key 1608 due, at least in part, to the distal end of the exterior of the inner key 1612 having a circular cross section that mates with a circular cross section of the proximal end of a lumen within the outer key 1608. Additionally, because the inner key 1612 and outer key 1608 are loosely coupled, the inner key 1612 and outer key 1608 are able to move longitudinally with respect to one another. For instance, supposing the outer key 1608 is fixed such that it neither rotates nor moves longitudinally, the inner key 1612 is able to both rotate and travel longitudinally within the outer key 1608. Accordingly, as the barrel cam cylinder 1520 rotates, the inner key 1612 will rotate within the outer key 1608, and the inner sheath assembly 1604 will rotate within the outer sheath assembly 1602, including the rotation of the cutting tip 1632 within the outer band 1636. And the cam slot profile in the cutting tip 1632 controls the longitudinal movement of the inner sheath assembly 1604 within the outer sheath assembly 1602, including the longitudinal movement of the inner key 1612 relative to the outer key 1608 and the longitudinal movement of the cutting tip 1632 relative to the outer band 1636.

Continuing to refer to FIG. 18C, the lumen within the outer key 1608 is larger toward its proximal end and smaller toward its distal end because there is a step down or an abutment in the lumen as it progresses from the proximal end to the distal end. Due to the transition from a larger lumen to a smaller lumen within the outer key 1608, there is depicted an adjustable gap 1610 between the distal end of the inner key 1612 and the abutment within the distal end of the larger lumen in the outer key 1608. This gap increases, decreases and/or remains the same according to the cam slot profile of the cutting tip 1632. The abutment in the outer key 1608 insures that the inner key 1612 will only travel a limited longitudinal distance within the outer key 1608, thereby limiting the inner sheath assembly 1604 potential longitudinal movement within the outer sheath assembly 1602, including limiting the longitudinal movement of the cutting tip 1632 relative to the outer band 1636 in the distal direction.

Figure 18A:
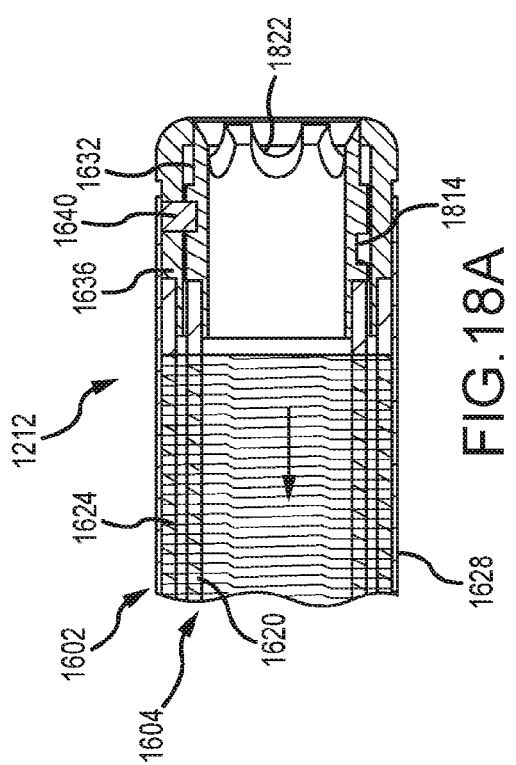
FIG. 18A is an enlarged cross-sectional view of the distal end of the inner sheath assembly located within the outer sheath assembly illustrated in FIG. 18, wherein the blade is retracted and located within the outer sheath assembly.
Figure 18A:
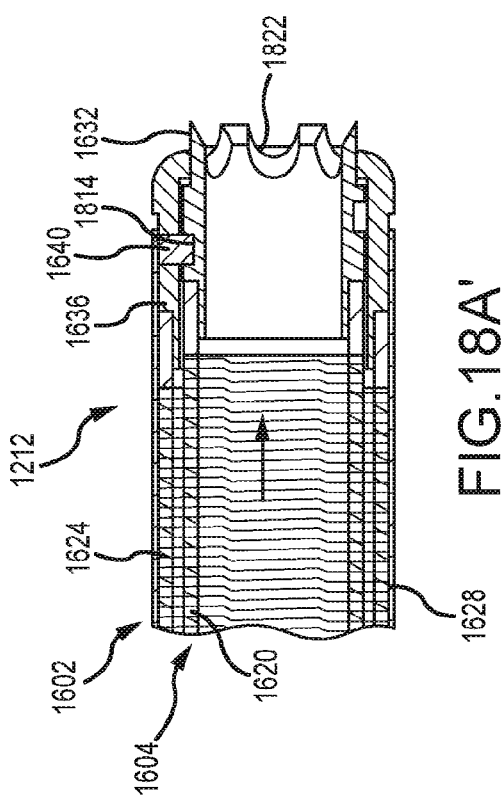

Referring to FIG. 18A, there is depicted an enlarged cross-sectional view of the distal end of the sheath assembly 1212 with the inner sheath assembly 1604 coupled with the outer sheath assembly 1602 via guide pin 1640, wherein the blade 1822 of the cutting tip 1632 is in a retracted position and located within the outer sheath assembly 1602. As discussed above, the distal end of the outer sheath assembly 1602 includes an outer band 1636, which may be constructed of a biocompatible metal, such as stainless steel, and polished so that it is generally smooth and evenly rounded at its most distal point, thereby allowing it to act as a dilator when pressed and forced against tissue. The distal end 1822 of cutting tip 1632 includes a cutting surface capable of cutting tissue. The inner sheath assembly 1604 is coupled to the outer sheath assembly 1602 through the cutting tip 1632 and the outer band 1636, respectively, via guide pin 1640. One end of the guide pin 1640 is fixed within the outer band 1636, and the other end of the guide pin 1640 is located within the cam slot 1814 of the cutting tip 1632. As the inner sheath 1620 rotates, upon actuation of the trigger assembly discussed above, the cutting tip 1632 also rotates because the inner sheath 1620 is fixedly attached to the cutting tip 1632. As the cutting tip 1632 rotates, the cutting tip 1632 may also extend distally in the direction of the arrow (→) according to the profile of the cam slot 1814 as depicted in FIG. 18A'. As the cutting tip 1632 extends distally and rotates, the guide pin 1640 and the outer sheath assembly 1602, particularly the outer band 1636, remain stationary. Thus, as the cutting tip 1632 extends distally (and potentially retracts proximally according to the cam slot profile) and rotates, the cutting surface at the distal end 1822 of the cutting tip 1632 is able to perform a slicing action against the tissue and cut it.

Again, FIG. 18A depicts the cutting tip 1632 within a retracted (and potentially un-actuated) position because the cutting tip 1632 is in a proximal position. Stated differently, the distal end 1822 of the cutting tip 1632 of FIG. 18A is located within the interior of the outer sheath assembly 1602, particularly the outer band 1636, and does not extend beyond the distal end of the outer band 1636. With reference to FIG. 18A', the cutting tip 1632 is depicted in an extended (and actuated) position because the cutting tip 1632 is extending beyond the distal end of the outer sheath assembly 1602 and the outer band 1636.

Figure 14:
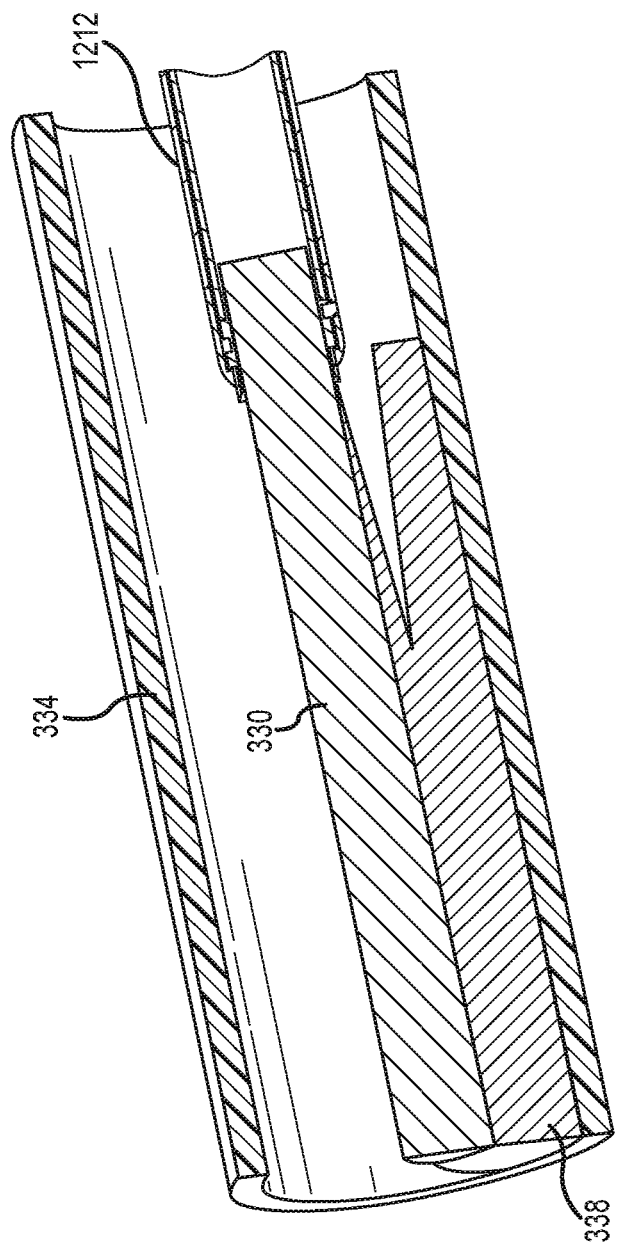
FIG. 14 is a cross-sectional view of a sheath assembly within a blood vessel with an extendable and rotatable blade for removing a lead according to an embodiment of the disclosure.

FIG. 14 depicts the distal portion of the flexible outer sheath and flexible inner sheath surrounding a lead 330 within a patient's vein 334 with the cutting tip 1632 in its extended position. The circumferential nature of the cutting surface (e.g., notched blade) at the distal end of the cutting tip 1632 causes the surgical device to act as a coring device, thereby cutting tissue 338 either partially (i.e., less than 360 degrees) or completely (i.e., 360 degrees) around the lead or implanted object being extracted. The amount of tissue that the cutting surface cuts depends upon the size, shape and configuration of the lead, as well as the diameter and thickness of the circular cutting blade. For example, if the diameter of the circular cutting surface is substantially greater than the diameter of the lead, then the cutting surface will cut and core more tissue in comparison to a cutting surface having a smaller diameter.

Although the inner sheath and outer sheath are coupled to one another via the cutting tip, the outer band, and the guide pin, the inner sheath assembly and outer sheath assembly may be coupled to one another in other ways. Stated differently, those of skill in the art will understand how to make and use the disclosed aspects, embodiments, and/or configurations after understanding the present disclosure to couple the sheaths in a manner to allow a cutting surface to extend and rotate beyond the distal end of the outer sheath. All such configurations within the knowledge of one skilled in the art are considered within the scope of this disclosure.

Figure 19A:
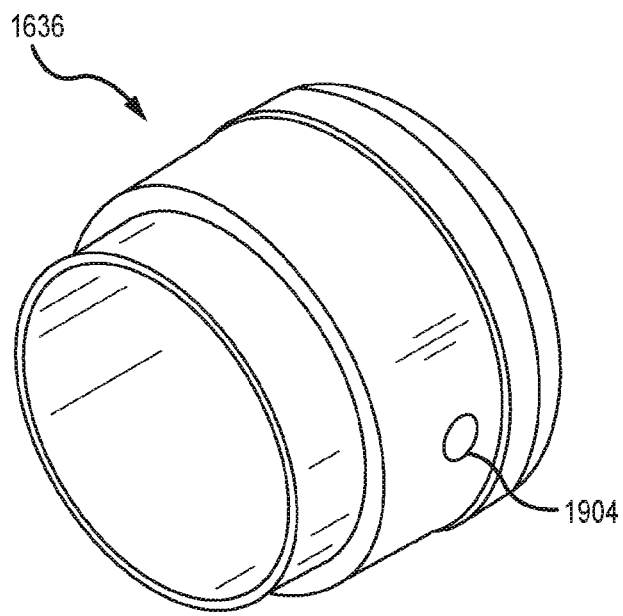
FIG. 19A is a perspective view of an outer band member according to an embodiment of the disclosure.
Figures 19B, 19C:
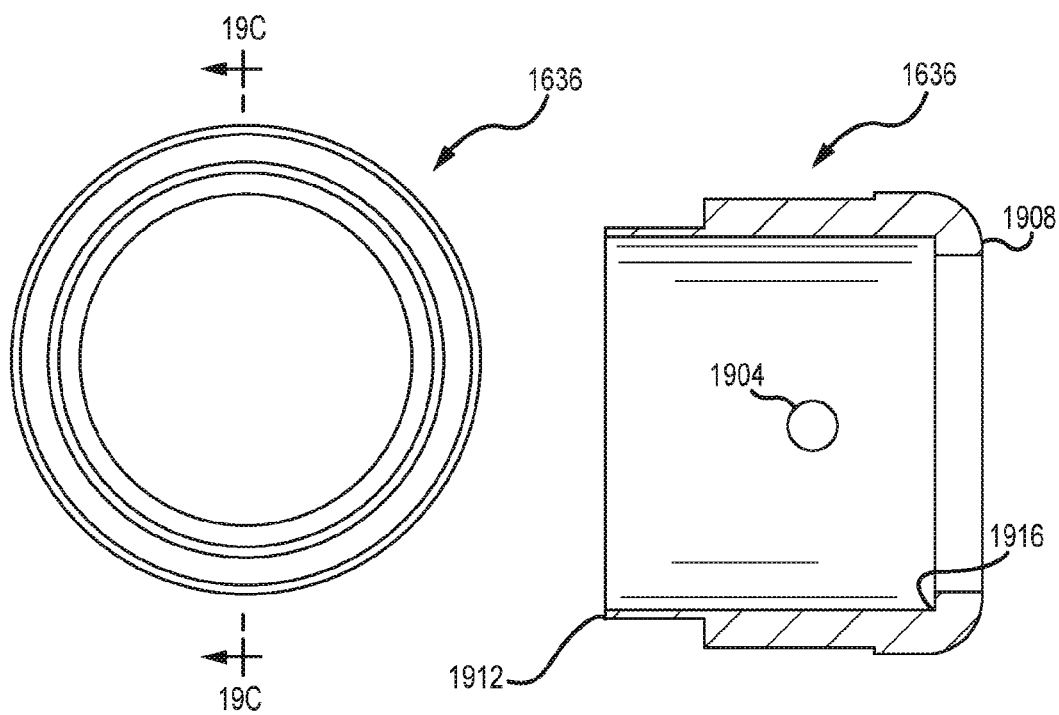
FIG. 19B is an end view of the outer band member illustrated in FIG. 19A.
FIG. 19C is cross-sectional view of the outer band member illustrated in FIG. 19A taken along line 19C-19C of FIG. 19B.

With reference to FIGS. 19A, 19B and 19C, an exemplary outer band 1636 is depicted. The outer band 1636 may be a sleeve in the general shape of a hollow cylinder. Although the exterior of the outer band 1636 is non-uniform, it may be uniform. The interior of the outer band 1636 is non-uniform. For example, the interior of the outer band 1636 includes an abutment 1916 to prevent the cutting tip (not shown in FIGS. 19A, 19B and 19C) from traveling further from the proximal end 1912 to the distal end 1908 within the outer band 1636. The outer band 1636 also includes a hole 1904 for receipt and possible attachment of a guide pin (not shown in FIGS. 19A, 19B and 19C) which protrudes radially inward. As discussed in more detail above, the guide pin engages the cam slot of the cutting tip. The size, shape and configuration of the outer band 1636 may differ depending upon how it is attached to the flexible outer sheath. As discussed above, the outer band 1636 may be stationary. If so, the outer band 1636 and the guide pin remain stationary as the cutting tip moves (e.g., rotates and travel longitudinally) relative thereto. The outer band may also contain a journal bearing surface to align the cutting blade during actuation and provide a surface to disengage the tissue at the retraction of the cutting blade within the device.

With reference to FIGS. 20A, 20B, 20C and 20D, an exemplary cutting tip 1632 is depicted. The cutting tip 1632 has a generally hollow cylindrical shape. The cutting tip 1632 comprises a proximal portion 2024, an intermediate portion 2028, and a distal portion 2032. The outside diameter of the proximal portion 2024 is sized to allow it to be inserted to and/or engage (or otherwise attached to) the interior diameter of the inner flexible sheath (not shown). The distal end of cutting tip 1632 comprises a cutting surface 2012 having a serrated, sharp blade profile. The intermediate portion 2028 comprises a channel (or cam slot) 2016 cut within its exterior surface. As the inner flexible sheath rotates and moves within the outer sheath—from its proximal end to distal end—the outer sheath and pin may remain stationary. If so, the inner sheath (not shown), which is connected to cutting tip 1632, forces the cutting tip 1632 to rotate. The cam slot 2016 engages the guide pin, and the shape and profile of the cam slot 2016 controls the rate and distance with which the cutting tip 1632 travels longitudinally. That is, the configuration of the cam slot 2016 controls the cutting tip's direction and amount of longitudinal travel, such as moving distally toward an extended position and/or proximally toward a retracted position, while the cutting tip rotates in either a clockwise or counter-clockwise direction.

Referring again to FIGS. 20A, 20B, 20C and 20D, the cutting tip 1632 may also comprise a step up 2020 such that the diameter of the intermediate portion 2028 is greater than the distal portion 2032. As the cutting tip 1632 rotates, and the cutting surface 2012 extends beyond the distal end of the outer band into an extended position, the step up 2020 of the cutting tip 1632 contacts the abutment of the outer band, thereby limiting the distance that the cutting tip 1632 may travel and/or may prevent the cutting tip 1632 from exiting or extending beyond the distal tip of the outer sheath assembly, particularly the outer band, in the event that the pin is sheared.

Figures 20A, 20B:
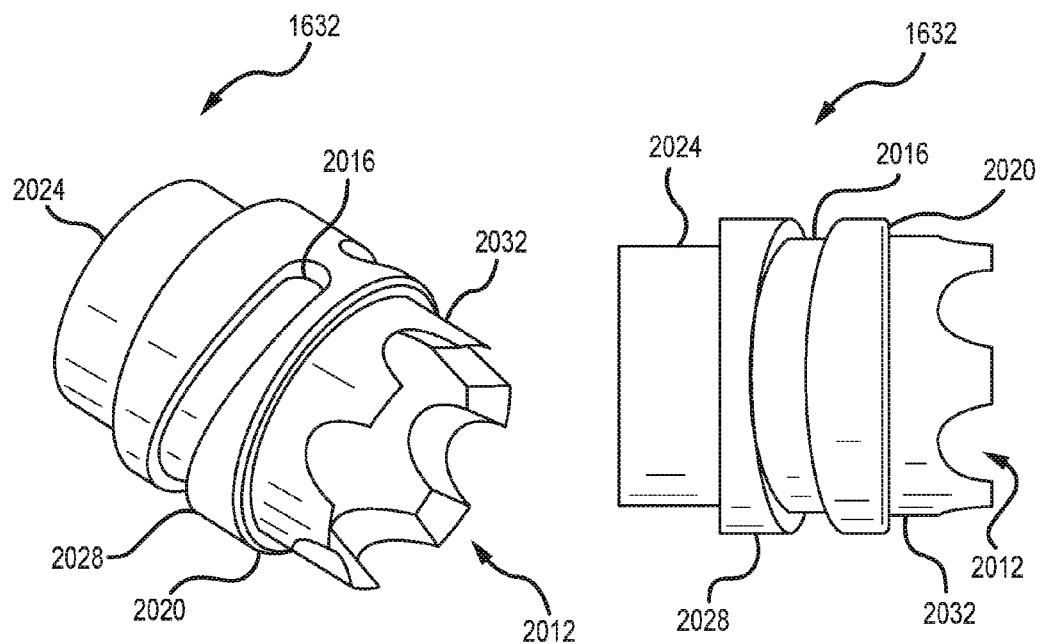
FIG. 20A is a perspective view of a cutting tip according to an embodiment of the disclosure.
FIG. 20B is side view of the cutting tip illustrated in FIG. 20A.
Figures 20C, 20D:
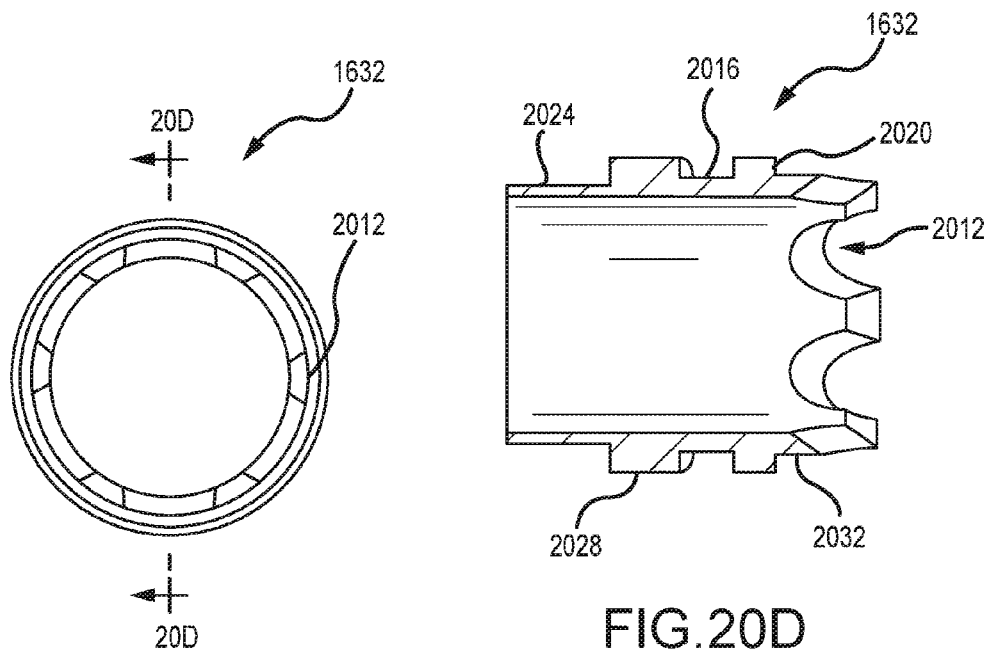
FIG. 20C is end view of the cutting tip member illustrated in FIG. 20A.
FIG. 20D is cross-sectional view of the cutting tip illustrated in FIG. 20A taken along line 20D-20D in FIG. 20C.

The profile of the cam slot in the cutting tip may have various configurations, such as those disclosed in U.S. patent application Ser. No. 13/834,405 filed Mar. 15, 2013 and entitled Retractable Blade For Lead Removal Device, which is hereby incorporated herein by reference in its entirety for all that it teaches and for all purposes. For example, the cam slot may have a substantially linear profile, a substantially sinusoidal profile, or a combination of individual and/or multiple linear and non-linear profiles. Additionally, the cam slot may have an open and continuous configuration, thereby allowing the cutting tip to continuously rotate, or the cam slot may have a closed and discontinuous configuration such that when the cutting tip reaches its fully extended position, the trigger assembly must be released or reversed so that the cutting tip returns to initially retracted position before being re-actuated. For instance, the cam slot 2016 in FIG. 20A is discontinuous because the cam slot does not travel around the entire circumference of the exterior of the cutting tip 1632. In some embodiments and as shown in FIGS. 21 and 22A-22C, the cam slot 2016 may be symmetric over a longitudinally-extending plane. Although certain figures in this disclosure only illustrate either the open or closed cam slot configuration, either configuration may be used with any of the inner cam embodiments disclosed and/or discussed herein and are considered within the scope of this disclosure. Furthermore, various types of cams, such as a partial lobe cam (which includes a cam slot surrounding less than 360 degrees of the circumference of the exterior surface of the cutting tip), a single lobe cam (which includes a cam slot surrounding 360 degrees of the circumference of the exterior surface of the cutting tip), double lobe cams (which includes a cam slot surrounding 720 degrees of the circumference of the exterior surface of the cutting tip) and/or other multiple lobe cams.

The distal end of cutting tip 1632 may comprise a cutting surface 2012 having different blade profiles, such as those disclosed in U.S. patent application Ser. No. 13/834,405 filed Mar. 15, 2013 and entitled Retractable Blade For Lead Removal Device, which is hereby incorporated herein by reference in its entirety for all that it teaches and for all purposes. For example, the plane of the cutting surface 2012 of the distal end of the cutting tip depicted in the figures of this disclosure is parallel to the plane of the proximal end of the cutting tip. The plane of the cutting surface, however, may be offset (0 degrees to 90 degrees) from the plane of the proximal end of the cutting tip. Also, as discussed above, the profile of the cutting surface 2012 in FIGS. 10A-10D has a plurality of serrations. The profile of the cutting surface 2012 need not be serrated and may comprise other configurations, such as a constant and/or smooth sharp profile. The profile of the cutting surface 2012 in FIGS. 20A-20D has a plurality of six (6) serrations. However, it may be preferable to have less than or more than six (6) serrations. It may also be preferable to have between five (5) and seven (7) serrations, or between four (4) and eight (8) serrations, or between six (6) and ten (10) serrations.

Although the cutting surface 2012 illustrates a certain number of serrations, FIGS. 20A-20D are not intended to represent the only number and type of serrations that may be included in a serrated cutting surface. Depending upon the size of the surgical device, including the sheaths, and cutting tip, those of skill in the art will understand how to make and use the disclosed aspects, embodiments, and/or configurations after understanding the present disclosure to adjust the number, size and configurations of the serrations. All such configurations within the knowledge of one skilled in the art are considered within the scope of this disclosure. Furthermore, the serrations may comprise a myriad of different shapes and configurations, including but not limited to any variation of a square, rectangle, rhombus, parallelogram, trapezoid, triangle, circle, ellipse, kite, etc.

Figure 21:
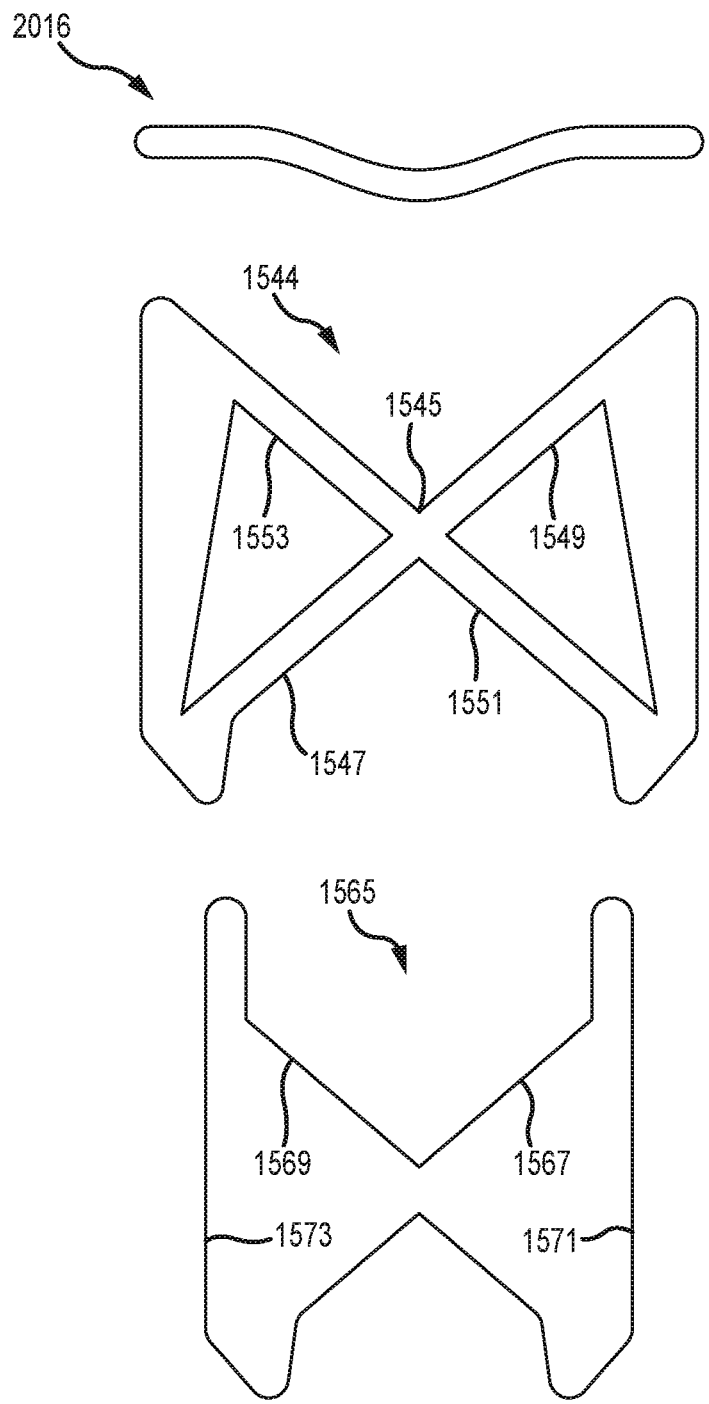
FIG. 21 depicts two-dimensional illustrations of a profile of a cam slot of an embodiment of a cutting tip, a profile of a cam slot of an embodiment of a barrel cam cylinder, and a profile of an aperture of an embodiment of a follower guide.
Figure 22A:
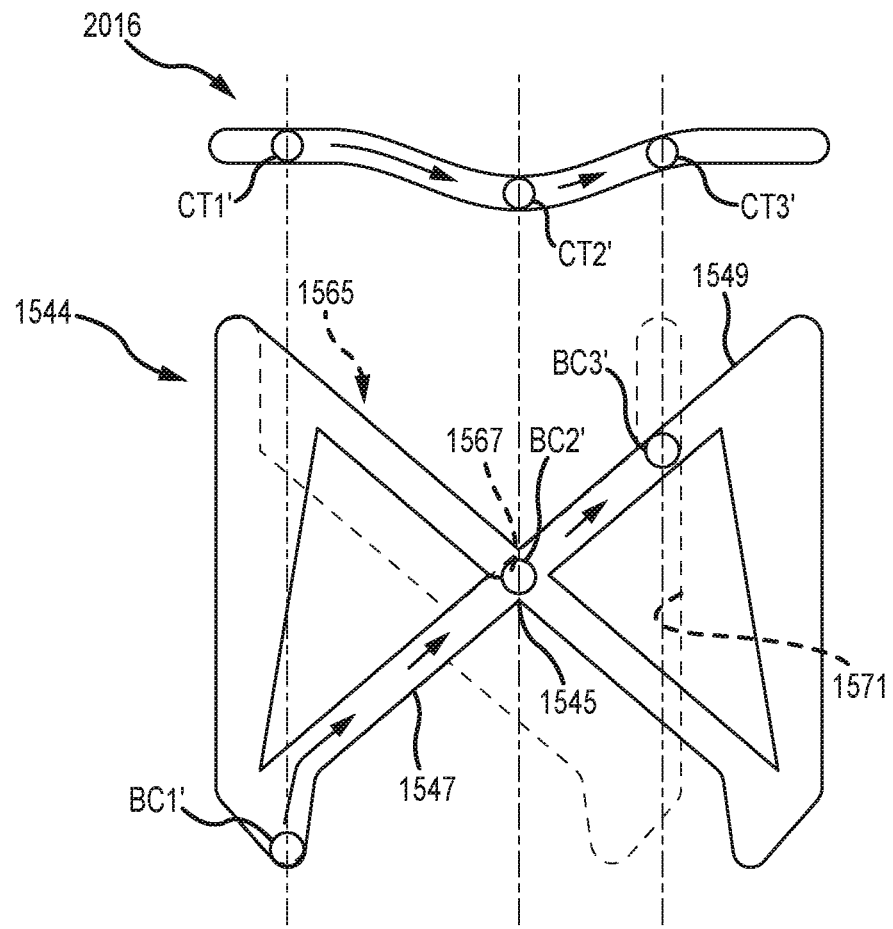
FIG. 22A is an illustration of the cam slot profile of the cutting tip, the cam slot of the barrel cam cylinder, and the profile of the aperture of the follower guide depicting the longitudinal position of the cutting tip in combination with the longitudinal position of the trigger for a particular amount of angular rotation by both the cutting tip and the barrel cam cylinder; the follower guide is illustrated in a first relative rotation-inhibiting position compared to the barrel cam cylinder.
Figure 22B:
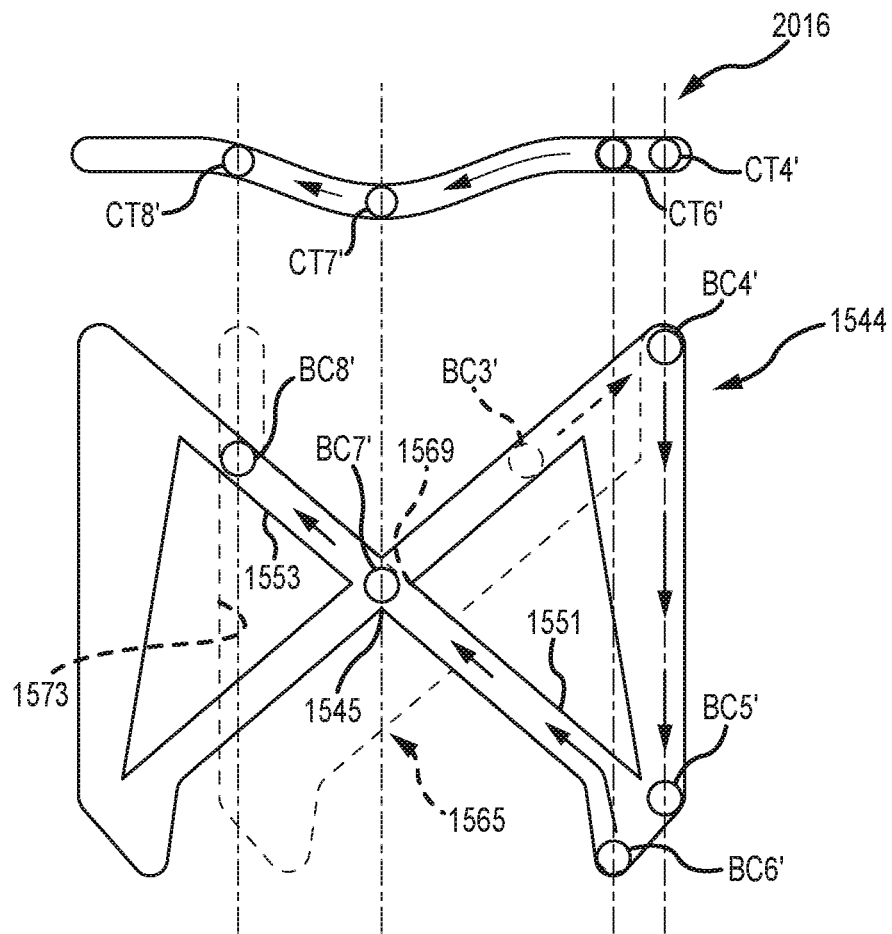
FIG. 22B is another illustration of the cam slot profile of the cutting tip, the cam slot of the barrel cam cylinder, and the profile of the aperture of the follower guide depicting the longitudinal position of the cutting tip in combination with the longitudinal position of the trigger for a particular amount of angular rotation by both the cutting tip and the barrel cam cylinder; the follower guide is illustrated in a second relative rotation-inhibiting position compared to the barrel cam cylinder.
Figure 22C:
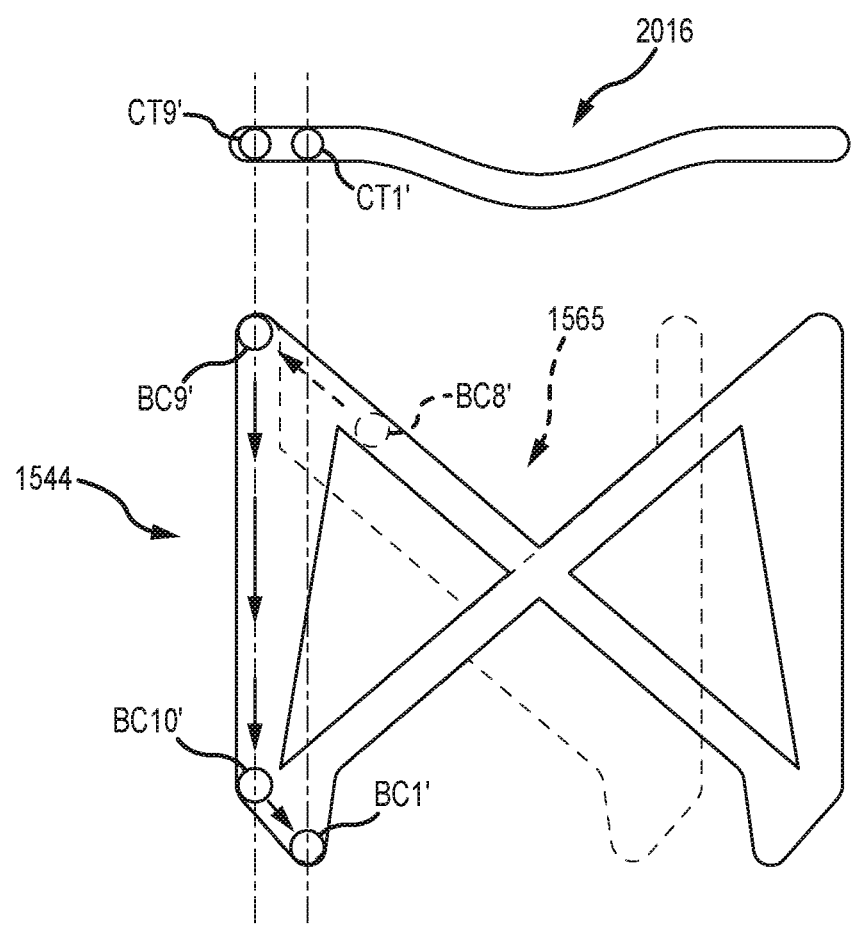
FIG. 22C is another illustration of the cam slot profile of the cutting tip, the cam slot of the barrel cam cylinder, and the profile of the aperture of the follower guide depicting the longitudinal position of the cutting tip in combination with the longitudinal position of the trigger for a particular amount of angular rotation by both the cutting tip and the barrel cam cylinder; the follower guide is again illustrated in the first relative rotation-inhibiting position compared to the barrel cam cylinder.

FIG. 21 depicts two-dimensional illustrations of the profile of the cam slot 2016 for the cutting tip 1632, the profile of the cam slot 1544 for the barrel cam cylinder 1520, and the profile of the aperture 1565 of the follower guide 1521. FIGS. 22A-22C depict the how actuation of the trigger 1508, and the resulting movement of the trigger pin 1528, results in rotational movement of the barrel cam cylinder 1520, the follower guide 1521, and the cutting tip 1632, and translation movement of the cutting tip 1632. In these figures, a horizontal axis for the profiles of the slots 2016 and 1544 is the degree(s) of rotation of the cutting tip 1632 and the barrel cam cylinder 1520. For example, assuming that the profile of the cam slot in the cutting tip 1632 is discontinuous, as depicted in FIG. 20A, the cutting tip 1632 will rotate less than 360 degrees. It may be preferable for the cutting tip 1632 to rotate between 5 and 355 degrees, 180 degrees and 355 degrees, 210 degrees and 325 degrees, 240 degrees and 295 degrees, or 270 degrees and 275 degrees. It may also be preferable for the cutting tip 1632 rotate about 180, 185, 190, 200, 205, 210, 215, 220, 225, 230, 235, 240, 245, 250, 255, 260, 265, 270, 275, 280, 285, 290, 300, 305, 310, 315, 320, 325, 330, 335, 340, 345, 350 or 355 degrees. A vertical axis for the profile of the cam slot 2016 for the cutting tip 1632 is the amount of longitudinal displacement, if any, of the cutting tip 1632. The vertical axis for the profile of the cam slot 1544 for the barrel cam cylinder 1520 is the amount of longitudinal displacement of the trigger assembly (and trigger pin 1528).

In FIGS. 22A-22C, the aperture 1565 of the follower guide 1521 is shown as a dashed line and is overlaid on the profile of the cam slot 1544 for the barrel cam cylinder 1520 to illustrate the rotational position of the aperture 1565 relative to the cam slot 1544. As shown in FIGS. 22A-22C and explained in further detail below, the rotational position of the aperture 1565 changes relative to the cam slot 1544 during actuation of the trigger 1508.

Generally, an initial, or first, actuation of the trigger 1508 (that is, pulling the trigger 1508 as far as permitted by the handle assembly and then releasing the trigger 1508 so that it returns to its home position) results in about a 254 degree rotational displacement of the cutting tip 1632 and the barrel cam cylinder 1520 in one direction—clockwise when looking from the handle to the tip. The first actuation also extends the cutting tip 1632 from the outer band 1636 and then returns the cutting tip 1632 to the sheathed position as the cutting tip 1632 rotates. A subsequent, or second, actuation of the trigger 1508 results in about a 254 degree rotational displacement of the cutting tip 1632 and the barrel cam cylinder 1520 in the opposite direction—counter-clockwise when looking from the handle to the tip. The second actuation also extends the cutting tip 1632 from the outer band 1636 and then returns the cutting tip 1632 to the sheathed position as the cutting tip 1632 rotates. Additional "odd" actuations (that is, a third actuation, a fifth actuation, and so on) cause the same device motions as the first actuation of the trigger 1508, and additional "even" actuations (that is, a fourth actuation, a sixth actuation, and so on) cause the same device motions as the second actuation of the trigger 1508.

The following discussion more specifically explains the interaction between the rotation of the barrel cam cylinder 1520, the rotation of the follower guide 1521, the rotation of the cutting tip 1632, the longitudinal movement of the handle (via the position of the trigger pin 1528), and the longitudinal movement of the cutting tip 1632.

First and referring specifically to FIGS. 22A, 23A, 23B, and 23C, the following is a description of the positions BC1'-BC3' of the trigger pin 1528 within the cam slot 1544 of the barrel cam cylinder 1520. In these positions, the follower guide 1521 is in the first relative rotation-inhibiting position, and the follower guide 1521 rotates together with the barrel cam cylinder 1520.

BC1'—The trigger pin 1528 is at a first home position within the cam slot of the barrel cam cylinder 1520. The trigger 1508 of the trigger assembly is also at its home position.

BC2'—The trigger pin 1528 has moved longitudinally in a proximal direction, thereby causing the barrel cam cylinder 1520 to rotate in a clockwise direction. The trigger pin 1528 engages the first diagonally-extending wall 1567 of the aperture 1565 of the follower guide 1521.

BC3'—The trigger pin 1528 has moved longitudinally further in the proximal direction, thereby causing the barrel cam cylinder 1520 to rotate further in the clockwise direction. The trigger pin 1528 engages the first longitudinally-extending wall 1571 of the aperture 1565 of the follower guide 1521.

The positions BC1'-BC3' of the trigger pin 1528 within the cam slot 1544 of the barrel cam cylinder 1520 correspond to positions CT1'-CT3' of the guide pin 1640 within the cam slot of the cutting tip 1632. The following is a description of the positions CT1'-CT3' of the guide pin 1640 within the cam slot of the cutting tip 1632.

CT1'—The guide pin 1640 is at a first home position within the cam slot 2016 of the cutting tip 1632, and the cutting tip 1632 is in a retracted position within the outer sheath assembly 1602 (including the outer band 1636).

CT2'—The cutting tip 1632 has rotated in a clockwise direction over the guide pin 1640 within the cam slot 2016 for about half of its predetermined rotation. The cutting tip 1632 may be in its most extended position outside the outer sheath assembly 1602.

CT3'—The cutting tip 1632 has rotated further in the clockwise direction over the guide pin 1640 within the cam slot 2016. The cutting tip 1632 may be in an intermediate position between the extended position and the retracted position within the outer sheath assembly 1602, or the cutting tip 1632 may be in the retracted position within the outer sheath assembly 1602.

By beginning a first actuation of the trigger 1508 as described above, the trigger pin 1528 moves from its first home position BC1' and into the intersection 1545 of the cam slot 1544 of the barrel cam cylinder 1520 (position BC2'). This action causes the barrel cam cylinder 1520 and the cutting tip 1632 to rotate in a clockwise direction by about 127 degrees. In position BC2', the trigger pin 1528 engages the first diagonally-extending wall 1567 of the aperture 1565 of the follower guide 1521 to ensure that the trigger pin 1528 travels straight through the intersection 1545 of the cam slot 1544 of the barrel cam cylinder 1520. Stated another way, the trigger pin 1528 travels from the first leg 1547 of the cam slot 1544 to the second leg 1549 of the cam slot 1544. Stated yet another way, the follower guide 1521 ensures that that trigger pin 1528 traverses a first slot portion defined by the first leg 1547 and the second leg 1549. This ensures that the barrel cam cylinder 1520 continues to rotate in a clockwise direction. Engagement of the trigger pin 1528 against the wall of the aperture 1565 of the follower guide 1521 tends to rotate the follower guide 1521 in a clockwise direction relative to the barrel cam cylinder 1520. However, such motion is inhibited by the relative rotation-inhibiting mechanism 1575 in the first relative rotation-inhibiting position.

By continuing the first actuation of the trigger 1508, the trigger 1508 pin moves from position BC2' to position BC3'. This action causes the barrel cam cylinder 1520 and the cutting tip 1632 to rotate in the clockwise direction by about 50 degrees. In position BC3', the trigger pin 1528 engages the first longitudinally-extending wall 1571 of the aperture 1565 of the follower guide 1521. As described in further detail below, movement of the trigger pin 1528 past position BC3' rotates the follower guide 1521 in a counter-clockwise direction relative to the barrel cam cylinder 1520.

Figure 23A:
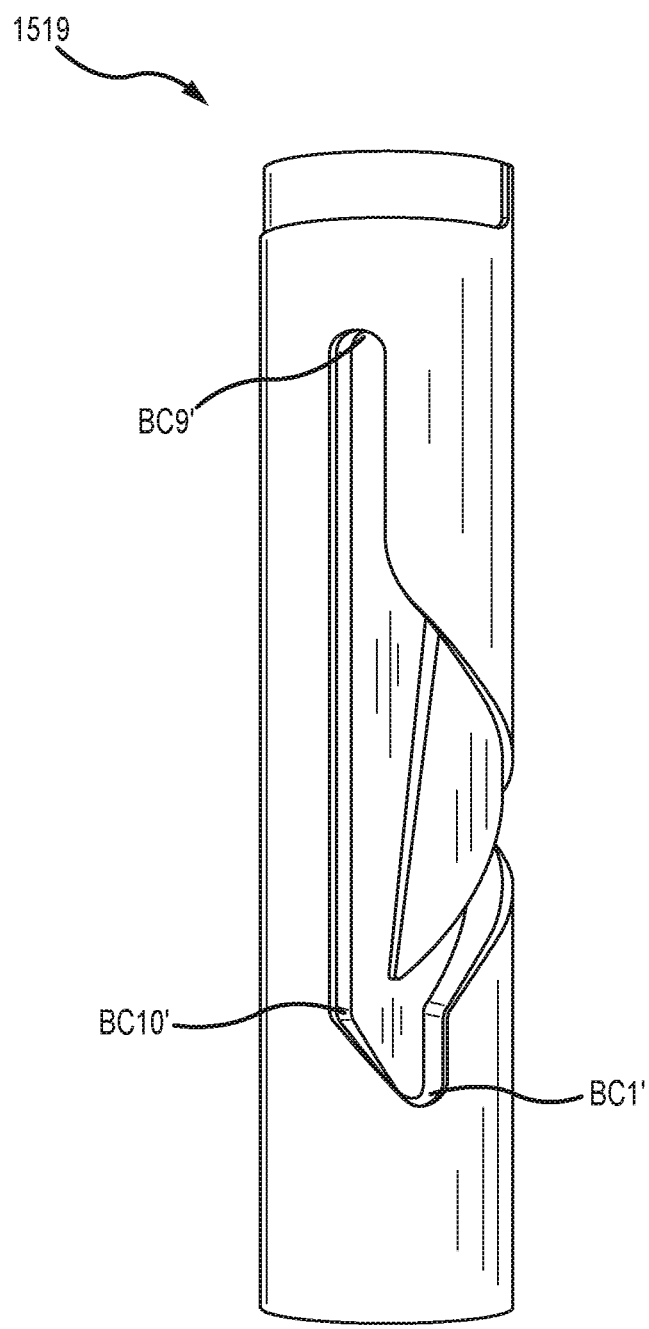
FIG. 23A is an elevation view of the barrel cam assembly illustrated in FIG. 15C in its first home position.
Figure 23B:
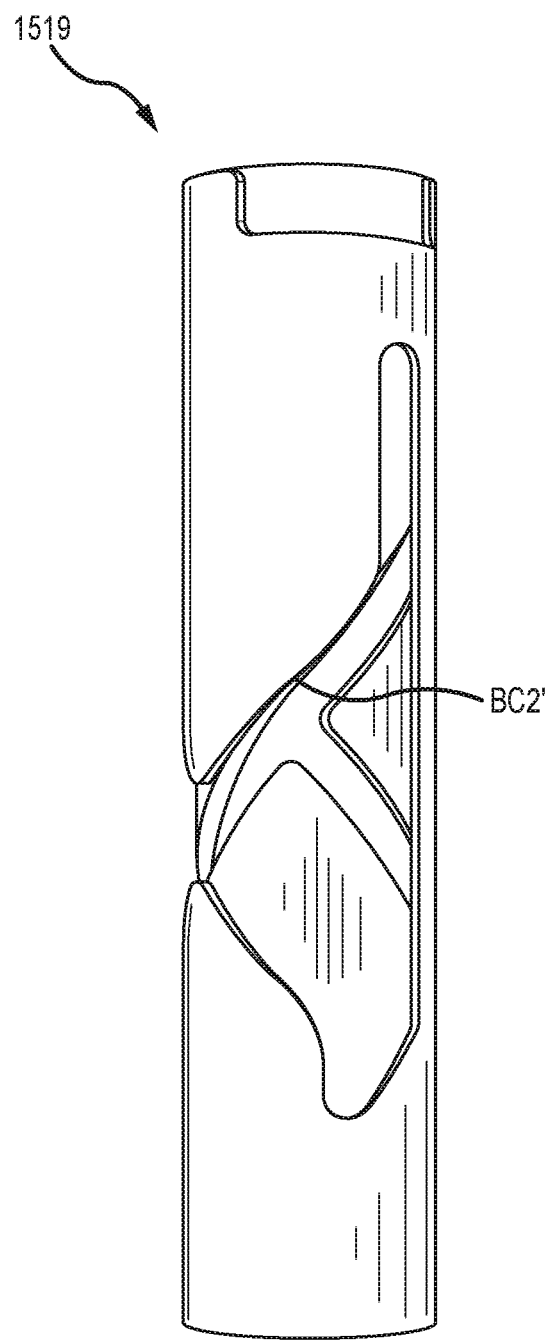
FIG. 23B is an elevation view of the barrel cam assembly illustrated in FIG. 15C upon being rotated away from its first home position.
Figure 23C:
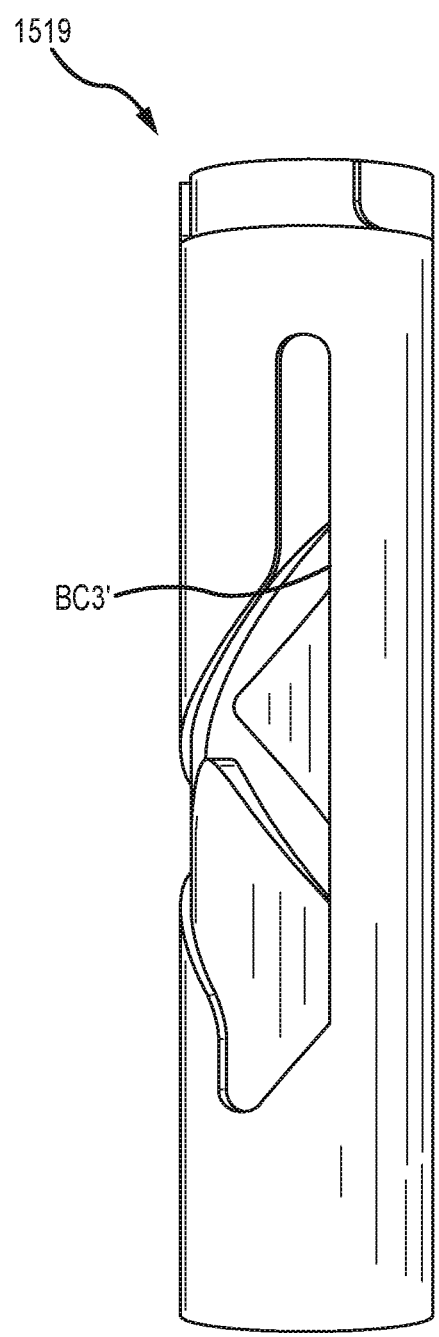
FIG. 23C is an elevation view of the barrel cam assembly illustrated in FIG. 15C upon being rotated further away from its first home position.
Figure 23D:
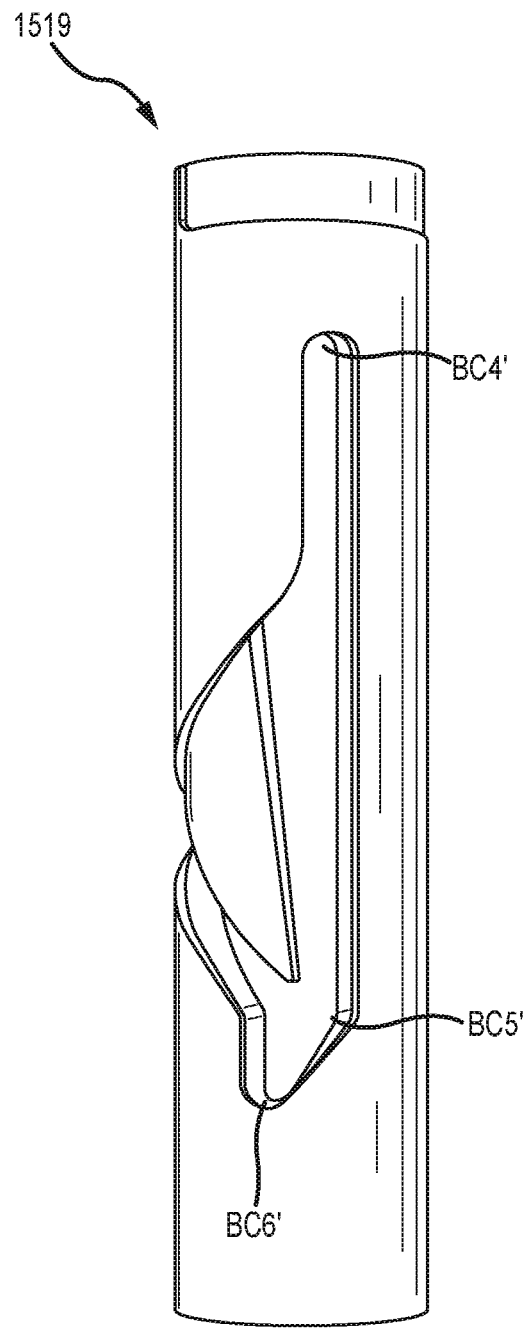
FIG. 23D is an elevation view of the barrel cam assembly illustrated in FIG. 15C in its second home position.

Referring now to FIGS. 22B and 23D, the following is a description of the positions BC4'-BC6' of the trigger pin 1528 within the cam slot 1544 of the barrel cam cylinder 1520. In these positions, the follower guide 1521 is in the second relative rotation-inhibiting position, and the follower guide 1521 rotates together with the barrel cam cylinder 1520.

BC4'—The trigger pin 1528 has moved about its entire longitudinal movement in a proximal direction and the barrel cam cylinder 1520 has completed its rotation in a clockwise direction. The trigger pin 1528 has rotated the follower guide 1521 to the second relative rotation-inhibiting position.

BC5'—The trigger pin 1528 has moved longitudinally in a distal direction. The barrel cam cylinder 1520 has remained stationary.

BC6'—The trigger pin 1528 has moved longitudinally further in the distal direction. The trigger pin 1528 is at a second home position within the cam slot of the barrel cam cylinder 1520. The trigger 1508 of the trigger assembly is also at its home position.

The positions BC4'-BC6' of the trigger pin 1528 within the cam slot of the barrel cam cylinder 1520 correspond to positions CT4'-CT6' of the guide pin 1640 within the cam slot of the cutting tip 1632. The following is a description of the positions CT4'-CT6' of the guide pin 1640 within the cam slot of the cutting tip 1632.

CT4'—The cutting tip 1632 has completed its rotation in a clockwise direction over the guide pin 1640 within the cam slot 2016. The cutting tip 1632 is in its most retracted position within the outer sheath assembly 1602.

CT5'—(Not shown) the cutting tip 1632 has not moved relative to position CT4'.

CT6'—The guide pin 1640 is at a second home position within the cam slot 2016 of the cutting tip 1632, and the cutting tip 1632 is in a retracted position within the outer sheath assembly 1602 (including the outer band 1636).

By continuing the first actuation of the trigger 1508, the trigger pin 1528 moves from position BC3' (FIG. 22A) to position BC4'. This action causes the barrel cam cylinder 1520 and the cutting tip 1632 to rotate in the clockwise direction by about 110 degrees. This action also causes the trigger pin 1528 to rotate the follower guide 1521 in a counter-clockwise direction by about 110 degrees relative to the barrel cam cylinder 1520. That is, the follower guide 1521 rotates from the first relative rotation-inhibiting position to the second relative rotation-inhibiting position. In the second relative rotation-inhibiting position, the follower guide 1521 is positioned to ensure that the trigger pin 1528 subsequently crosses its previous path and travels straight through the intersection 1545 of the cam slot 1544 of the barrel cam cylinder 1520.

After the trigger pin 1528 reaches position BC4', the trigger 1508 is moved in a distal direction (for example, by releasing the trigger 1508). This action causes the trigger pin 1528 to move from position BC4' to position BC5' and then position BC6'. When the trigger pin 1528 moves from position BC5' to position BC6', the barrel cam cylinder 1520 and the cutting tip 1632 rotate in the counter-clockwise direction by about 33 degrees. As such, the barrel cam cylinder 1520 and the cutting tip 1632 are rotationally displaced by about 254 degrees in the clockwise direction as the trigger pin 1528 moves from position BC1' to position BC6'. The trigger pin 1528 remains at position BC6', the second home position thereof, until the clinician begins a second actuation of the trigger 1508.

Figure 23E:
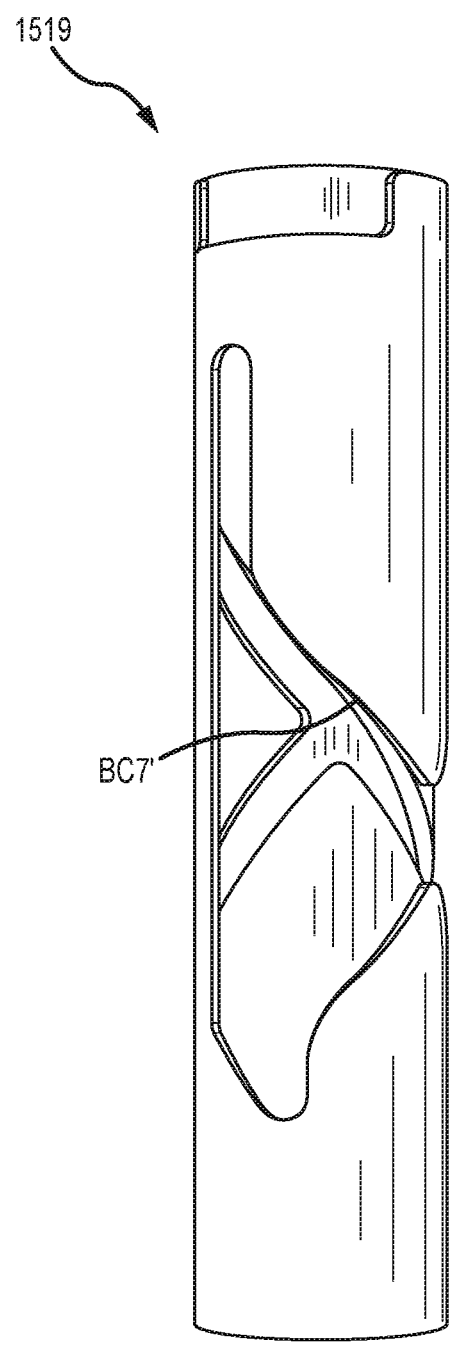
FIG. 23E is an elevation view of the barrel cam assembly illustrated in FIG. 15C upon being rotated away from its second home position.
Figure 23F:
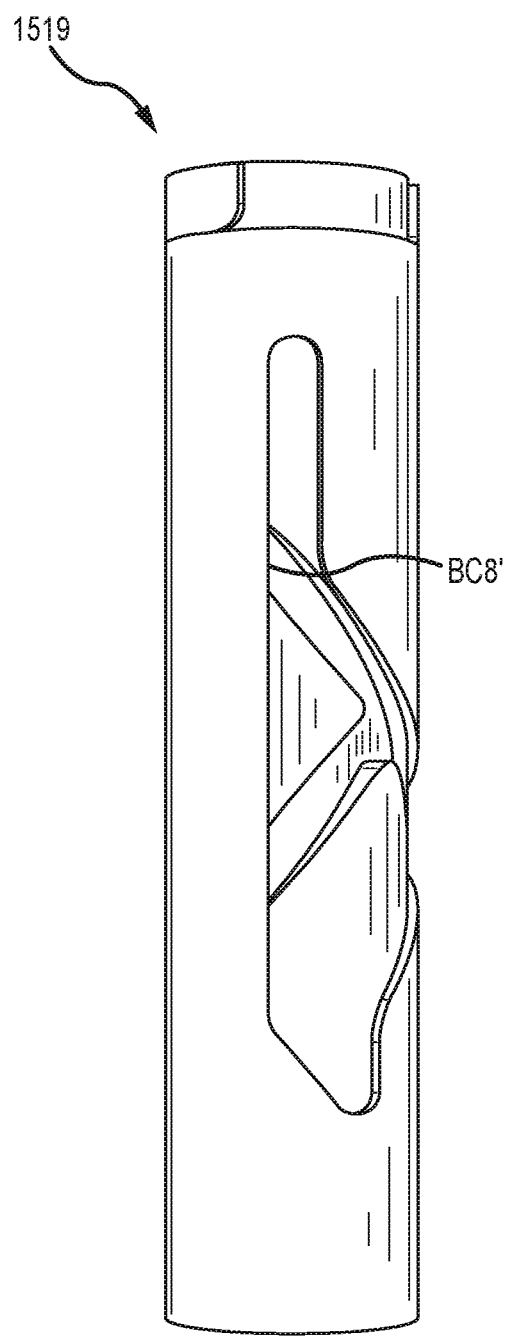
FIG. 23F is an elevation view of the barrel cam assembly illustrated in FIG. 15C upon being rotated further away from its second home position.

Referring now to FIGS. 22B, 23E, and 23F, the following is a description of the positions BC7'-BC8' of the trigger pin 1528 within the cam slot 1544 of the barrel cam cylinder 1520. In these positions, the follower guide 1521 is in the second relative rotation-inhibiting position, and the follower guide 1521 rotates together with the barrel cam cylinder 1520.

BC7'—The trigger pin 1528 has moved longitudinally in a proximal direction, thereby causing the barrel cam cylinder 1520 to rotate in a counter-clockwise direction. The trigger pin 1528 engages the second diagonally-extending wall 1569 of the aperture 1565 of the follower guide 1521.

BC8'—The trigger pin 1528 has moved longitudinally further in the proximal direction, thereby causing the barrel cam cylinder 1520 to rotate further in the counter-clockwise direction. The trigger pin 1528 engages the second longitudinally-extending wall 1573 of the aperture 1565 of the follower guide 1521.

The positions BC7'-BC8' of the trigger pin 1528 within the cam slot of the barrel cam cylinder 1520 correspond to positions CT7'-CT8' of the guide pin 1640 within the cam slot of the cutting tip 1632. The following is a description of the positions CT7'-CT8' of the guide pin 1640 within the cam slot of the cutting tip 1632.

CT7'—The cutting tip 1632 has rotated in a counter-clockwise direction over the guide pin 1640 within the cam slot 2016 for about half of its predetermined rotation. The cutting tip 1632 may be in its most extended position outside the outer sheath assembly 1602.

CT8'—The cutting tip 1632 has rotated further in the counter-clockwise direction over the guide pin 1640 within the cam slot 2016. The cutting tip 1632 may be in an intermediate position between the extended position and the retracted position within the outer sheath assembly 1602, or the cutting tip 1632 may be in the retracted position within the outer sheath assembly 1602.

By beginning a second actuation of the trigger 1508 as described above, the trigger pin 1528 moves from its second home position BC6' and into the intersection 1545 of the cam slot 1544 of the barrel cam cylinder 1520 (position BC7'). This action causes the barrel cam cylinder 1520 and the cutting tip 1632 to rotate in a counter-clockwise direction by 127 degrees. In position BC7', the trigger pin 1528 engages the second diagonally-extending wall 1569 of the aperture 1565 of the follower guide 1521 to ensure that the trigger pin 1528 travels straight through the intersection 1545 of the cam slot 1544 of the barrel cam cylinder 1520. Stated another way, the trigger pin 1528 travels from the third leg 1551 of the cam slot 1544 to the fourth leg 1553 of the cam slot 1544. Stated yet another way, the follower guide 1521 ensures that that trigger pin 1528 traverses a second slot portion defined by the third leg 1551 and the fourth leg 1553. This ensures that the barrel cam cylinder 1520 continues to rotate in a counter-clockwise direction. Engagement of the trigger pin 1528 against the wall of the aperture 1565 of the follower guide 1521 tends to rotate the follower guide 1521 in a counter-clockwise direction relative to the barrel cam cylinder 1520. However, such motion is inhibited by the relative rotation-inhibiting mechanism 1575 in the second relative rotation-inhibiting position.

By continuing the second actuation of the trigger 1508, the trigger 1508 pin moves from position BC7' to position BC8'. This action causes the barrel cam cylinder 1520 and the cutting tip 1632 to further rotate in the counter-clockwise direction by 50 degrees. In position BC8', the trigger pin 1528 engages the second longitudinally-extending wall 1573 of the aperture 1565 of the follower guide 1521. As described in further detail below, movement of the trigger pin 1528 past position BC8' rotates the follower guide 1521 in a clockwise direction relative to the barrel cam cylinder 1520.

Referring now to FIGS. 22C and 23A, the following is a description of the positions BC9'-BC10' of the trigger pin 1528 within the cam slot of the barrel cam cylinder 1520. In these positions, the follower guide 1521 is in the first relative rotation-inhibiting position, and the follower guide 1521 rotates together with the barrel cam cylinder 1520.

BC9'—The trigger pin 1528 has moved about its entire longitudinal movement in a proximal direction and the barrel cam cylinder 1520 has completed its rotation in a counter-clockwise direction. The trigger pin 1528 has rotated the follower guide 1521 back to the first relative rotation-inhibiting position.

BC10'—The trigger pin 1528 has moved longitudinally in a distal direction. The barrel cam cylinder 1520 has remained stationary.

The positions BC9'-BC10' of the trigger pin 1528 within the cam slot of the barrel cam cylinder 1520 correspond to positions CT9'-CT10' of the guide pin 1640 within the cam slot of the cutting tip 1632. The following is a description of the positions CT9'-CT10' of the guide pin 1640 within the cam slot of the cutting tip 1632.

CT9'—The cutting tip 1632 has completed its rotation in a counter-clockwise direction over the guide pin 1640 within the cam slot 2016. The cutting tip 1632 is in its most retracted position within the outer sheath assembly 1602.

CT10'—(Not shown) the cutting tip 1632 has not moved relative to position CT9'.

By continuing the second actuation of the trigger 1508, the trigger pin 1528 moves from position BC8' (FIG. 22B) to position BC9'. This action causes the barrel cam cylinder 1520 and the cutting tip 1632 to further rotate in the counter-clockwise direction by 110 degrees. This action also causes the trigger pin 1528 to rotate the follower guide 1521 in a clockwise direction relative to the barrel cam cylinder 1520 by 100 degrees. That is, the follower guide 1521 rotates from the second relative rotation-inhibiting position back to the first relative rotation-inhibiting position. In the first relative rotation-inhibiting position, the follower guide 1521 is again positioned to ensure that the trigger pin 1528 subsequently crosses its previous path and travels straight through the intersection 1545 of the cam slot 1544 of the barrel cam cylinder 1520.

After the trigger pin 1528 reaches position BC9', the trigger 1508 is moved in a distal direction (for example, by releasing the trigger 1508). This action causes the trigger pin 1528 to move from position BC9' to position BC10' and then position BC1'. When the trigger pin 1528 moves from position BC10' to position BC1', the barrel cam cylinder 1520 and the cutting tip 1632 rotate in the clockwise direction by about 33 degrees. As such, the barrel cam cylinder 1520 and the cutting tip 1632 are rotationally displaced by about 254 degrees in the counter-clockwise direction as the trigger pin 1528 moves from position BC6' to position BC1'.

The trigger pin 1528 remains at position BC1', the first home position thereof, until the clinician begins a third actuation of the trigger 1508. As described above, additional "odd" actuations (that is, a third actuation, a fifth actuation, and so on) of the trigger 1508 cause the same device motions as the first actuation of the trigger 1508, and additional "even" actuations (that is, a fourth actuation, a sixth actuation, and so on) of the trigger 1508 cause the same device motions as the second actuation of the trigger 1508.

Referring now to FIGS. 24-28, an exemplary barrel cam assembly 2419 is depicted. The barrel cam assembly 2419 may be used with a surgical device, such as the surgical device 1206 described above, in place of the barrel cam assembly 1519. The barrel cam assembly 2419 includes a barrel cam cylinder 2420 that rotatably carries a follower guide 2421. The barrel cam cylinder 2420 and the follower guide 2421 may have the same features as any of the barrel cam cylinders and the follower guides, respectively, described herein (for example, the cam groove 1544 and the follower aperture 1565, respectively), with the exception of the relative rotation-inhibiting mechanism.

The barrel cam assembly 2419 includes a relative rotation-inhibiting mechanism 2475 that inhibits some rotation of the follower guide 2421 relative to the barrel cam cylinder 2420. Generally, the relative rotation-inhibiting mechanism 2475 permits the follower guide 2421 to move from a first relative rotation-inhibiting position (referred to as the "first locked position" for simplicity) to a second relative rotation-inhibiting position (referred to as the "first locked position" for simplicity) and vice versa. In the first locked position, the mechanism 2475 initially inhibits the follower guide 2421 from rotating in a first direction relative to the barrel cam cylinder 2420 (that is, toward the second locked position) and inhibits rotation of the follower guide 2421 in a second direction relative to the barrel cam cylinder 2420. In the second locked position, the mechanism 2475 initially inhibits the follower guide 2421 from rotating in the second direction relative to the barrel cam cylinder 2420 (that is, toward the first locked position) and inhibits rotation of the follower guide 2421 in the first direction relative to the barrel cam cylinder 2420.

The relative rotation-inhibiting mechanism 2475 includes a radially-outwardly projecting protrusion 2402 formed near the proximal end of the barrel cam cylinder 2420. The protrusion 2402 may be formed on the barrel cam cylinder 2420 in a machining process. The protrusion 2402 includes a proximally-facing curved recess 2404. The protrusion 2402 also includes a first transversely-facing engagement surface 2406 and a second transversely-facing engagement surface 2408.

The relative rotation-inhibiting mechanism 2475 also includes a first spring prong 2410, a second spring prong 2412 (see FIG. 25), a first transversely-facing engagement surface 2413, and a second transversely-facing engagement surface 2414 (see FIG. 25) formed near the proximal end of the follower guide 2421. The spring prongs 2410, 2412 and the engagement surfaces 2413, 2414 may be formed on the follower guide 2421 in a laser cutting process.

The first spring prong 2410 is cantilevered from the remainder of the follower guide 2421 and extends partially about the circumference of the follower guide 2421. The first spring prong 2410 includes a curved tip 2418 that selectively engages the curved recess 2404 of the protrusion 2402 to inhibit rotation of the follower guide 2421 relative to the barrel cam cylinder 2420. This aspect is described in further detail below. In some embodiments, the curved tip 2418 has a radius of about 0.040 inches and 0.015 inches of interference with the curved recess 2404 of the protrusion 2402. Such dimensions facilitate both securement and slidable detachment of the first spring prong 2410 relative to the protrusion 2402.

The second spring prong 2412 is cantilevered from the remainder of the follower guide 2421. The second spring prong 2412 extends partially about the circumference of the follower guide 2421 and faces in the opposite circumferential direction as the first spring prong 2410. The second spring prong 2412 includes a curved tip 2422 that selectively engages the curved recess 2404 of the protrusion 2402 to inhibit rotation of the follower guide 2421 relative to the barrel cam cylinder 2420. This aspect is described in further detail below. In some embodiments, the curved tip 2422 has a radius of about 0.040 inches and 0.015 inches of interference with the curved recess 2404 of the protrusion 2402. Such dimensions facilitate both securement and slidable detachment of the second spring prong 2412 relative to the protrusion 2402.

Interaction of the first and second spring prongs 2410, 2412 with the protrusion 2402, and the resulting motion of the follower guide 2421 relative to the barrel cam cylinder 2420, are described with reference to the cam slot and aperture profiles illustrated in FIGS. 22A-22C. Referring first to FIG. 22A and upon a first actuation of the trigger assembly, the trigger pin initially moves from position BC1' to BC3'. As the trigger pin moves in this manner, the follower guide 2421 rotates together with the barrel cam cylinder 2420 because the curved tip 2418 of the first spring prong 2410 is engaged with the curved recess 2404 of the protrusion 2402. Stated another way, the first spring prong 2410 engages the protrusion 2402 to initially hold the follower guide 2421 in the first locked position relative to the barrel cam cylinder 2420.

Referring to FIG. 22B and by continuing the first actuation of the trigger assembly, the trigger pin moves from position BC3' to BC4'. In position BC3', the trigger pin engages the wall of the follower guide aperture. By moving toward position BC4', the trigger pin applies a force to the follower guide 2421 that causes the curved tip 2418 of the first spring prong 2410 to slip over and disengage the curved recess 2404 of the protrusion 2402. As a result, the follower guide 2421 is "unlocked" and rotates relative to the barrel cam cylinder 2420 as the trigger pin moves from position BC3' to BC4'. As the trigger pin approaches position BC4', the curved tip 2422 of the second spring prong 2412 slips over and engages the curved recess 2404 of the protrusion 2402. The follower guide 2421 thereby enters the second locked position relative to the barrel cam cylinder 2420.

When the user releases the trigger assembly, the trigger pin moves from position BC4' to BC6'. As the trigger pin moves in this manner, the follower guide 2421 rotates together with the barrel cam cylinder 2420 because the curved tip 2422 of the second spring prong 2412 is engaged with the curved recess 2404 of the protrusion 2402. Stated another way, the second spring prong 2412 engages the protrusion 2402 to hold the follower guide 2421 in the second locked position relative to the barrel cam cylinder 2420 after the first actuation of the trigger assembly.

Still referring to FIG. 22B and upon a second actuation of the trigger assembly, the trigger pin initially moves from position BC6' to BC8'. As the trigger pin moves in this manner, the follower guide 2421 rotates together with the barrel cam cylinder 2420 because the curved tip 2422 of the second spring prong 2412 is engaged with the curved recess 2404 of the protrusion 2402. Stated another way, the second spring prong 2412 engages the protrusion 2402 to initially hold the follower guide 2421 in the second locked position relative to the barrel cam cylinder 2420.

Referring to FIG. 22C and by continuing the second actuation of the trigger assembly, the trigger pin moves from position BC8' to BC9'. In position BC8', the trigger pin engages the wall of the follower guide aperture. By moving toward position BC9', the trigger pin applies a force to the follower guide 2421 that causes the curved tip 2422 of the second spring prong 2412 to slip over and disengage the curved recess 2404 of the protrusion 2402. As a result, the follower guide 2421 is "unlocked" and rotates relative to the barrel cam cylinder 2420 as the trigger pin moves from position BC8' to BC9'. As the trigger pin approaches position BC9', the curved tip 2418 of the first spring prong 2410 slips over and engages the curved recess 2404 of the protrusion 2402. The follower guide 2421 thereby returns to the first locked position relative to the barrel cam cylinder 2420.

When the user releases the trigger assembly, the trigger pin moves from position BC9' to BC1'. As the trigger pin moves in this manner, the follower guide 2421 rotates together with the barrel cam cylinder 2420 because the curved tip 2418 of the first spring prong 2410 is engaged with the curved recess 2404 of the protrusion 2402. Stated another way, the first spring prong 2410 engages the protrusion 2402 to hold the follower guide 2421 in the first locked position relative to the barrel cam cylinder 2420 after the second actuation of the trigger assembly.

In addition and as shown in FIG. 24, the first engagement surface 2413 of the follower guide 2421 engages the first engagement surface 2406 of the protrusion 2402 in the first locked position to inhibit the follower guide 2421 from rotating in a direction away from the second locked position. The second engagement surface 2414 of the follower guide 2421 engages the second engagement surface 2408 of the protrusion 2402 in the second locked position to inhibit the follower guide 2421 from rotating in a direction away from the first locked position.

Figure 29:
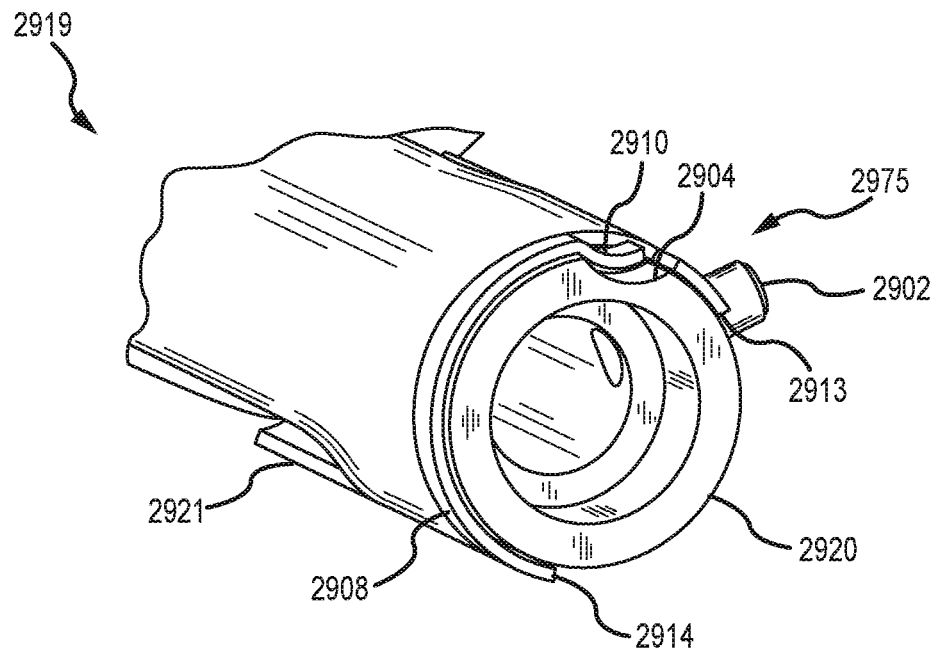
FIG. 29 is a partial perspective view of an embodiment of the barrel cam assembly for a surgical device.
Figure 30:
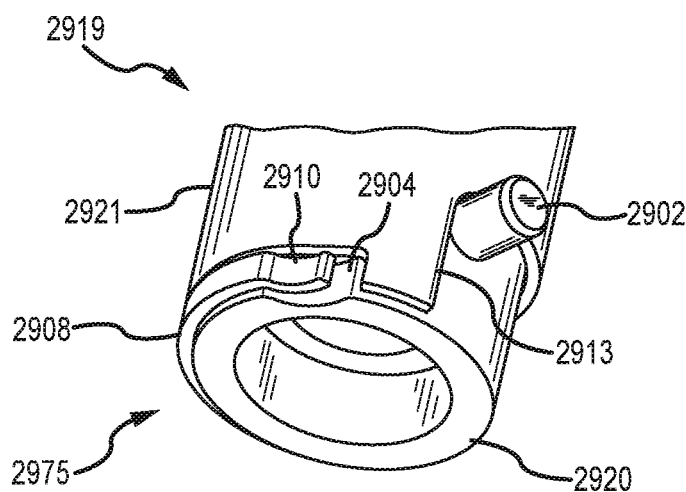
FIG. 30 is another partial perspective view of the barrel cam assembly of FIG. 29.

Referring now to FIGS. 29-30, an exemplary barrel cam assembly 2919 is depicted. The barrel cam assembly 2919 may be used with a surgical device, such as the surgical device 1206 described above, in place of the barrel cam assembly 1519. The barrel cam assembly 2919 includes a barrel cam cylinder 2920 that rotatably carries a follower guide 2921. The barrel cam cylinder 2920 and the follower guide 2921 may have the same features as any of the barrel cam cylinders and the follower guides, respectively, described herein (for example, the cam groove 1544 and the follower aperture 1565, respectively), with the exception of the relative rotation-inhibiting mechanism.

The barrel cam assembly 2919 includes a relative rotation-inhibiting mechanism 2975 that inhibits some rotation of the follower guide 2921 relative to the barrel cam cylinder 2920. Generally, the relative rotation-inhibiting mechanism 2975 permits the follower guide 2921 to move from a first relative rotation-inhibiting position (referred to as the "first locked position" for simplicity) to a second relative rotation-inhibiting position (referred to as the "first locked position" for simplicity) and vice versa. In the first locked position, the mechanism 2975 initially inhibits the follower guide 2921 from rotating in a first direction relative to the barrel cam cylinder 2920 (that is, toward the second locked position) and inhibits rotation of the follower guide 2921 in a second direction relative to the barrel cam cylinder 2920. In the second locked position, the mechanism 2975 initially inhibits the follower guide 2921 from rotating in the second direction relative to the barrel cam cylinder 2920 (that is, toward the first locked position) and inhibits rotation of the follower guide 2921 in the first direction relative to the barrel cam cylinder 2920.

The relative rotation-inhibiting mechanism 2975 includes a radially-outwardly projecting pin 2902 carried near the proximal end of the barrel cam cylinder 2920. The pin 2902 may be coupled to the barrel cam cylinder 2920 in various manners. For example, the pin 2902 may be press fitted or adhered in a hole formed on the barrel cam cylinder 2920. In some embodiments, the relative rotation-inhibiting mechanism 2975 also includes a radially outwardly-facing curved recess 2904 formed near the proximal end of the barrel cam cylinder 2920. The curved recess 2904 may be angularly offset from the pin 2902 about the longitudinal axis of the barrel cam cylinder 2920.

The relative rotation-inhibiting mechanism 2975 also includes a spring arm 2908, a first transversely-facing engagement surface 2913, and a second transversely-facing engagement surface 2914 formed near the proximal end of the follower guide 2921.

The spring arm 2908 is cantilever from the remainder of the follower guide 2921 at a first end. At an opposite end, the spring arm 2908 includes a radially inwardly-facing curved finger 2910. The finger 2910 selectively engages the curved recess 2904 of the barrel cam cylinder 2920 to inhibit rotation of the follower guide 2921 relative to the barrel cam cylinder 2920. This aspect is described in further detail below.

Interaction of the spring arm 2908 with the barrel cam cylinder 2920, and the resulting motion of the follower guide 2921 relative to the barrel cam cylinder 2920, are described with reference to the cam slot and aperture profiles illustrated in FIGS. 22A-22C. Referring first to FIG. 22A and upon a first actuation of the trigger assembly, the trigger pin initially moves from position BC1' to BC3'. As the trigger pin moves in this manner, the follower guide 2921 rotates together with the barrel cam cylinder 2920 because the finger 2910 is engaged with the curved recess 2904 of the barrel cam cylinder 2920. Stated another way, the finger 2910 engages the curved recess 2904 to initially hold the follower guide 2921 in the first locked position relative to the barrel cam cylinder 2920.

Referring to FIG. 22B and by continuing the first actuation of the trigger assembly, the trigger pin moves from position BC3' to BC4'. In position BC3', the trigger pin engages the wall of the follower guide aperture. By moving toward position BC4', the trigger pin applies a force to the follower guide 2921 that causes the finger 2910 to slip over and disengage the curved recess 2904 of the barrel cam cylinder 2920. As a result, the follower guide 2921 is "unlocked" and rotates relative to the barrel cam cylinder 2920 as the trigger pin moves from position BC3' to BC4'. The finger 2910 slips over and engages the outer surface of the barrel cam cylinder 2920 as the follower guide 2921 rotates relative to the barrel cam cylinder 2920. As the trigger pin approaches position BC4', the finger 2910 remains engaged with the curved recess 2904 of the barrel cam cylinder 2920. The follower guide 2921 thereby enters the second locked position relative to the barrel cam cylinder 2920.

When the user releases the trigger assembly, the trigger pin moves from position BC4' to BC6'. As the trigger pin moves in this manner, the follower guide 2921 rotates together with the barrel cam cylinder 2920 because the finger 2910 is engaged with the outer surface of the barrel cam cylinder 2920. Stated another way, the finger 2910 remains engaged with the outer surface of the barrel cam cylinder 2920 to hold the follower guide 2921 in the second locked position relative to the barrel cam cylinder 2920 after the first actuation of the trigger assembly.

Still referring to FIG. 22B and upon a second actuation of the trigger assembly, the trigger pin initially moves from position BC6' to BC8'. As the trigger pin moves in this manner, the follower guide 2921 rotates together with the barrel cam cylinder 2920 due to frictional forces between the finger 2910 and the outer surface of the barrel cam cylinder 2920. Stated another way, the finger 2910 engages the outer surface of the barrel cam cylinder 2920 to initially hold the follower guide 2921 in the second locked position relative to the barrel cam cylinder 2920.

Referring to FIG. 22C and by continuing the second actuation of the trigger assembly, the trigger pin moves from position BC8' to BC9'. In position BC8', the trigger pin engages the wall of the follower guide aperture. By moving toward position BC9', the trigger pin applies a force to the follower guide 2921 that overcomes the frictional forces between the finger 2910 and the outer surface of the barrel cam cylinder 2920. As a result, the finger 2910 slips over the outer surface of the barrel cam cylinder 2920, and the follower guide 2921 is "unlocked" and rotates relative to the barrel cam cylinder 2920 as the trigger pin moves from position BC8' to BC9'. As the trigger pin approaches position BC9', the finger 2910 slips over and engages the curved recess 2904 of barrel cam cylinder 2920. The follower guide 2921 thereby returns to the first locked position relative to the barrel cam cylinder 2920.

When the user releases the trigger assembly, the trigger pin moves from position BC9' to BC1'. As the trigger pin moves in this manner, the follower guide 2921 rotates together with the barrel cam cylinder 2920 because the finger 2910 is engaged with the curved recess 2904 of the barrel cam cylinder 2920. Stated another way, the finger 2910 engages the protrusion 2902 to hold the follower guide 2921 in the first locked position relative to the barrel cam cylinder 2920 after the second actuation of the trigger assembly.

In addition and as shown in FIG. 29, the first engagement surface 2913 of the follower guide 2921 engages the pin 2902 of the barrel cam cylinder 2920 in the first locked position to inhibit the follower guide 2921 from rotating in a direction away from the second locked position. The second engagement surface 2914 of the follower guide 2921 engages the pin 2902 in the second locked position to inhibit the follower guide 2921 from rotating in a direction away from the first locked position.

In some embodiments, the barrel cam cylinder 2920 includes a second radially outwardly-facing curved recess (not shown) that receives the finger 2910 in the second locked position of the follower guide 2921. In some embodiments, the barrel cam cylinder 2920 lacks any radially outwardly-facing curved recesses. Instead, the finger 2910 remains in engagement with the outer surface of the barrel cam cylinder 2920 in the first locked position, the second locked position, and the unlocked position.

Figure 31:
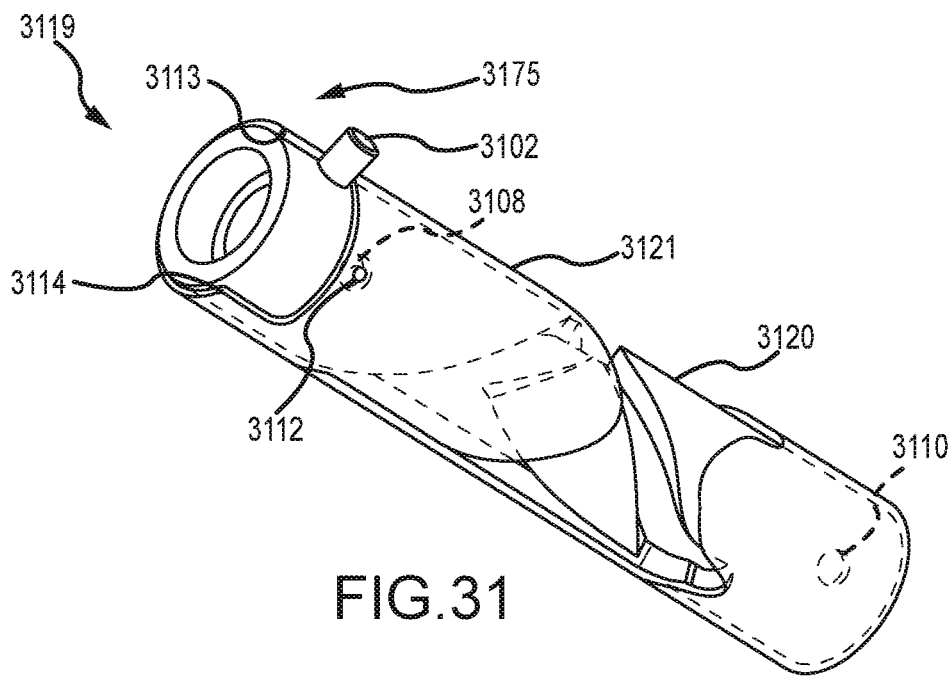
FIG. 31 is a perspective view of an embodiment of the barrel cam assembly for a surgical device; a follower guide of the barrel cam assembly is translucent for illustrative purposes.

Referring now to FIG. 31, an exemplary barrel cam assembly 3119 is depicted. The barrel cam assembly 3119 may be used with a surgical device, such as the surgical device 1206 described above, in place of the barrel cam assembly 1519. The barrel cam assembly 3119 includes a barrel cam cylinder 3120 that rotatably carries a follower guide 3121. The barrel cam cylinder 3120 and the follower guide 3121 may have the same features as any of the barrel cam cylinders and the follower guides, respectively, described herein (for example, the cam groove 1544 and the follower aperture 1565, respectively), with the exception of the relative rotation-inhibiting mechanism.

The barrel cam assembly 3119 includes a relative rotation-inhibiting mechanism 3175 that inhibits some rotation of the follower guide 3121 relative to the barrel cam cylinder 3120. Generally, the relative rotation-inhibiting mechanism 3175 permits the follower guide 3121 to move from a first relative rotation-inhibiting position (referred to as the "first locked position" for simplicity) to a second relative rotation-inhibiting position (referred to as the "first locked position" for simplicity) and vice versa. In the first locked position, the mechanism 3175 initially inhibits the follower guide 3121 from rotating in a first direction relative to the barrel cam cylinder 3120 (that is, toward the second locked position) and inhibits rotation of the follower guide 3121 in a second direction relative to the barrel cam cylinder 3120. In the second locked position, the mechanism 3175 initially inhibits the follower guide 3121 from rotating in the second direction relative to the barrel cam cylinder 3120 (that is, toward the first locked position) and inhibits rotation of the follower guide 3121 in the first direction relative to the barrel cam cylinder 3120.

The relative rotation-inhibiting mechanism 3175 includes a radially-outwardly projecting pin 3102 carried near the proximal end of the barrel cam cylinder 3120. The pin 3102 may be coupled to the barrel cam cylinder 3120 in various manners. For example, the pin 3102 may be press fitted or adhered in a hole formed on the barrel cam cylinder 3120.

The relative rotation-inhibiting mechanism 3175 also includes first and second spherical elements 3108 and 3110. The first and second spherical elements 3108 and 3110 are fixedly received in cylindrical blind holes formed in the outer surface of the barrel cam cylinder 3120. The first and second spherical elements 3108 and 3110 protrude from the holes to engage the inner surface of the follower guide 3121. As such, the first and second spherical elements 3108 and 3110 facilitate frictional engagement between the barrel cam cylinder 3120 and the follower guide 3121.

In some embodiments, the first and second spherical elements 3108 and 3110 are press fitted into the holes on the barrel cam cylinder 3120. In some embodiments, the first and second spherical elements 3108 and 3110 may be disposed near the proximal end and the distal end, respectively, of the barrel cam cylinder 3120. In some embodiments, the first and second spherical elements 3108 and 3110 are formed of steel, polyethylene, or the like. In some embodiments, the first and second spherical elements 3108 and 3110 are similar to the rolling elements, or balls, of a ball bearing.

The relative rotation-inhibiting mechanism 3175 further includes a first transversely-facing engagement surface 3113 and a second transversely-facing engagement surface 3114 formed near the proximal end of the follower guide 3121.

In some embodiments, the relative rotation-inhibiting mechanism 3175 further includes a through hole 3112 formed on the follower guide 3121. The through hole 3112 has a diameter that is smaller than the diameter of the first spherical element 3108. The through hole 3112 receives the first spherical element 3108 in the first locked position of the follower guide 3121. Entry of the first spherical element 3108 in the through hole 3112 provides tactile feedback to the device user.

Interaction of the first and second spherical elements 3108 and 3110 with the follower guide 3121, and the resulting motion of the follower guide 3121 relative to the barrel cam cylinder 3120, are described with reference to the cam slot and aperture profiles illustrated in FIGS. 22A-22C. Referring first to FIG. 22A and upon a first actuation of the trigger assembly, the trigger pin initially moves from position BC1' to BC3'. As the trigger pin moves in this manner, the follower guide 3121 rotates together with the barrel cam cylinder 3120 due to the frictional forces between the first and second spherical elements 3108 and 3110 and the follower guide 3121. Stated another way, the first and second spherical elements 3108 and 3110 initially hold the follower guide 3121 in the first locked position relative to the barrel cam cylinder 3120.

Referring to FIG. 22B and by continuing the first actuation of the trigger assembly, the trigger pin moves from position BC3' to BC4'. In position BC3', the trigger pin engages the wall of the follower guide aperture. By moving toward position BC4', the trigger pin applies a force to the follower guide 3121 that overcomes the frictional forces between the first and second spherical elements 3108 and 3110 and the follower guide 3121. As a result, the first and second spherical elements 3108 and 3110 slip against the follower guide 3121, and the follower guide 3121 is "unlocked" and rotates relative to the barrel cam cylinder 3120 as the trigger pin moves from position BC3' to BC4'. When the trigger pin reaches position BC4', the trigger pin no longer applies the force to the follower guide 3121.

When the user releases the trigger assembly, the trigger pin moves from position BC4' to BC6'. As the trigger pin moves in this manner, the follower guide 3121 rotates together with the barrel cam cylinder 3120 due to the frictional forces between the first and second spherical elements 3108 and 3110 and the follower guide 3121. Stated another way, the first and second spherical elements 3108 and 3110 hold the follower guide 3121 in the second locked position relative to the barrel cam cylinder 3120 after the first actuation of the trigger assembly.

Still referring to FIG. 22B and upon a second actuation of the trigger assembly, the trigger pin initially moves from position BC6' to BC8'. As the trigger pin moves in this manner, the follower guide 3121 rotates together with the barrel cam cylinder 3120 due to the frictional forces between the first and second spherical elements 3108 and 3110 and the follower guide 3121. Stated another way, the first and second spherical elements 3108 and 3110 initially hold the follower guide 3121 in the second locked position relative to the barrel cam cylinder 3120.

Referring to FIG. 22C and by continuing the second actuation of the trigger assembly, the trigger pin moves from position BC8' to BC9'. In position BC8', the trigger pin engages the wall of the follower guide aperture. By moving toward position BC9', the trigger pin applies a force to the follower guide 3121 that overcomes the frictional forces between the first and second spherical elements 3108 and 3110 and the follower guide 3121. As a result, the first and second spherical elements 3108 and 3110 slip against the follower guide 3121, and the follower guide 3121 is "unlocked" and rotates relative to the barrel cam cylinder 3120 as the trigger pin moves from position BC8' to BC9'. When the trigger pin reaches position BC9', the trigger pin no longer applies the force to the follower guide 3121.

When the user releases the trigger assembly, the trigger pin moves from position BC9' to BC1'. As the trigger pin moves in this manner, the follower guide 3121 rotates together with the barrel cam cylinder 3120 due to the frictional forces between the first and second spherical elements 3108 and 3110 and the follower guide 3121. Stated another way, the first and second spherical elements 3108 and 3110 hold the follower guide 3121 in the first locked position relative to the barrel cam cylinder 3120 after the second actuation of the trigger assembly.

In addition and as shown in FIG. 31, the first engagement surface 3113 of the follower guide 3121 engages the pin 3102 of the barrel cam cylinder 3120 in the first locked position to inhibit the follower guide 3121 from rotating in a direction away from the second locked position. The second engagement surface 3114 of the follower guide 3121 engages the pin 3102 in the second locked position to inhibit the follower guide 3121 from rotating in a direction away from the first locked position.

In some embodiments, the barrel cam assembly 3119 includes one spherical element, or three or more spherical elements. In some embodiments, one or more of the spherical elements 3108 and/or 3110 are received in through holes formed on the follower guide 3121 in the first and/or second locked positions. Entry of the spherical elements in the through holes provides tactile feedback to the device user.

Figure 32:
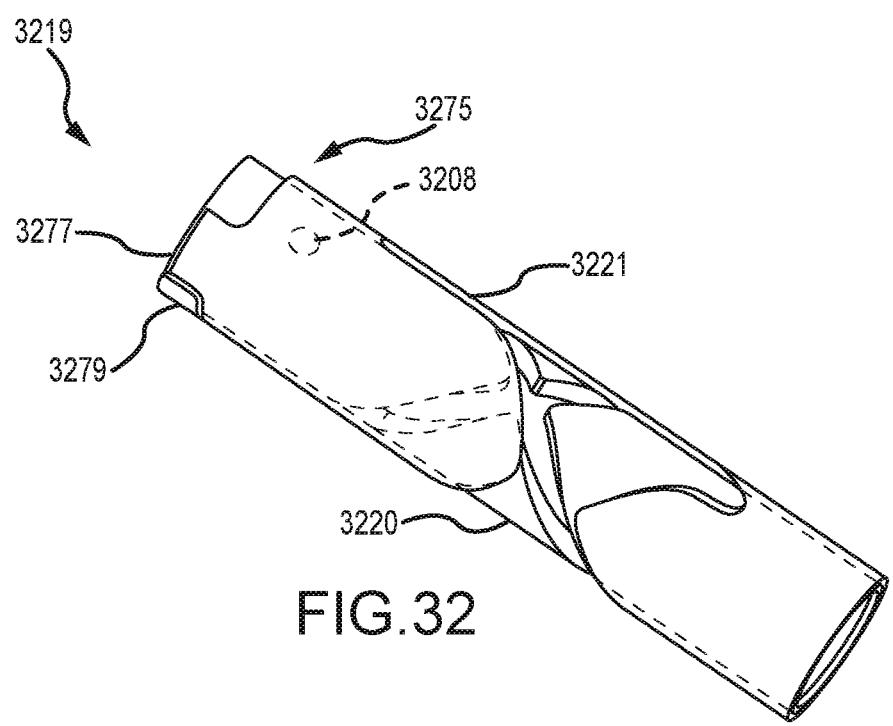
FIG. 32 is a perspective view of an embodiment of the barrel cam assembly for a surgical device; a follower guide of the barrel cam assembly is translucent for illustrative purposes.

Referring now to FIG. 32, an exemplary barrel cam assembly 3219 is depicted. The barrel cam assembly 3219 may be used with a surgical device, such as the surgical device 1206 described above, in place of the barrel cam assembly 1519. The barrel cam assembly 3219 includes a barrel cam cylinder 3220 that rotatably carries a follower guide 3221. The barrel cam cylinder 3220 and the follower guide 3221 may have the same features as any of the barrel cam cylinders and the follower guides, respectively, described herein (for example, the cam groove 1544 and the follower aperture 1565, respectively), with the exception of the relative rotation-inhibiting mechanism.

The barrel cam assembly 3219 includes a relative rotation-inhibiting mechanism 3275 that inhibits some rotation of the follower guide 3221 relative to the barrel cam cylinder 3220. Generally, the relative rotation-inhibiting mechanism 3275 permits the follower guide 3221 to move from a first relative rotation-inhibiting position (referred to as the "first locked position" for simplicity) to a second relative rotation-inhibiting position (referred to as the "first locked position" for simplicity) and vice versa. In the first locked position, the mechanism 3275 initially inhibits the follower guide 3221 from rotating in a first direction relative to the barrel cam cylinder 3220 (that is, toward the second locked position) and inhibits rotation of the follower guide 3221 in a second direction relative to the barrel cam cylinder 3220. In the second locked position, the mechanism 3275 initially inhibits the follower guide 3221 from rotating in the second direction relative to the barrel cam cylinder 3220 (that is, toward the first locked position) and inhibits rotation of the follower guide 3221 in the first direction relative to the barrel cam cylinder 3220.

The relative rotation-inhibiting mechanism 3275 includes a longitudinally extending tab 3277 formed near the proximal end of the follower guide 3221. The tab 3277 engages a semi-annular flange 3279 formed near the proximal end of the barrel cam cylinder 3220. As shown in FIG. 31, the tab 3277 engages one side of the flange 3279 in the first locked position to inhibit the follower guide 3221 from rotating in a direction away from the second locked position. The tab 3277 engages the other side of the flange 3279 in the second locked position to inhibit the follower guide 3221 from rotating in a direction away from the first locked position.

The relative rotation-inhibiting mechanism 3275 also includes a friction element 3208 that is fixedly carried by the barrel cam cylinder 3220. The friction element 3208 engages the follower guide 3221 to provide frictional engagement between the barrel cam cylinder 3220 and the follower guide 3221. In some embodiments, the friction element 3208 is formed by Teflon, polyethylene, nylon, or the like. In some embodiments, the friction element 3208 has a disk shape, a spring washer shape, or a wave washer shape. In some embodiments, the friction element 3208 is adhered to the barrel cam cylinder 3220.

Interaction of the friction element 3208 with the follower guide 3221, and the resulting motion of the follower guide 3221 relative to the barrel cam cylinder 3220, are described with reference to the cam slot and aperture profiles illustrated in FIGS. 22A-22C. Referring first to FIG. 22A and upon a first actuation of the trigger assembly, the trigger pin initially moves from position BC1' to BC3'. As the trigger pin moves in this manner, the follower guide 3221 rotates together with the barrel cam cylinder 3220 due to the frictional forces between the friction element 3208 and the follower guide 3221. Stated another way, the friction element 3208 initially holds the follower guide 3221 in the first locked position relative to the barrel cam cylinder 3220.

Referring to FIG. 22B and by continuing the first actuation of the trigger assembly, the trigger pin moves from position BC3' to BC4'. In position BC3', the trigger pin engages the wall of the follower guide aperture. By moving toward position BC4', the trigger pin applies a force to the follower guide 3221 that overcomes the frictional forces between the friction element 3208 and the follower guide 3221. As a result, the friction element 3208 slips against the follower guide 3221, and the follower guide 3221 is "unlocked" and rotates relative to the barrel cam cylinder 3220 as the trigger pin moves from position BC3' to BC4'. When the trigger pin reaches position BC4', the trigger pin no longer applies the force to the follower guide 3221.

When the user releases the trigger assembly, the trigger pin moves from position BC4' to BC6'. As the trigger pin moves in this manner, the follower guide 3221 rotates together with the barrel cam cylinder 3220 due to the frictional forces between the friction element 3208 and the follower guide 3221. Stated another way, the friction element 3208 holds the follower guide 3221 in the second locked position relative to the barrel cam cylinder 3220 after the first actuation of the trigger assembly.

Still referring to FIG. 22B and upon a second actuation of the trigger assembly, the trigger pin initially moves from position BC6' to BC8'. As the trigger pin moves in this manner, the follower guide 3221 rotates together with the barrel cam cylinder 3220 due to the frictional forces between the friction element 3208 and the follower guide 3221. Stated another way, the friction element 3208 initially holds the follower guide 3221 in the second locked position relative to the barrel cam cylinder 3220.

Referring to FIG. 22C and by continuing the second actuation of the trigger assembly, the trigger pin moves from position BC8' to BC9'. In position BC8', the trigger pin engages the wall of the follower guide aperture. By moving toward position BC9', the trigger pin applies a force to the follower guide 3221 that overcomes the frictional forces between the friction element 3208 and the follower guide 3221. As a result, the friction element 3208 slips against the follower guide 3221, and the follower guide 3221 is "unlocked" and rotates relative to the barrel cam cylinder 3220 as the trigger pin moves from position BC8' to BC9'. When the trigger pin reaches position BC9', the trigger pin no longer applies the force to the follower guide 3221.

When the user releases the trigger assembly, the trigger pin moves from position BC9' to BC1'. As the trigger pin moves in this manner, the follower guide 3221 rotates together with the barrel cam cylinder 3220 due to the frictional forces between the friction element 3208 and the follower guide 3221. Stated another way, the friction element 3208 holds the follower guide 3221 in the first locked position relative to the barrel cam cylinder 3220 after the second actuation of the trigger assembly.

In some embodiments, the barrel cam cylinder 3220 fixedly carries multiple friction elements. In some embodiments, the follower guide 3221 fixedly carries one or more friction elements that engage the outer surface of the barrel cam cylinder 3220.

Referring now to FIGS. 33 and 34, an exemplary barrel cam assembly 3319 is depicted. The barrel cam assembly 3319 may be used with a surgical device, such as the surgical device 1206 described above, in place of the barrel cam assembly 1519. The barrel cam assembly 3319 includes a barrel cam cylinder 3320 that rotatably carries a follower guide 3321. The barrel cam cylinder 3320 and the follower guide 3321 may have the same features as any of the barrel cam cylinders and the follower guides, respectively, described herein (for example, the cam groove 1544 and the follower aperture 1565, respectively), with the exception of the relative rotation-inhibiting mechanism.

The barrel cam assembly 3319 includes a relative rotation-inhibiting mechanism 3375 that inhibits some rotation of the follower guide 3321 relative to the barrel cam cylinder 3320. Generally, the relative rotation-inhibiting mechanism 3375 permits the follower guide 3321 to move from a first relative rotation-inhibiting position (referred to as the "first locked position" for simplicity) to a second relative rotation-inhibiting position (referred to as the "first locked position" for simplicity) and vice versa. In the first locked position, the mechanism 3375 initially inhibits the follower guide 3321 from rotating in a first direction relative to the barrel cam cylinder 3320 (that is, toward the second locked position) and inhibits rotation of the follower guide 3321 in a second direction relative to the barrel cam cylinder 3320. In the second locked position, the mechanism 3375 initially inhibits the follower guide 3321 from rotating in the second direction relative to the barrel cam cylinder 3320 (that is, toward the first locked position) and inhibits rotation of the follower guide 3321 in the first direction relative to the barrel cam cylinder 3320.

The relative rotation-inhibiting mechanism 3375 includes a longitudinally extending tab 3377 formed near the proximal end of the follower guide 3321. The tab 3377 engages a semi-annular flange 3379 formed near the proximal end of the barrel cam cylinder 3320. As shown in FIGS. 33 and 34, the tab 3377 engages one side of the flange 3379 in the first locked position to inhibit the follower guide 3321 from rotating in a direction away from the second locked position. The tab 3377 engages the other side of the flange 3379 in the second locked position to inhibit the follower guide 3321 from rotating in a direction away from the first locked position.

The relative rotation-inhibiting mechanism 3375 also includes a first magnetic element 3308 that is fixedly carried by the barrel cam cylinder 3320. The first magnetic element 3308 may be a magnet or may be formed from one or more ferromagnetic materials that are attracted to magnets (for example, steel). The relative rotation-inhibiting mechanism 3375 further includes second and third magnetic elements 3310 and 3312 that are fixedly carried by the follower guide 3321. The second and third magnetic elements 3310 and 3312 may be magnets or may be formed from one or more ferromagnetic materials that are attracted to magnets (for example, steel) if the first magnet element 3308 is a magnet.

Interaction of the first magnetic element 3308 with the second and third magnetic elements 3310 and 3312, and the resulting motion of the follower guide 3321 relative to the barrel cam cylinder 3320, are described with reference to the cam slot and aperture profiles illustrated in FIGS. 22A-22C. Referring first to FIG. 22A and upon a first actuation of the trigger assembly, the trigger pin initially moves from position BC1' to BC3'. As the trigger pin moves in this manner, the follower guide 3321 rotates together with the barrel cam cylinder 3320 due to the magnetic attraction forces between the first magnetic element 3308 and the second magnetic element 3310. Stated another way, the first magnetic element 3308 and the second magnetic element 3310 initially hold the follower guide 3321 in the first locked position relative to the barrel cam cylinder 3320.

Referring to FIG. 22B and by continuing the first actuation of the trigger assembly, the trigger pin moves from position BC3' to BC4'. In position BC3', the trigger pin engages the wall of the follower guide aperture. By moving toward position BC4', the trigger pin applies a force to the follower guide 3321 that overcomes the magnetic attraction forces between the first magnetic element 3308 and the second magnetic element 3310. As a result, the first magnetic element 3308 and the second magnetic element 3310 move apart, and the follower guide 3321 is "unlocked" and rotates relative to the barrel cam cylinder 3320 as the trigger pin moves from position BC3' to BC4'. As the trigger pin approaches position BC4', the first magnetic element 3308 and the third magnetic element 3312 are magnetically attracted to each other. The follower guide 3321 thereby enters the second locked position relative to the barrel cam cylinder 3320.

When the user releases the trigger assembly, the trigger pin moves from position BC4' to BC6'. As the trigger pin moves in this manner, the follower guide 3321 rotates together with the barrel cam cylinder 3320 due to the magnetic attraction forces between the first magnetic element 3308 and the third magnetic element 3312. Stated another way, the first magnetic element 3308 and the third magnetic element 3312 hold the follower guide 3321 in the second locked position relative to the barrel cam cylinder 3320 after the first actuation of the trigger assembly.

Still referring to FIG. 22B and upon a second actuation of the trigger assembly, the trigger pin initially moves from position BC6' to BC8'. As the trigger pin moves in this manner, the follower guide 3321 rotates together with the barrel cam cylinder 3320 due to the magnetic attraction forces between the first magnetic element 3308 and the third magnetic element 3312. Stated another way, the first magnetic element 3308 and the third magnetic element 3312 initially hold the follower guide 3321 in the second locked position relative to the barrel cam cylinder 3320.

Referring to FIG. 22C and by continuing the second actuation of the trigger assembly, the trigger pin moves from position BC8' to BC9'. In position BC8', the trigger pin engages the wall of the follower guide aperture. By moving toward position BC9', the trigger pin applies a force to the follower guide 3321 that overcomes the magnetic attraction forces between the first magnetic element 3308 and the third magnetic element 3312. As a result, the first magnetic element 3308 and the third magnetic element 3312 move apart, and the follower guide 3321 is "unlocked" and rotates relative to the barrel cam cylinder 3320 as the trigger pin moves from position BC8' to BC9'. As the trigger pin approaches position BC9', the first magnetic element 3308 and the second magnetic element 3310 are magnetically attracted to each other. The follower guide 3321 thereby returns to the first locked position relative to the barrel cam cylinder 3320.

When the user releases the trigger assembly, the trigger pin moves from position BC9' to BC1'. As the trigger pin moves in this manner, the follower guide 3321 rotates together with the barrel cam cylinder 3320 due to the magnetic attraction forces between the first magnetic element 3308 and the second magnetic element 3310. Stated another way, the first magnetic element 3308 and the second magnetic element 3310 hold the follower guide 3321 in the first locked position relative to the barrel cam cylinder 3320 after the second actuation of the trigger assembly.

In some embodiments, the follower guide 3321 carries one magnetic element, and the barrel cam cylinder 3320 carries two magnetic elements.

Figure 35:
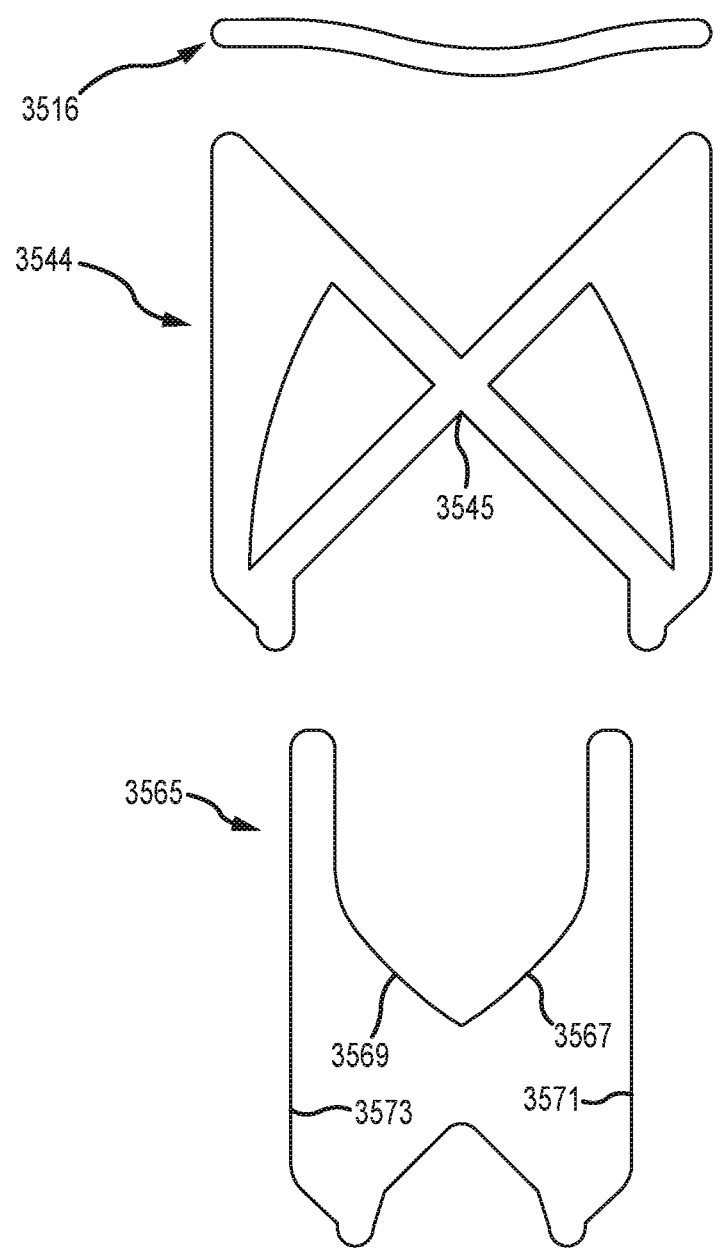
FIG. 35 depicts two-dimensional illustrations of a profile of a cam slot of an embodiment of a cutting tip, a profile of a cam slot of an embodiment of a barrel cam cylinder, and a profile of an aperture of an embodiment of a follower guide.
Figure 36A:
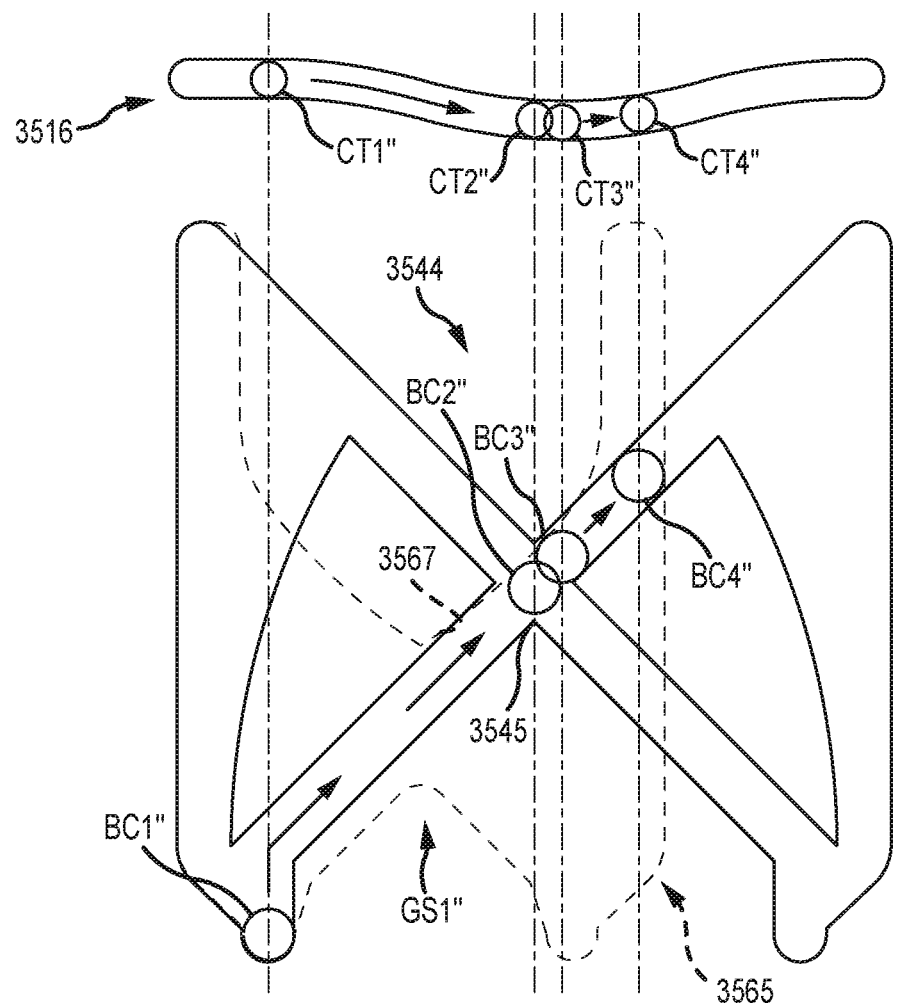
FIG. 36A is an illustration of the cam slot profile of the cutting tip, the cam slot of the barrel cam cylinder, and the profile of the aperture of the follower guide depicting the longitudinal position of the cutting tip in combination with the longitudinal position of the trigger for a particular amount of angular rotation by both the cutting tip and the barrel cam cylinder; the follower guide is illustrated in a first relative rotation-inhibiting position compared to the barrel cam cylinder.
Figure 36B:
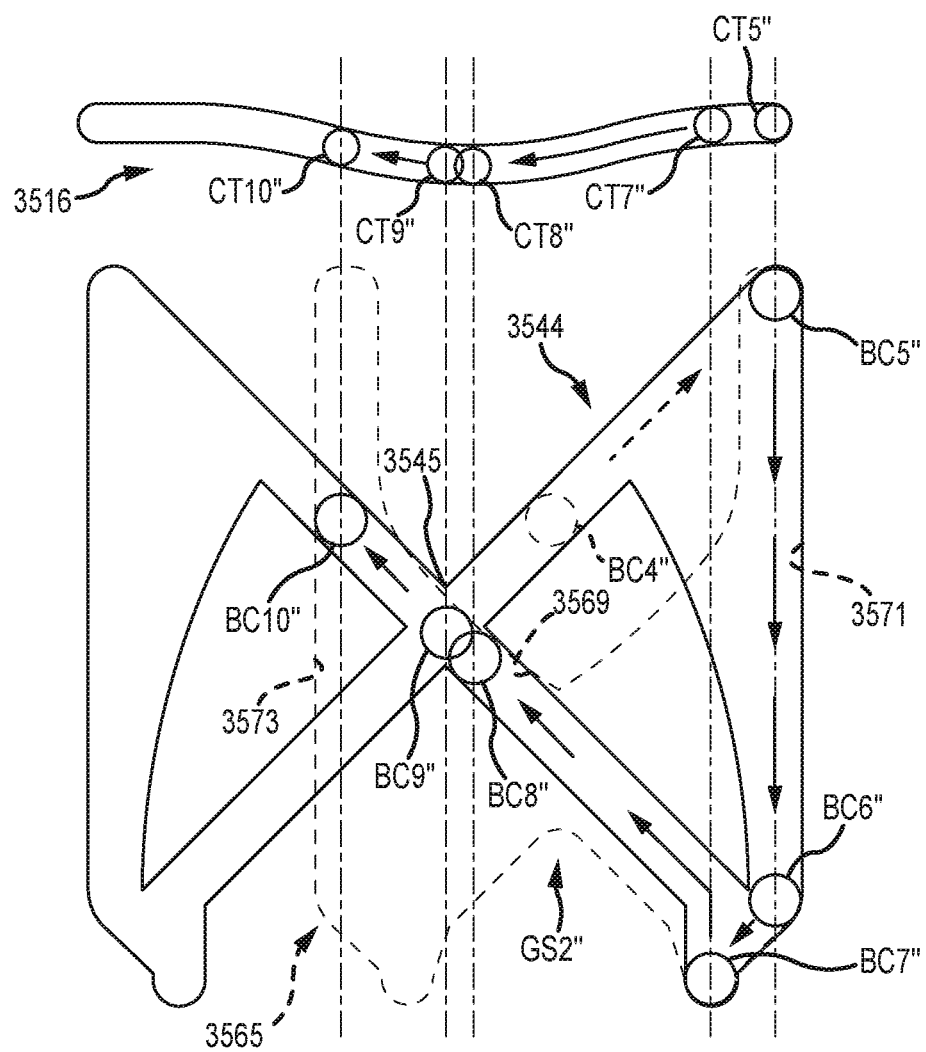
FIG. 36B is another illustration of the cam slot profile of the cutting tip, the cam slot of the barrel cam cylinder, and the profile of the aperture of the follower guide depicting the longitudinal position of the cutting tip in combination with the longitudinal position of the trigger for a particular amount of angular rotation by both the cutting tip and the barrel cam cylinder; the follower guide is illustrated in a second relative rotation-inhibiting position compared to the barrel cam cylinder.
Figure 36C:
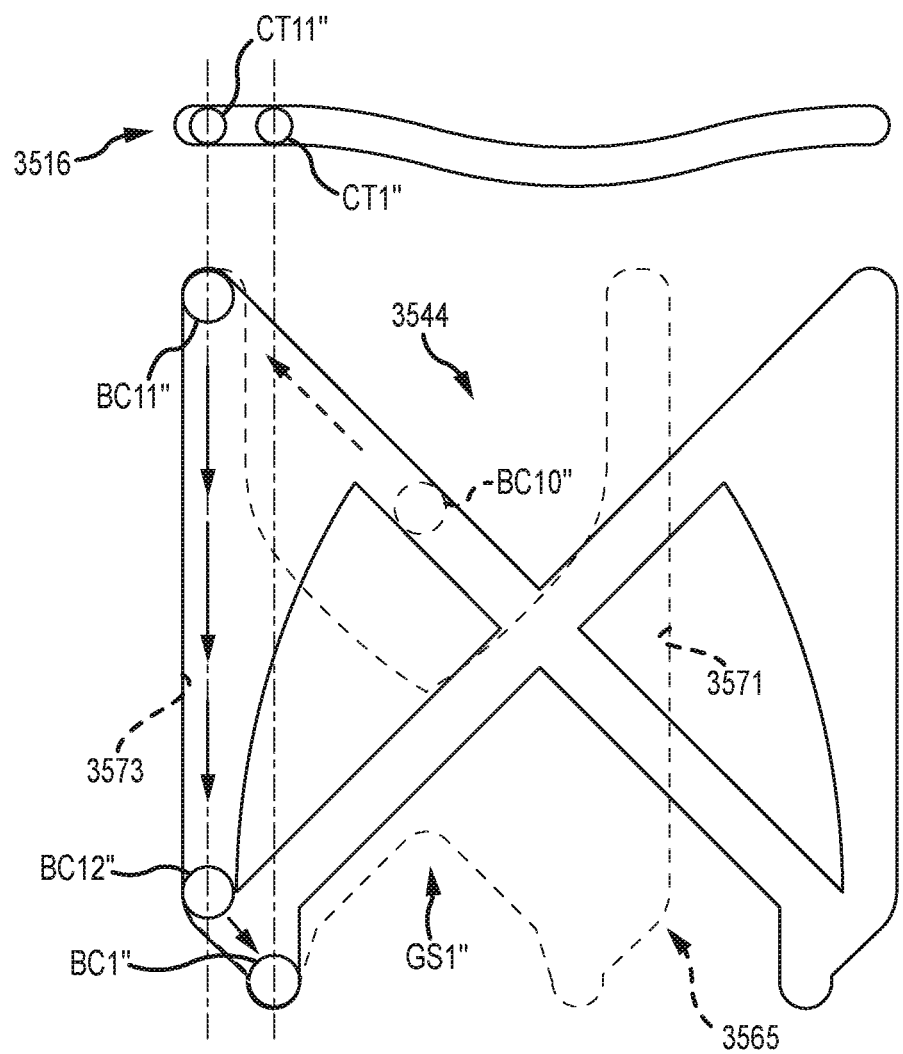
FIG. 36C is another illustration of the cam slot profile of the cutting tip, the cam slot of the barrel cam cylinder, and the profile of the aperture of the follower guide depicting the longitudinal position of the cutting tip in combination with the longitudinal position of the trigger for a particular amount of angular rotation by both the cutting tip and the barrel cam cylinder; the follower guide is again illustrated in the first relative rotation-inhibiting position compared to the barrel cam cylinder.

FIG. 35 depicts two-dimensional illustrations of the profile of a cutting tip slot 3516, the profile of a barrel cam slot 3544, and the profile of a follower guide aperture 3565 that may be formed on any of the cutting tips, barrel cam cylinders, and follower guides, respectively, described herein. FIGS. 36A-36C depict the how actuation of a trigger (which may be any of the triggers described herein), and the resulting movement of the trigger pin 3528 (which may be any of the trigger pins described herein), results in rotational movement of the barrel cam cylinder, the follower guide, and the cutting tip, and translation movement of the cutting tip. In these figures, a horizontal axis for the profiles of the slots 3516 and 3544 is the degree(s) of rotation of the cutting tip and the barrel cam cylinder. A vertical axis for the profile of the cam slot 3516 for the cutting tip is the amount of longitudinal displacement, if any, of the cutting tip. The vertical axis for the profile of the cam slot 3544 for the barrel cam cylinder is the amount of longitudinal displacement of the trigger assembly (and trigger pin).

In FIGS. 35A-35C, the aperture 3565 of the follower guide is shown as a dashed line and is overlaid on the profile of the cam slot 3544 for the barrel cam cylinder to illustrate the rotational position of the aperture 3565 relative to the cam slot 3544. As shown in FIGS. 35A-35C and explained in further detail below, the rotational position of the aperture 3565 changes relative to the cam slot 3544 during actuation of the trigger.

Generally, an initial, or first, actuation of the trigger (that is, pulling the trigger as far as permitted by the handle assembly and then releasing the trigger so that it returns to its home position) results in a net rotational displacement of the cutting tip and the barrel cam cylinder about 254 degrees in one direction—clockwise when looking from the handle to the tip. The first actuation also extends the cutting tip from the outer band and then returns the cutting tip to the sheathed position as the cutting tip rotates. A subsequent, or second, actuation of the trigger results in a net rotational displacement of the cutting tip and the barrel cam cylinder about 254 degrees in the opposite direction—counter-clockwise when looking from the handle to the tip. The second actuation also extends the cutting tip from the outer band and then returns the cutting tip to the sheathed position as the cutting tip rotates. Additional "odd" actuations (that is, a third actuation, a fifth actuation, and so on) cause the same device motions as the first actuation of the trigger. Additional "even" actuations (that is, a fourth actuation, a sixth actuation, and so on) cause the same device motions as the second actuation of the trigger.

Referring specifically to FIG. 36A, prior to the first actuation of the trigger, the trigger pin is at a first home position (BC1") within the barrel cam cylinder, the guide pin is at its initial position (CT1"), and the cutting tip is at a recessed position within the outer sheath. In addition, the follower guide is at its first relative rotation-inhibiting position (GS1") with respect to the barrel cam cylinder. Upon initiating the first actuation of the trigger, the trigger pin moves proximally, and the barrel cam cylinder, the cutting tip, and the follower guide rotate in a clockwise direction relative to the trigger pin (from a vantage point proximal of the barrel cam cylinder). When the trigger pin is at position BC2", the trigger pin is in the intersection 3545 of the barrel cam slot 3544. Additionally, when the trigger pin is at position BC2" (i) the barrel cam cylinder and cutting tip have rotated about 127 degrees in a clockwise direction since initiating the first actuation of the trigger, (ii) the guide pin is at position CT2", and (iii) the cutting tip is at a partially extended position.

Continuing to refer to FIG. 36A, when the trigger pin is at position BC2", the trigger pin abuts a first curved wall 3567 of the follower guide aperture 3565. Because the first curved wall 3567 of the follower guide aperture 3565 is aligned with one path of the intersection 3545 of the barrel cam slot 3544, the follower guide prevents the trigger pin from traveling in the alternative path and guides the trigger pin straight through the intersection 3545 of the barrel cam slot 3544 as the trigger pin passes position BC2". In some embodiments, the apex between the first curved wall 3567 and the second curved wall 3569 is offset from the wall of the barrel cam slot 3544 in a longitudinal direction (for example, by about 0.025 inches) to inhibit the trigger pin from engaging the apex. This facilitates guiding the trigger pin straight through the intersection 3545 of the barrel cam slot 3544. In some embodiments, the first curved wall 3567 extends beyond the wall of the barrel cam slot 3544 (for example, the perpendicular distance between the barrel cam slot 3544 and the furthest point on the first curved wall 3567 may be about 0.010 inches) to facilitate smooth motion of the trigger pin as the trigger pin passes through the intersection 3545 and to permit a relatively small amount of misalignment between the barrel cam and the follower guide.

As the user continues to pull the trigger, and the trigger pin continues to move proximally, the barrel cam cylinder, the cutting tip, and the follower guide continue to rotate in a clockwise direction from position BC2" to position BC3". When the trigger pin is at position BC3", (i) the barrel cam cylinder and cutting tip have rotated about 140 degrees in a clockwise direction since initiating the first actuation of the trigger, (ii) the guide pin is at position CT3", and (iii) the cutting tip is at a fully extended position.

As the user continues to pull the trigger, and the trigger pin continues to move proximally, and the barrel cam cylinder, the cutting tip, and the follower guide continue to rotate in a clockwise direction. Specifically, the trigger pin moves from position BC3" to position BC4". When the trigger pin is at position BC4", (i) the barrel cam cylinder and cutting tip have rotated about 177 degrees in a clockwise direction since initiating the first actuation of the trigger, (ii) the guide pin is at position CT4", and (iii) the cutting tip is at a partially extended position.

When the trigger pin is at position BC4", the trigger pin abuts a wall 3571 of the follower guide aperture 3565. As the trigger pin has moved from the first home position (BC1") to position BC4", the follower guide and barrel cam cylinder have rotated in unison with one another due to the presence of one of the relative rotation-inhibiting mechanisms described above. For example, the barrel cam cylinder and the follower guide include the relative rotation-inhibiting mechanism 2475 (see FIGS. 24-28). In this case, the first spring prong 2410 on the follower guide has been engaged with the curved recess 2404 of the protrusion 2402 of the barrel cam cylinder, thereby preventing the follower guide and barrel cam cylinder from rotationally moving relative to one another. Referring to FIG. 36B, as the trigger pin moves beyond position BC4" towards position BC5", the trigger pin engages the wall 3571 of the follower guide, thereby rotating the follower guide in a counter-clockwise direction relative to the barrel cam cylinder and forcing the follower guide from its first relative rotation-inhibiting position (GS1") to a movable position. That is, as the trigger pin moves from position BC4" to position BC5", the follower guide is in a movable position relative to the barrel cam cylinder. Once the trigger pin reaches position BC5", the follower guide and barrel cam cylinder are in a second relative rotation-inhibiting position (GS2"). In the second relative rotation-inhibiting position (GS2"), for example, the second spring prong 2412 on the follower guide engages the curved recess 2404 of the protrusion 2402 of the barrel cam cylinder, and a first engagement surface 2413 on the follower guide engages the protrusion 2402 to prevent the follower guide from further rotating in the counter-clockwise direction relative to the barrel cam cylinder.

Continuing to refer to FIG. 36B, as the user continues to pull the trigger to move the trigger pin from position BC4" to position BC5", the barrel cam cylinder and the cutting tip continue to rotate in a clockwise direction relative to the trigger pin. The follower guide, however, does not continue to rotate relative to the trigger pin and thereby rotates relative to the barrel cam cylinder. Specifically, the follower guide rotates about 110 degrees in a counter-clockwise direction to a second relative rotation-inhibiting position (GS2") relative to the barrel cam cylinder. When the trigger pin is at position BC5" (i) the trigger has reached the end of its proximal travel, (ii) the barrel cam cylinder has rotated about 287 degrees in a clockwise direction since initiating the first actuation of the trigger, (iii) the guide pin is at position CT5", and (iv) the cutting tip is at its most recessed position. In addition, the cutting tip has rotated a total of about 284 degrees in a clockwise direction since initiating the first actuation of the trigger. The cutting tip rotates less than the barrel cam cylinder because the guide pin engages the wall of the cutting tip slot 3516 (that is, the guide pin reaches position CT5") before the trigger pin reaches position BC5". The barrel cam cylinder rotates about 3 degrees in the clockwise direction after the guide pin engages the wall of the cutting tip slot 3516. As a result, the barrel cam cylinder rotates about 3 degrees relative to the cutting tip when the trigger pin approaches position BC5". The relative rotation between the barrel cam cylinder and the cutting tip is accounted for by rotational deflection of the flexible inner sheath.

After the trigger pin reaches position BC5", the user can release the trigger. Upon the user releasing the trigger, the trigger and trigger pin reverse direction and travel toward their distal position due to the constant force spring attached to the trigger. As the trigger and trigger pin begin to move toward their distal position, the barrel cam cylinder and cutting tip are rotationally stationary relative to the trigger pin. Accordingly, upon the user releasing the trigger, the trigger pin moves from position BC5" toward position BC6". When the trigger is at position BC6" (i) the barrel cam cylinder has rotated about 287 degrees in a clockwise direction since initiating the first actuation of the trigger (ii) the guide pin is still at position CT5", and (iii) the cutting tip is still at its most recessed position. At position BC6", however, the trigger pin is still not at its most distal position. To reach the trigger pin's most distal position BC7", the barrel cam cylinder rotates about 33 degrees in a counter-clockwise direction. In some embodiments, the trigger pin engages a radiused corner of the wall of the barrel cam slot 3544 and/or the wall of the follower guide aperture 3565 (for example, a 0.050 inch radius) when moving from position BC6" to position BC7". Such a structure may facilitate reliably sliding the trigger pin to position BC7". When the trigger pin is at position BC7", the trigger pin is at a second home position within the barrel cam cylinder. When the trigger pin is at position BC7", (i) the barrel cam cylinder and the cutting tip have rotated a total of about 254 degrees in a clockwise direction since initiating the first actuation of the trigger, (ii) the guide pin is at position CT7", and (iii) the cutting tip is recessed within the outer sheath.

Still referring to FIG. 36B, when the trigger pin is at its second home position (BC7"), the follower guide is at its second relative rotation-inhibiting position (GS2"). Upon initiating a second actuation of the trigger to move the trigger pin proximally, the follower guide and the barrel cam cylinder remain stationary with respect to one another, and the barrel cam cylinder, the cutting tip, and the follower guide rotate in a counter-clockwise direction. When the trigger pin is at position BC8", (i) the barrel cam cylinder and cutting tip have rotated about 114 degrees in a counter-clockwise direction since initiating the second actuation of the trigger, (ii) the guide pin is at position CT8", and (iii) the cutting tip is at its most extended position.

As the user continues the second actuation of the trigger, and the trigger pin continues to move proximally, the barrel cam cylinder, the cutting tip, and the follower guide continue to rotate in a counter-clockwise direction relative to the trigger pin. When the trigger pin is at position BC9", (i) the barrel cam cylinder and cutting tip have rotated about 127 degrees in a counter-clockwise direction since initiating the second actuation of the trigger, (ii) the guide pin is at position CT9", (iii) the cutting tip is at a partially extended position, and (iv) the trigger pin is at the intersection 3545 of the barrel cam slot 3544. When the trigger pin is at position BC9", the trigger pin abuts a second curved wall 3569 of the follower guide aperture 3565. Because the second curved wall 3569 of the follower guide aperture 3565 is aligned with one path of the intersection 3545 of the barrel cam slot 3544, the follower guide prevents the trigger pin from traveling in the alternative path and guides the trigger pin straight through the intersection 3545 of the barrel cam slot 3544 as the trigger pin passes position BC9".

As the user continues to actuate the trigger, and the trigger pin continues to move proximally, the barrel cam cylinder, the cutting tip, and the follower guide continue to rotate in a counter-clockwise direction. When the trigger pin is at position BC10", (i) the barrel cam cylinder and cutting tip have rotated about 177 degrees in a clockwise direction since initiating the second actuation of the trigger, (ii) the guide pin is at position CT10", (iii) the cutting tip is at a partially extended position, and (iv) the trigger pin abuts a wall 3573 of the follower guide aperture 3565.

As the trigger pin has moved from its second home position (BC7") to position BC10", the follower guide and barrel cam cylinder have rotated in unison with one another due to the presence of the relative rotation-inhibiting mechanism. For example, the second spring prong 2412 on the follower guide has been engaged with the curved recess 2404 of the protrusion 2402 of the barrel cam cylinder, thereby preventing the follower guide and barrel cam cylinder from rotationally moving relative to one another. Referring to FIG. 36C, as the trigger pin moves beyond position BC10" towards position BC11", the trigger pin engages the wall 3573 of the follower guide, thereby rotating the follower guide in the clockwise direction relative to the barrel cam cylinder and forcing the follower guide from its second relative rotation-inhibiting position (GS2") to a movable position. That is, as the trigger pin moves from position BC10" to position BC11", the follower guide is in a movable position relative to the barrel cam cylinder. Once the trigger pin reaches position BC11", the follower guide and barrel cam cylinder have returned to the first relative rotation-inhibiting position (GS1"). In the first relative rotation-inhibiting position (GS1"), for example, the first spring prong 2410 on the follower guide engages the curved recess 2404 of the protrusion 2402 of the barrel cam cylinder, and a second engagement surface 2414 on the follower guide (see FIG. 25) engages the protrusion 2402 to prevent the follower guide from further rotating in the clockwise direction relative to the barrel cam cylinder.

Continuing to refer to FIG. 36C, as the user continues the second actuation of the trigger, and the trigger pin continues to move proximally, the barrel cam cylinder and the cutting tip continue to rotate in a counter-clockwise direction. The follower guide, however, does not continue to rotate relative to the trigger pin, and the trigger pin rotates only relative to the barrel cam cylinder. Specifically, the follower guide rotates about 110 degrees in a clockwise direction to the first relative rotation-inhibiting position (GS1") relative to the barrel cam cylinder. When the trigger pin is at position BC11" (i) the trigger has reached the end of its proximal travel, (ii) the barrel cam cylinder and the cutting tip have rotated about 287 degrees in a counter-clockwise direction since initiating the second actuation of the trigger, (iii) the guide pin is at position CT11", and (iv) the cutting tip is at its most recessed position.

After the trigger pin reaches position BC11", the user can release the trigger. Upon the user releasing the trigger, the trigger and trigger pin reverse direction and travel toward their distal position due to the constant force spring attached to the trigger. As the trigger and trigger pin begin to move toward their distal position, the barrel cam cylinder and cutting tip are rotationally stationary relative to the trigger pin. Accordingly, upon the user releasing the trigger, the trigger pin moves from position BC11" toward position BC12". When the trigger is at position BC12" (i) the barrel cam cylinder and the cutting tip are still rotated about 287 degrees in a counter-clockwise direction since initiating the second actuation of the trigger (ii) the guide pin is still at position CT11", and (iii) the cutting tip is still at its most recessed position. As the trigger and trigger pin continue to move toward their distal position, the barrel cam cylinder and cutting tip rotate about 33 degrees in a clockwise direction relative to the trigger pin and the trigger pin returns to its first home position (BC1"). In some embodiments, the trigger pin engages a radiused corner of the wall of the barrel cam slot 3544 and/or the wall of the follower guide aperture 3565 (for example, a 0.050 inch radius) when moving from position BC12" to position BC1". Such a structure may facilitate reliably sliding the trigger pin to position BC1". When the trigger pin returns to its first home position (BC1"), the guide pin returns to its initial position (CT1"), and the cutting tip remains at a recessed position within the outer sheath. The user may then repeat the process, if so desired.

Figure 37:
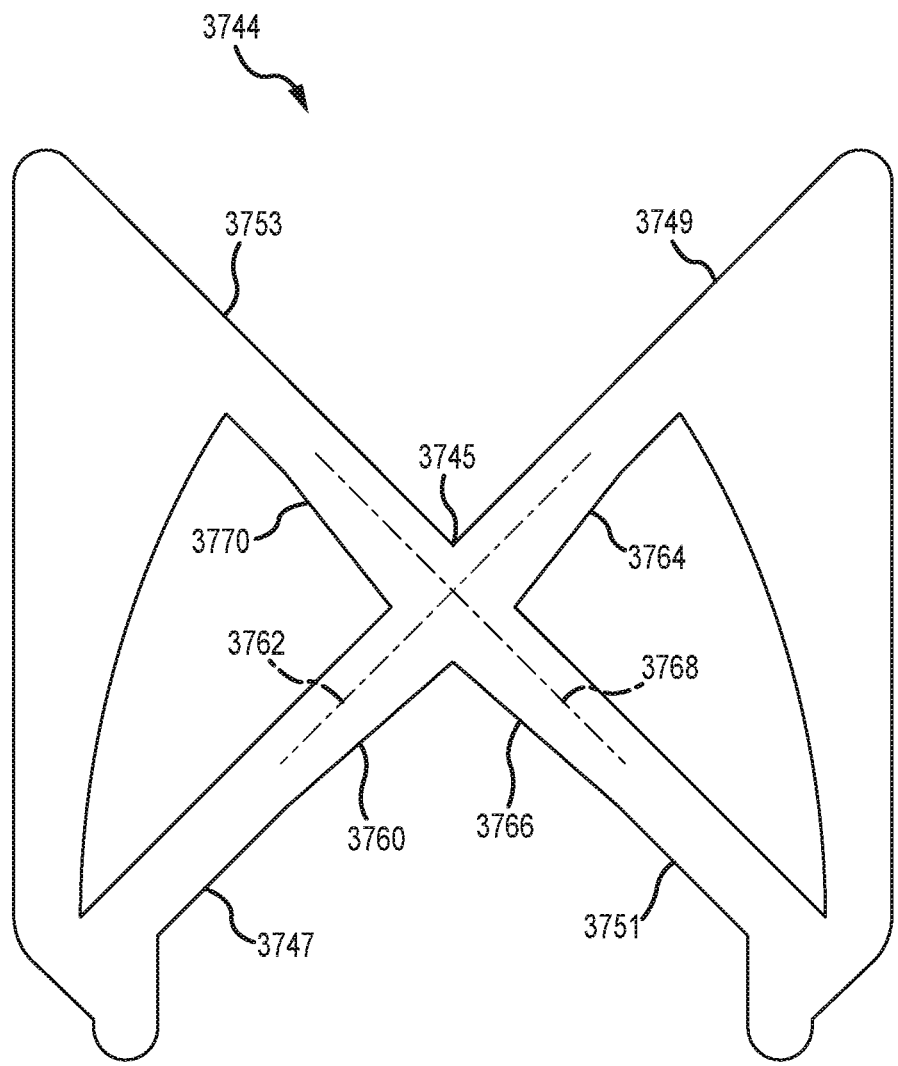
FIG. 37 depicts a two-dimensional illustration of a profile of a cam slot of an embodiment of a barrel cam cylinder.

FIG. 37 depicts a two-dimensional illustration of the profile of a barrel cam slot 3744 that may be formed on any of the barrel cam cylinders described herein. The cam slot 3744 defines a generally "hourglass"-like or "figure eight"-like path for the follower (for example, the trigger pin 1528). The trigger pin traverses about half of the cam slot 3744 when an initial, or first, actuation is applied to the trigger, and the trigger pin traverses the remainder of the cam slot 3744 (that is, about half of the cam slot 3744) when a subsequent, or second, actuation is applied to the trigger. In each case, the follower guide (for example, the follower guide 1521) causes the trigger pin to travel straight through the intersection (or crossing portion) 3745 of the cam slot 3744 during each actuation of the trigger. Stated another way, the follower guide causes the trigger pin to travel from a first leg 3747 of the cam slot 3744 to a second leg 3749 of the cam slot 3744, and then from a third leg 3751 of the cam slot 3744 to a fourth leg 3753 of the cam slot 3744.

Each of the legs 3747, 3749, 3751, and 3753 is shaped to inhibit the trigger pin from engaging the walls of the legs 3747, 3749, 3751, and 3753 when travelling through the intersection 3745 and potentially binding up with the barrel cam assembly. In some embodiments, each of the legs 3747, 3749, 3751, and 3753 has a width that taperingly increases proceeding toward the intersection 3745. Specifically, the first leg 3747 includes a first angled wall 3760 that is adjacent to the intersection 3745 and disposed on a distal side of the first leg 3747. The first angled wall 3760 is angled away from the first trigger pin path 3762 (that is, the path traversed by the trigger pin during the first actuation of the trigger) proceeding toward the intersection 3745. The first angled wall 3760 may have a length in the range of about 0.25 to 0.40 inches, and more specifically about 0.33 inches, and may be angled away from the first trigger pin path 3762 by an angle in the range of about 1 to 7 degrees, and more specifically about 4 degrees. Similarly, the second leg 3749 includes a second angled wall 3764 that is adjacent to the intersection 3745 and disposed on a distal side of the second leg 3749. The second angled wall 3764 is angled away from the first trigger pin path 3762 proceeding toward the intersection 3745. The second angled wall 3764 may have a length in the range of about 0.18 to 0.32 inches, and more specifically about 0.25 inches, and may be angled away from the first trigger pin path 3762 by an angle in the range of about 4 to 10 degrees, and more specifically about 7 degrees. The third leg 3751 includes a third angled wall 3766 that is adjacent to the intersection 3745 and disposed on a distal side of the third leg 3751. The third angled wall 3766 is angled away from the second trigger pin path 3768 (that is, the path traversed by the trigger pin during the second actuation of the trigger) proceeding toward the intersection 3745. The third angled wall 3766 may have a length in the range of about 0.25 to 0.40 inches, and more specifically about 0.33 inches, and may be angled away from the second trigger pin path 3768 by an angle in the range of about 1 to 7 degrees, and more specifically about 4 degrees. The fourth leg 3753 includes a fourth angled wall 3770 that is adjacent to the intersection 3745 and disposed on a distal side of the fourth leg 3753. The fourth angled wall 3770 is angled away from the second trigger pin path 3768 proceeding toward the intersection 3745. The fourth angled wall 3770 may have a length in the range of about 0.18 to 0.32 inches, and more specifically about 0.25 inches, and may be angled away from the second trigger pin path 3768 by an angle in the range of about 4 to 10 degrees, and more specifically about 7 degrees.

The discussion above describes a barrel cam cylinder and a follower guide in the context of a medical device. However, barrel cam cylinders and follower guides according to the disclosure may be used with other types of devices (for example, non-medical devices) to convert a translational input to a rotational output. That is, barrel cam cylinders and follower guides according to the disclosure may be used such that a first translational input (for example, a first actuation of a translatable trigger) causes a first rotational output (for example, rotation of a shaft in a first direction) and a second translational input (for example, a second actuation of the translatable trigger) causes a second rotational output (for example, rotation of the shaft in a second direction).

The discussion above discusses that the inner sheath, including the cutting tip, travel at certain rates (e.g., constant and/or variable). However, the rates are also dependent upon the speed at which the inner sheath rotates and travels longitudinally (i.e., extends and/or retracts), and in turn, upon the speed of the actuation of the trigger assembly, including the longitudinal movement of the trigger and the rotational movement of the barrel cam cylinder. Accordingly, the discussion and/or comparison of the rates at which the blade travels assumes that the means for actuating extends the inner sheath at a relatively constant speed. Regardless of whether this assumption is correct, the greater the amount of blade extension per predetermined amount of rotation, the blade will extend at a greater rate and speed, thereby providing the surgical device with the ability to cut more tissue per rotation.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

A number of variations and modifications of the disclosure may be used. It would be possible to provide for some features of the disclosure without providing others.

In some embodiments, the systems and methods of this disclosure may be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein may be used to implement the various aspects of this disclosure. Exemplary hardware that may be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing may also be constructed to implement the methods described herein.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

For example, although a pin and slot cam configuration is discussed within this disclosure, other possible cam configurations may be used. For example, a captured ring cam configuration may be used. A captured ring cam configuration may include a ring that is attached to at least one of the inner sheath (or inner member attached to the inner sheath) or the outer sheath (or outer member attached to the outer sheath) and that is captured by two angled lobes on the other sheath (or member). Although the ring may be captured by one lobe, it may be preferred for the ring to be captured by two lobes—one on each side of the ring—such that cutting surface may be forced in both a proximal direction (toward a retraction position) and distal direction (toward an extended direction). The benefit of being able to force the cutting surface in both directions with the aid of the captured cam configuration potentially negates the need for a spring or other retraction mechanism to force the inner sheath (or inner member) and cutting surface back within the outer sheath (or outer member.

Another example of an alternate embodiment may include replacing the cutting tip with a dilator top or separator tip. A further example of an alternate embodiment may include varying the degrees of rotation of the inner sheath assembly or the barrel cam cylinder in the clockwise and/or counter-clockwise direction. An even further example of an alternate embodiment may include the barrel cam cylinder and the inner sheath assembly first rotating in a counter-clockwise direction followed by rotating in a clockwise direction.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for removing an implanted object from a body vessel, the device comprising:
    a sheath assembly comprising an outer sheath assembly and an inner sheath assembly, and a pin;
        the outer sheath assembly comprising an outer sheath and an outer band, the outer band coupled to the pin;
        the inner sheath assembly comprising an inner sheath and a tip, wherein the tip has a cutting surface;
            the inner sheath comprising a proximal end and a distal end, wherein the distal end of the inner sheath is coupled to the tip;
            the tip comprising a cam slot for receipt of and cooperation with the pin; and
    a handle assembly comprising a trigger and a barrel cam cylinder, the trigger comprising a trigger pin, the barrel cam cylinder comprising a barrel cam cylinder slot for receipt and cooperation with the trigger pin, wherein the proximal end of the inner sheath is coupled to the barrel cam cylinder such that upon the trigger pin moving proximally in a longitudinal direction, the barrel cam cylinder rotates in both a clockwise direction and a counter clockwise direction, thereby causing the tip to rotate in both the clockwise direction and the counter clockwise direction while the tip moves longitudinally.

2. The device of claim 1, wherein the outer sheath assembly is stationary and the inner sheath assembly is capable of rotating.

3. The device of claim 1, wherein the pin couples the tip of the inner sheath assembly to the outer band of the outer sheath assembly.

4. The device of claim 1, wherein the handle assembly further comprises a spring assembly coupled to the trigger.

5. The device of claim 1, wherein the spring is a constant force spring.

6. A device for removing an implanted object from a body vessel, the device comprising:
    a sheath assembly comprising an outer sheath assembly and an inner sheath assembly, and a pin, wherein the outer sheath assembly and the inner sheath assembly each comprise a proximal end and a distal end, wherein the distal end of the outer sheath assembly is coupled to the distal end of the inner sheath assembly by the pin;
    the inner sheath assembly comprising an inner sheath and a tip at its distal end, wherein the tip has a cutting surface; the tip comprising a slot for receipt of and cooperation with the pin; and
    a handle assembly comprising a trigger and a barrel cam cylinder, the trigger comprising a trigger pin, the barrel cam cylinder comprising a barrel cam cylinder slot for receipt and cooperation with the trigger pin, wherein the proximal end of the inner sheath is coupled to the barrel cam cylinder by the trigger pin such that upon the trigger pin moving proximally in a longitudinal direction, the barrel cam cylinder rotates in a first direction and a second direction, wherein the first direction is different than the second direction, wherein the tip moves longitudinally while the barrel cam cylinder rotates in the first direction, and wherein the tip moves longitudinally while the barrel cam cylinder rotates in the second direction.

7. The device of claim 6, wherein the tip extends from and retracts into the outer sheath while barrel cam cylinder rotates in the second direction.

8. The device of claim 6, wherein the barrel cam cylinder comprises an exterior surface, and the barrel cam cylinder slot is discontinuous around the exterior surface.

9. The device of claim 6, wherein the barrel cam cylinder comprises an exterior surface, and the barrel cam cylinder slot is continuous around the exterior surface.

10. The device of claim 6, wherein the tip extends from and retracts into the outer sheath while barrel cam cylinder rotates in the first direction.

11. The device of claim 10, wherein the tip extends from and retracts into the outer sheath while barrel cam cylinder rotates in the second direction.

* * * * *